United States Patent
Kari et al.

(10) Patent No.: US 6,348,445 B1
(45) Date of Patent: Feb. 19, 2002

(54) BIOLOGICALLY ACTIVE PEPTIDES WITH REDUCED TOXICITY IN ANIMALS AND A METHOD FOR PREPARING SAME

(75) Inventors: U. Prasad Kari, Hatsfield; Taffy J. Williams, Lansdale; Michael McLane, Blue Bell, all of PA (US)

(73) Assignee: Magainin Pharmaceuticals, Inc., Plymouth Meeting, PA (US)

(*) Notice: Subject to any disclaimer, the term of this patent is extended or adjusted under 35 U.S.C. 154(b) by 0 days.

(21) Appl. No.: 09/115,737

(22) Filed: Jul. 15, 1998

Related U.S. Application Data

(63) Continuation-in-part of application No. 08/893,006, filed on Jul. 15, 1997, now abandoned, which is a continuation-in-part of application No. 08/465,330, filed on Jun. 5, 1995, now abandoned, which is a division of application No. 08/184,462, filed on Jan. 18, 1994, now abandoned, which is a continuation-in-part of application No. 07/891,201, filed on Jun. 1, 1992, now abandoned.

(51) Int. Cl.$^7$ .......................... A61K 38/00; C07K 5/00; C07K 7/00
(52) U.S. Cl. ........................ 514/12; 530/324; 530/333; 530/334
(58) Field of Search ........................... 514/12; 530/324, 530/333, 334; 424/184.1, 185.1

(56) References Cited

U.S. PATENT DOCUMENTS

| | | | |
|---|---|---|---|
| 5,070,188 A | 12/1991 | Njieha et al. | 514/12 |
| 5,114,921 A | 5/1992 | Zasloff | 514/12 |
| 5,208,220 A | 5/1993 | Berkowitz | 514/13 |
| 5,221,664 A | 6/1993 | Berkowitz et al. | 514/6 |
| 5,254,537 A | 10/1993 | Zasloff | 514/13 |
| 5,294,605 A | 3/1994 | Houghten et al. | 514/13 |
| 5,358,934 A | 10/1994 | Borovsky et al. | 514/17 |
| 5,424,290 A | 6/1995 | Maloy et al. | 514/13 |
| 5,470,950 A | 11/1995 | Maloy et al. | 530/324 |
| 5,654,274 A | 8/1997 | Kari | 428/542.4 |
| 5,686,563 A | 11/1997 | Kari | 530/326 |

FOREIGN PATENT DOCUMENTS

| | | |
|---|---|---|
| WO | WO 89/11290 | 11/1989 |
| WO | WO 91/12015 | 8/1991 |
| WO | WO 91/16066 | 10/1991 |
| WO | WO 91/17760 | 11/1991 |
| WO | WO 92/00090 | 1/1992 |
| WO | WO 92/01462 | 2/1992 |
| WO | WO 92/22317 | 12/1992 |
| WO | WO 93/05802 | 4/1993 |
| WO | WO 93/24138 | 12/1993 |
| WO | WO 94/13697 | 6/1994 |

OTHER PUBLICATIONS

Al–Obeidi et al., "Synthesis and Biological Activities of Fatty Acid Conjugates of a Cyclic Lactam α–Melanotropin," *J. Med. Chem.* 35, 118–23 (1992).

C. Puyal et al., "Design of a Short Membrane–destabilizing Peptide Covalently Bound to Liposomes," *Biochimica et Biophysica Acta* 1195, 259–66 (1994).

Kato et al., "Conformational Studies of Amphipathic α–helical Peptides Containing an Amino Acid with a Long Alkyl Chain and their Anchoring to Lipid Bilayer Liposomes," *Biochimica et Biophysica Acta*, 1063:191–196 (1991).

Christensen et al., "Channel–forming Properties of Cecropins and Related Model Compounds Incorporated into Planar Liquid Membranes," *PNAS*, 85:5072–5076 (1988).

Richter et al., "Sequence of Preparocaerulein cDNAs as Cloned from Skin of *Xenopus laevis*," *J. Biol. Chem.*, 261(8):3676–3680 (1986).

Gibson et al., "Novel Peptide Fragments Originating from PGL$^a$ and the Caerulein and Xenopsin Precursors from *Xenopus laevis*," *J. Biol. Chem.*, 261(12):5341–5349 (1986).

Wakabayashi et al., "Complete Nucleotide Sequence of mRNA for Caerulein Precursor from Xenopus Skin: the mRNA Contains an Unusual Repetitive Structure," *Nucleic Acids Research* 13(6):1817–1828(1985).

Prasad et al., "SAR Studies on PGL$^a$: An Antimicrobial Peptide Isolated from Frog Skin Extracts," Peptides 1992, Proceedings of the 22nd European Peptide Symposium, pp. 755–756.

(List continued on next page.)

*Primary Examiner*—Avis M. Davenport
(74) *Attorney, Agent, or Firm*—Morgan, Lewis & Bockius LLP

(57) ABSTRACT

The present invention relates to biologically active peptides with reduced toxicity and methods of preparing them. The peptides of the invention, which can be unsubstituted or N-terminal substituted have the formula:

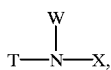

wherein X is a biologically active amphiphilic ion channel-forming peptide or protein, T is a lipophilic moiety or hydrogen, and W is T or hydrogen. Preferably T is:

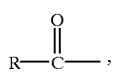

wherein R is a hydrocarbon (alkyl or aromatic or alkylaromatic) having at least 2 and no more than 10 carbon atoms. T is preferably an octanoyl group. The peptides and proteins of the invention have improved antimicrobial and anti-tumor biological activity while exhibiting reduced toxicity. A preferred method of reducing toxicity involves the formation of related methane sulfonate derivatives or analogues. Additionally, the compounds of the invention may be used to treat sepsis, septic shock, and lung infections, such as those occurring in cystic fibrosis.

6 Claims, 16 Drawing Sheets

OTHER PUBLICATIONS

Bruin et al., "Sepsis Background and Perspectives," International Business Communication's Fourth Annual Conference: The Shift in R&D Strategies for the Prevention and Treatment of Endotoxemia & Sepsis, pp. 1–30 (Jun. 13–15, 1994).

Corriveau et al., "Endotoxin as a Therapeutic Target in Septic Shock," *Infectious Agents and Disease*, vol. 2, pp. 35–43 (1993).

Cross et al., "Choice of Bacteria in Animal Models of Sepsis," *Infection and Immunity*, Jul. 1993, pp. 2741–2747.

Egorova et al., Abstract: "Colorimetry for lipopolysaccharide assay in immunological investigations," *Immunologiya (Moscow)*, vol. 4, pp. 79–82 (1988).

Fomsgaard, "Antibodies to lipopolysaccharides: Some diagnostic and protective aspects," *APMIS Suppl.* 18, vol. 98, pp. 5–38 (1990).

Kielian et al., "CD14 and other recognition molecules of lipopolysaccharide: a review," *Immunopharmacology*, vol. 29, No. 3, pp. 187–205 (1995).

Larrick et al., "A Novel Granulocyte–Derived Peptide with Lipopolysaccharide–Neutralizing Activity," *J. of Immunology*, vol. 152(1), pp. 231–240 (1994).

Laskin et al., "Macrophages and Inflammatory Mediators in Tissue Injury," *Annual Review of Pharmacology and Toxicology*, vol. 35, pp. 655–677 (1995).

Maloy et al., "Structure–Activity Studies on Magainins and Other Host Defense Peptides," *Biopolymers (Peptide Science)*, vol. 37, pp. 105–122 (1995).

Masoud et al., "Structural characterization of the O–antigenic polysaccharide of *Escherichia coli* serotype O17 lipopolysaccharide," *Biochemistry and Cell Biology*, vol. 74, No. 22, pp. 241–248 (1996).

Mikheeva et al., "Use of carbocyanine dyes in the analysis of bacterial lipopolysaccharides. (*Endotoxins*). II. The lipopolysaccharide of *Salmonella typhi*," *Khim. Prir. Soedin. (Russian)*, vol. 6, pp. 790–792 (1987).

Mikheeva et al., "Use of carbocyanine dyes in the analysis of bacterial lipopolysaccharides. (*Endotoxins*). III. Lipopolysaccharides of *Yersinia enterocolitica*," *Khim. Prir. Soedin. (Russian)*, vol. 1, pp. 29–35 (1988).

Natanson et al., "Selected Treatment Strategies for Septic Shock Based on Proposed Mechanisms of Pathogenesis," *Annals of Internal Medicine*, vol. 120, No. 9, pp. 771–783 (May 1, 1994).

Ogawa et al., "Enhancement of Endotoxicity and Reactivity with Carbocyanine Dye by Sonication of Lipopolysaccharide," *Microbiol. Immunol.*, vol. 28, No. 12, pp. 1313–1323 (1984).

Raetz, "Biochemistry of Endotoxins," *Annual Review of Biochemistry*, vol. 59, pp. 129–170 (1990).

Hunter, "General Microbiology—The Student's Textbook," Mosby Company, p. 19, 34–46.

CYTOTOXICITY OF MSI-344 & MSI-1857 ON BREAST CANCER CELLS

CYTOTOXICITY OF MSI-78 & MSI-1858 ON LEUKEMIA CELLS

CYTOTOXICITY OF MSI-344 & MSI-1857 ON MELANOMA CELLS

Dose-Response Curve of Single IV Administration of MSI-344 and MSI-1857 on Survival Dose-Response Curve of Single IP Administration of MSI-344 and MSI-1857

Effect of MSI-344 and MSI-1857 on Body Weight in Mice Dosed Thrice per Week

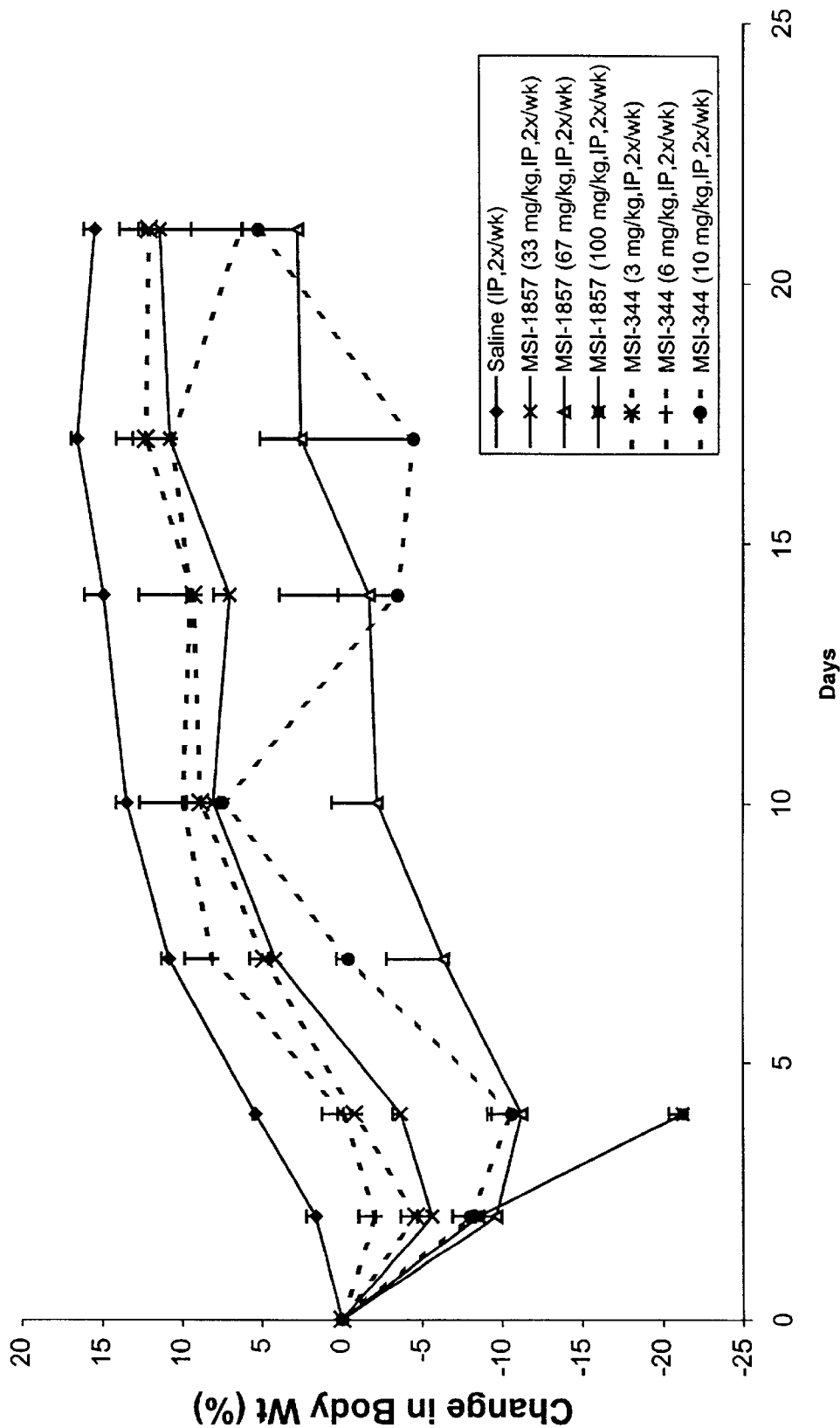

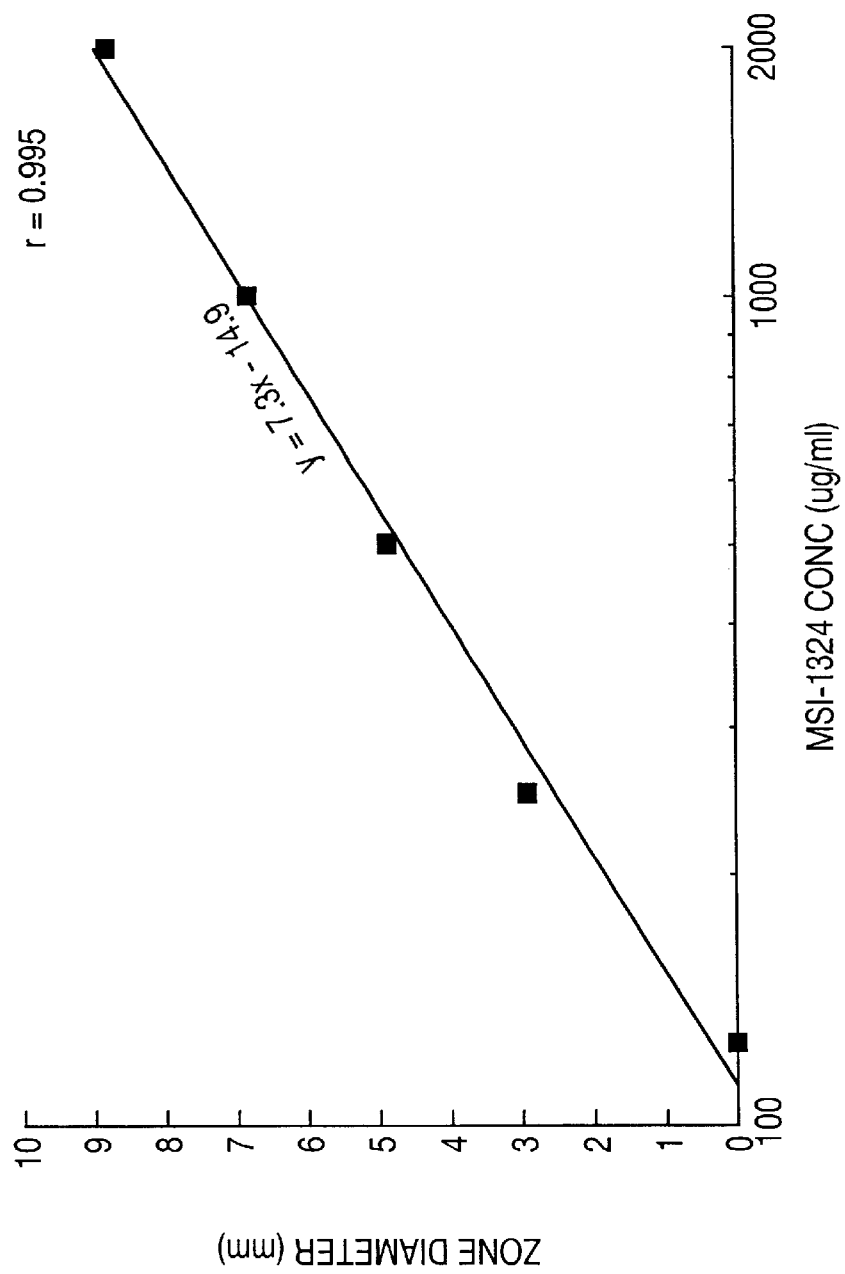
FIG. 15 SINGLE DOSE PHARMACOKINETIC STUDY IN MICE - MSI-1324
RESULTS: ZONE CLEARING STANDARD CURVE

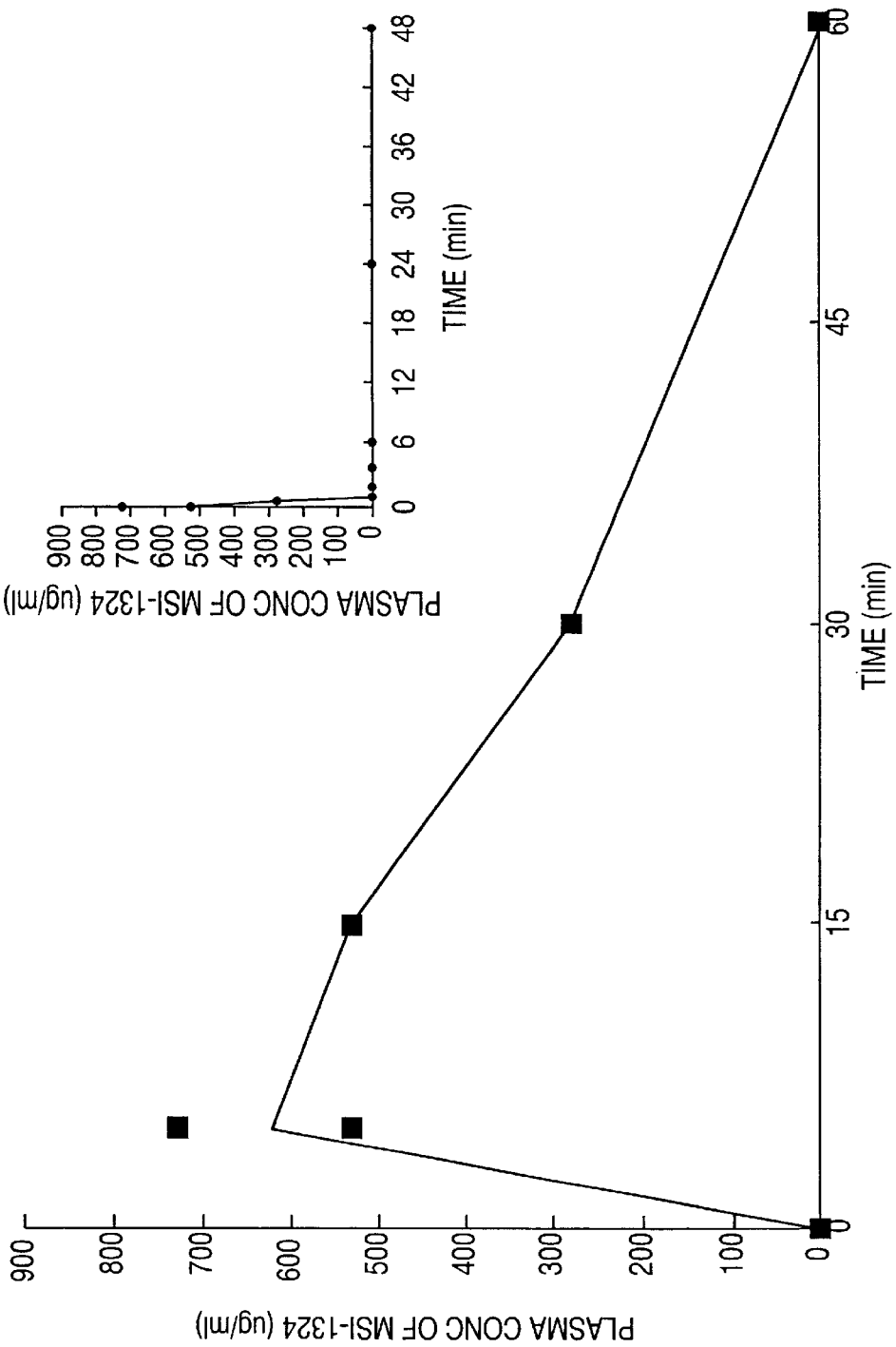

```
                          SEQUENCE LISTING (1) GENERAL INFORMATION:

(iii) NUMBER OF SEQUENCES: 156

(2) INFORMATION FOR SEQ ID NO: 1:

(i) SEQUENCE CHARACTERISTICS:
          (A) LENGTH: 20 amino acids
          (B) TYPE: amino acid
          (D) TOPOLOGY: linear (ii) MOLECULE TYPE: peptide (xi) SEQUENCE DESCRIPTION: SEQ ID NO: 1:

Ala Phe Ser Lys Ala Phe Ser Lys Ala Phe Ser Lys Ala Phe Ser Lys
1               5                  10                  15

Ala Phe Ser Lys
         20

(2) INFORMATION FOR SEQ ID NO: 2:

(i) SEQUENCE CHARACTERISTICS:
          (A) LENGTH: 24 amino acids
          (B) TYPE: amino acid
          (D) TOPOLOGY: linear (ii) MOLECULE TYPE: peptide (xi) SEQUENCE DESCRIPTION: SEQ ID NO: 2:

Ala Phe Ser Lys Ala Phe Ser Lys Ala Phe Ser Lys Ala Phe Ser Lys
1               5                  10                  15

Ala Phe Ser Lys Ala Phe Ser Lys
         20
```

(2) INFORMATION FOR SEQ ID NO: 3:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO: 3:

```
Phe Ser Lys Ala Phe Ser Lys Ala Phe Ser Lys Ala Phe Ser Lys Ala
1               5                   10                  15
```

(2) INFORMATION FOR SEQ ID NO: 4:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 4:

```
Ser Lys Ala Phe Ser Lys Ala Phe Ser Lys Ala Phe Ser Lys Ala Phe
1               5                   10                  15
Ser Lys Ala Phe
                20
```

(2) INFORMATION FOR SEQ ID NO: 5:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO: 5:

```
Lys Ala Phe Ser Lys Ala Phe Ser Lys Ala Phe Ser Lys Ala Phe Ser
1               5                   10                  15
```

(2) INFORMATION FOR SEQ ID NO: 6:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO: 6:

```
Gly Ile Gly Lys Phe Leu His Ser Ala Gly Lys Phe Gly Lys Ala Phe
1               5                   10                  15
Val Gly Glu Ile Met Lys Ser
                20
```

(2) INFORMATION FOR SEQ ID NO: 7:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO: 7:

```
Gly Ile Gly Lys Phe Leu His Ser Ala Lys Lys Phe Gly Lys Ala Phe
1               5                   10                  15
```

Val Gly Glu Ile Met Asn Ser
            20

(2) INFORMATION FOR SEQ ID NO: 8:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO: 8:

Gly Ile Gly Lys Phe Leu His Ser Ala Lys Lys Phe Gly Lys Ala Phe
1               5                   10                  15

Val Gly Glu Ile Met Asn
            20

(2) INFORMATION FOR SEQ ID NO: 9:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO: 9:

Ile Gly Lys Phe Leu His Ser Ala Lys Lys Phe Gly Lys Ala Phe Val
1               5                   10                  15

Gly Glu Ile Met Asn Ser
            20

(2) INFORMATION FOR SEQ ID NO: 10:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 10:

Gly Lys Phe Leu His Ser Ala Lys Lys Phe Gly Lys Ala Phe Val Gly
1               5                   10                  15

Glu Ile Met Asn Ser
            20

(2) INFORMATION FOR SEQ ID NO: 11:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 11:

Lys Phe Leu His Ser Ala Lys Lys Phe Gly Lys Ala Phe Val Gly Glu
1               5                   10                  15

Ile Met Asn Ser
            20

(2) INFORMATION FOR SEQ ID NO: 12:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO: 12:

Gly Met Ala Ser Lys Ala Gly Ala Ile Ala Gly Lys Ile Ala Lys Val
1               5                   10                  15

Ala Leu Lys Ala Leu
            20

(2) INFORMATION FOR SEQ ID NO: 13:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 13:

Gly Trp Ala Ser Lys Ile Gly Gln Thr Leu Gly Lys Ile Ala Lys Val
1               5                   10                  15

Gly Leu Lys Glu Leu Ile Gln Pro Lys
            20                  25

(2) INFORMATION FOR SEQ ID NO: 14:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 14:

Gly Phe Gly Ser Phe Leu Gly Leu Ala Leu Lys Ala Ala Leu Lys Ile
1               5                   10                  15

Gly Ala Asn Ala Leu Gly Gly Ala Pro Gln Gln
            20                  25

(2) INFORMATION FOR SEQ ID NO: 15:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 15:

Gly Leu Ala Ser Phe Leu Gly Lys Ala Leu Lys Ala Gly Leu Lys Ile
1               5                   10                  15

Gly Ala His Leu Leu Gly Gly Ala Pro Gln Gln
            20                  25

(2) INFORMATION FOR SEQ ID NO: 16:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 16:

Gly Leu Ala Ser Leu Leu Gly Lys Ala Leu Lys Ala Gly Leu Lys Ile
1               5                   10                  15

Gly Thr His Phe Leu Gly Gly Ala Pro Gln Gln
            20                  25

(2) INFORMATION FOR SEQ ID NO: 17:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 17:

Gly Leu Ala Ser Leu Leu Gly Lys Ala Leu Lys Ala Thr Leu Lys Ile
1               5                   10                  15

Gly Thr His Phe Leu Gly Gly Ala Pro Gln Gln
            20                  25

(2) INFORMATION FOR SEQ ID NO: 18:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 18:

Gly Phe Ala Ser Phe Leu Gly Lys Ala Leu Lys Ala Ala Leu Lys Ile
1               5                   10                  15

Gly Ala Asn Met Leu Gly Gly Thr Pro Gln Gln
            20                  25

(2) INFORMATION FOR SEQ ID NO: 19:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 19:

Gly Phe Gly Ser Phe Leu Gly Lys Ala Leu Lys Ala Ala Leu Lys Ile
1               5                   10                  15

Gly Ala Asn Ala Leu Gly Gly Ala Pro Gln Gln
            20                  25

(2) INFORMATION FOR SEQ ID NO: 20:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 20:

Gly Phe Gly Ser Phe Leu Gly Lys Ala Leu Lys Ala Ala Leu Lys Ile
1               5                   10                  15

Gly Ala Asn Ala Leu Gly Gly Ser Pro Gln Gln
            20                  25

(2) INFORMATION FOR SEQ ID NO: 21:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 21:

```
Gly Phe Ala Ser Phe Leu Gly Lys Ala Leu Lys Ala Ala Leu Lys Ile
1               5                   10                  15
Gly Ala Asn Leu Leu Gly Gly Thr Pro Gln Gln
            20                  25
```

(2) INFORMATION FOR SEQ ID NO: 22:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 22:

```
Gly Phe Ala Ser Phe Leu Gly Lys Ala Leu Lys Ala Ala Leu Lys Ile
1               5                   10                  15
Gly Ala Asn Ala Leu Gly Gly Ala Pro Gln Gln
            20                  25
```

(2) INFORMATION FOR SEQ ID NO: 23:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 23:

```
Gly Phe Ala Ser Phe Leu Gly Lys Ala Leu Lys Ala Ala Leu Lys Ile
1               5                   10                  15
Gly Ala Asn Met Leu Gly Gly Ala Pro Gln Gln
            20                  25
```

(2) INFORMATION FOR SEQ ID NO: 24:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 24:

```
Gly Phe Gly Ser Phe Leu Gly Lys Ala Leu Lys Ala Ala Leu Lys Ile
1               5                   10                  15
Gly Ala Asn Ala Leu Gly Gly Ser Leu Gln Gln
            20                  25
```

(2) INFORMATION FOR SEQ ID NO: 25:

(i) SEQUENCE CHARACTERISTICS:
        (A) LENGTH: 27 amino acids
        (B) TYPE: amino acid (D) TOPOLOGY: linear (ii) MOLECULE TYPE: peptide (xi) SEQUENCE DESCRIPTION: SEQ ID NO: 25:

Gly Phe Gly Ser Phe Leu Gly Lys Ala Leu Lys Ala Gly Leu Lys Ile
1               5                   10                  15
Gly Thr Asn Phe Leu Gly Gly Ala Pro Gln Gln
            20                  25

(2) INFORMATION FOR SEQ ID NO: 26:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 26:

Gly Leu Ala Ser Leu Leu Gly Lys Ala Leu Lys Ala Ala Leu Lys Ile
1               5                   10                  15
Gly Ala Asn Ala Leu Gly Gly Ser Pro Gln Gln
            20                  25

(2) INFORMATION FOR SEQ ID NO: 27:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 27:

Lys Ile Ala Gly Lys Ile Ala Lys Ile Ala Gly Lys Ile Ala Lys Ile
1               5                   10                  15
Ala Gly Lys Ile Ala
            20

(2) INFORMATION FOR SEQ ID NO: 28:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 28:

Lys Ile Ala Lys Ile Ala Gly Lys Ile Ala Lys Ile Ala Gly Lys Ile
1               5                   10                  15
Ala Lys Ile Ala Gly
            20

(2) INFORMATION FOR SEQ ID NO: 29:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 29:

Lys Ile Ala Gly Lys Ile Gly Lys Ile Ala Gly Lys Ile Gly Lys Ile

```
                1               5                   10                  15
Ala Gly Lys Ile Gly
            20

(2) INFORMATION FOR SEQ ID NO: 30:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 30:

Lys Leu Ala Gly Lys Leu Ala Lys Leu Ala Gly Lys Leu Ala Lys Leu
1               5                   10                  15
Ala Gly Lys Leu Ala
            20

(2) INFORMATION FOR SEQ ID NO: 31:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 31:

Lys Phe Ala Gly Lys Phe Ala Lys Phe Ala Gly Lys Phe Ala Lys Phe
1               5                   10                  15
Ala Gly Lys Phe Ala
            20

(2) INFORMATION FOR SEQ ID NO: 32:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 32:

Lys Ala Leu Ser Lys Ala Leu Lys Ala Leu Ser Lys Ala Leu Lys Ala
1               5                   10                  15
Leu Ser Lys Ala Leu
            20

(2) INFORMATION FOR SEQ ID NO: 33:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 33:

Lys Leu Leu Lys Ala Leu Gly Lys Leu Leu Lys Ala Leu Gly Lys Leu
1               5                   10                  15
Leu Lys Ala Leu Gly
            20

(2) INFORMATION FOR SEQ ID NO: 34:
```

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO: 34:

```
Lys Ala Ile Gly Lys Ala Ile Lys Ala Ile Gly Lys Ala Ile Lys Ala
 1               5                  10                  15
Ile Gly Lys Ala Ile
            20
```

(2) INFORMATION FOR SEQ ID NO: 35:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 35:

```
Gly Ile Ala Lys Ile Ala Lys Gly Ile Ala Lys Ile Ala Lys Gly Ile
 1               5                  10                  15
Ala Lys Ile Ala Lys
            20
```

(2) INFORMATION FOR SEQ ID NO: 36:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 36:

```
Lys Ile Ala Lys Ile Phe Gly Lys Ile Ala Lys Ile Phe Gly Lys Ile
 1               5                  10                  15
Ala Lys Ile Phe Gly
            20
```

(2) INFORMATION FOR SEQ ID NO: 37:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 37:

```
Gly Ile Ala Arg Ile Ala Lys Gly Ile Ala Arg Ile Ala Lys Gly Ile
 1               5                  10                  15
Ala Arg Ile Ala Lys
            20
```

(2) INFORMATION FOR SEQ ID NO: 38:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 38:

Lys Phe Ala Arg Ile Ala Gly Lys Phe Ala Arg Ile Ala Gly Lys Phe
1               5                   10                  15

Ala Arg Ile Ala Gly
            20

(2) INFORMATION FOR SEQ ID NO: 39:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 39:

Gly Phe Ala Lys Ile Ala Lys Gly Phe Ala Lys Ile Ala Lys Gly Phe
1               5                   10                  15

Ala Lys Ile Ala Lys
            20

(2) INFORMATION FOR SEQ ID NO: 40:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(5, 12, 19)
        (D) OTHER INFORMATION: /note= "Xaa is ornithine."

(xi) SEQUENCE DESCRIPTION: SEQ ID NO: 40:

Lys Ile Ala Gly Xaa Ile Ala Lys Ile Ala Gly Xaa Ile Ala Lys Ile
1               5                   10                  15

Ala Gly Xaa Ile Ala
            20

(2) INFORMATION FOR SEQ ID NO: 41:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 41:

Lys Ile Ala Arg Ile Ala Gly Lys Ile Ala Arg Ile Ala Gly Lys Ile
1               5                   10                  15

Ala Arg Ile Ala Gly
            20

(2) INFORMATION FOR SEQ ID NO: 42:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:

(A) NAME/KEY: Modified-site
        (B) LOCATION: one-of(1, 8, 15)
        (D) OTHER INFORMATION: /note= "Xaa is ornithine."

(xi) SEQUENCE DESCRIPTION: SEQ ID NO: 42:

Xaa Ile Ala Gly Lys Ile Ala Xaa Ile Ala Gly Lys Ile Ala Xaa Ile
1               5                  10                  15

Ala Gly Lys Ile Ala
            20

(2) INFORMATION FOR SEQ ID NO: 43:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 43:

Gly Ile Ala Arg Ile Phe Lys Gly Ile Ala Arg Ile Phe Lys Gly Ile
1               5                  10                  15

Ala Arg Ile Phe Lys
            20

(2) INFORMATION FOR SEQ ID NO: 44:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(2, 6, 9, 13, 16, 20)
        (D) OTHER INFORMATION: /note= "Xaa is norleucine."

(xi) SEQUENCE DESCRIPTION: SEQ ID NO: 44:

Lys Xaa Ala Gly Lys Xaa Ala Lys Xaa Ala Gly Lys Xaa Ala Lys Xaa
1               5                  10                  15

Ala Gly Lys Xaa Ala
            20

(2) INFORMATION FOR SEQ ID NO: 45:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(2, 9, 16)
        (D) OTHER INFORMATION: /note= "Xaa is norleucine."

(xi) SEQUENCE DESCRIPTION: SEQ ID NO: 45:

Lys Xaa Ala Gly Lys Ile Ala Lys Xaa Ala Gly Lys Ile Ala Lys Xaa
1               5                  10                  15

Ala Gly Lys Ile Ala
            20

(2) INFORMATION FOR SEQ ID NO: 46:

```
    (i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(6, 13, 20)
        (D) OTHER INFORMATION: /note= "Xaa is norleucine."

(xi) SEQUENCE DESCRIPTION: SEQ ID NO: 46:

Lys Ile Ala Gly Lys Xaa Ala Lys Ile Ala Gly Lys Xaa Ala Lys Ile
1               5                   10                  15

Ala Gly Lys Xaa Ala
            20

(2) INFORMATION FOR SEQ ID NO: 47:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(2, 6, 9, 13, 16, 20)
        (D) OTHER INFORMATION: /note= "Xaa is norvaline."

(xi) SEQUENCE DESCRIPTION: SEQ ID NO: 47:

Lys Xaa Ala Gly Lys Xaa Ala Lys Xaa Ala Gly Lys Xaa Ala Lys Xaa
1               5                   10                  15

Ala Gly Lys Xaa Ala
            20

(2) INFORMATION FOR SEQ ID NO: 48:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(2, 9, 16, 20)
        (D) OTHER INFORMATION: /note= "Xaa is norvaline."

(xi) SEQUENCE DESCRIPTION: SEQ ID NO: 48:

Lys Xaa Ala Gly Lys Ile Ala Lys Xaa Ala Gly Lys Ile Ala Lys Xaa
1               5                   10                  15

Ala Gly Lys Xaa Ala
            20

(2) INFORMATION FOR SEQ ID NO: 49:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 49:

Lys Leu Leu Ser Lys Leu Gly Lys Leu Leu Ser Lys Leu Gly Lys Leu
```

```
                 1               5                  10                 15
Leu Ser Lys Leu Gly
            20

(2) INFORMATION FOR SEQ ID NO: 50:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 50:

Lys Leu Leu Ser Lys Phe Gly Lys Leu Leu Ser Lys Phe Gly Lys Leu
 1               5                  10                 15
Leu Ser Lys Phe Gly
            20

(2) INFORMATION FOR SEQ ID NO: 51:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(6, 13, 20)
        (D) OTHER INFORMATION: /note= "Xaa is norvaline."

(xi) SEQUENCE DESCRIPTION: SEQ ID NO: 51:

Lys Ile Ala Gly Lys Xaa Ala Lys Ile Ala Gly Lys Xaa Ala Lys Ile
 1               5                  10                 15
Ala Gly Lys Xaa Ala
            20

(2) INFORMATION FOR SEQ ID NO: 52:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 52:

His Ile Ala Gly His Ile Ala His Ile Ala Gly His Ile Ala His Ile
 1               5                  10                 15
Ala Gly His Ile Ala
            20

(2) INFORMATION FOR SEQ ID NO: 53:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 53:

Ala Gly Lys Ile Ala Lys Ile Ala Gly Lys Ile Ala Lys Ile Ala Gly
 1               5                  10                 15
```

```
Lys Ile Ala Lys Ile
            20

(2) INFORMATION FOR SEQ ID NO: 54:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 54:

Ile Ala Lys Ile Ala Gly Lys Ile Ala Lys Ile Ala Gly Lys Ile Ala
1               5                   10                  15

Lys Ile Ala Gly Lys
            20

(2) INFORMATION FOR SEQ ID NO: 55:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 55:

Lys Ile Ala Gly Arg Ile Ala Lys Ile Ala Gly Arg Ile Ala Lys Ile
1               5                   10                  15

Ala Gly Arg Ile Ala
            20

(2) INFORMATION FOR SEQ ID NO: 56:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 56:

Arg Ile Ala Gly Arg Ile Ala Arg Ile Ala Gly Arg Ile Ala Arg Ile
1               5                   10                  15

Ala Gly Arg Ile Ala
            20

(2) INFORMATION FOR SEQ ID NO: 57:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 57:

Lys Val Ala Gly Lys Ile Ala Lys Val Ala Gly Lys Ile Ala Lys Val
1               5                   10                  15

Ala Gly Lys Ile Ala
            20

(2) INFORMATION FOR SEQ ID NO: 58:

(i) SEQUENCE CHARACTERISTICS:
```

(A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 58:

Lys Ile Ala Gly Lys Val Ala Lys Ile Ala Gly Lys Val Ala Lys Ile
1               5                   10                  15

Ala Gly Lys Val Ala
            20

(2) INFORMATION FOR SEQ ID NO: 59:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 59:

Ala Lys Ile Ala Gly Lys Ile Ala Lys Ile Ala Gly Lys Ile Ala Lys
1               5                   10                  15

Ile Ala Gly Lys Ile
            20

(2) INFORMATION FOR SEQ ID NO: 60:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(1, 5, 8, 12, 15, 19)
        (D) OTHER INFORMATION: /note= "Xaa is ornithine."

(xi) SEQUENCE DESCRIPTION: SEQ ID NO: 60:

Xaa Ile Ala Gly Xaa Ile Ala Xaa Ile Ala Gly Xaa Ile Ala Xaa Ile
1               5                   10                  15

Ala Gly Xaa Ile Ala
            20

(2) INFORMATION FOR SEQ ID NO: 61:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 61:

Lys Phe Ala Gly Lys Ile Ala Lys Phe Ala Gly Lys Ile Ala Lys Phe
1               5                   10                  15

Ala Gly Lys Ile Ala
            20

(2) INFORMATION FOR SEQ ID NO: 62:

(i) SEQUENCE CHARACTERISTICS:
        (A) LENGTH: 21 amino acids
        (B) TYPE: amino acid (D) TOPOLOGY: linear (ii) MOLECULE TYPE: peptide (xi) SEQUENCE DESCRIPTION: SEQ ID NO: 62:

Lys Ile Ala Gly Lys Phe Ala Lys Ile Ala Gly Lys Phe Ala Lys Ile
1               5                   10                  15

Ala Gly Lys Phe Ala
            20

(2) INFORMATION FOR SEQ ID NO: 63:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(2, 9, 16)
        (D) OTHER INFORMATION: /note= "Xaa is cyclohexylalanine."

(xi) SEQUENCE DESCRIPTION: SEQ ID NO: 63:

Lys Xaa Ala Gly Lys Ile Ala Lys Xaa Ala Gly Lys Ile Ala Lys Xaa
1               5                   10                  15

Ala Gly Lys Ile Ala
            20

(2) INFORMATION FOR SEQ ID NO: 64:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(2, 9, 16)
        (D) OTHER INFORMATION: /note= "Xaa is norleucine."

(xi) SEQUENCE DESCRIPTION: SEQ ID NO: 64:

Lys Xaa Ala Lys Ile Ala Gly Lys Xaa Ala Lys Ile Ala Gly Lys Xaa
1               5                   10                  15

Ala Lys Ile Ala Gly
            20

(2) INFORMATION FOR SEQ ID NO: 65:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 65:

Arg Ile Ala Gly Lys Ile Ala Arg Ile Ala Gly Lys Ile Ala Arg Ile
1               5                   10                  15

Ala Gly Lys Ile Ala
            20

(2) INFORMATION FOR SEQ ID NO: 66:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: one-of(1, 5, 8, 12, 15, 19)
    (D) OTHER INFORMATION: /note= "Xaa is homoarginine."

(xi) SEQUENCE DESCRIPTION: SEQ ID NO: 66:

Xaa Ile Ala Gly Xaa Ile Ala Xaa Ile Ala Gly Xaa Ile Ala Xaa Ile
1               5                   10                  15

Ala Gly Xaa Ile Ala
            20

(2) INFORMATION FOR SEQ ID NO: 67:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(1, 8, 15)
        (D) OTHER INFORMATION: /note= "Xaa is
            p-aminophenylalanine"

(xi) SEQUENCE DESCRIPTION: SEQ ID NO: 67:

Xaa Ile Ala Gly Lys Ile Ala Xaa Ile Ala Gly Lys Ile Ala Xaa Ile
1               5                   10                  15

Ala Gly Lys Ile Ala
            20

(2) INFORMATION FOR SEQ ID NO: 68:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: one-of(5, 12, 19)
        (D) OTHER INFORMATION: /note= "Xaa is
            p-aminophenylalanine."

(xi) SEQUENCE DESCRIPTION: SEQ ID NO: 68:

Lys Ile Ala Gly Xaa Ile Ala Lys Ile Ala Gly Xaa Ile Ala Lys Ile
1               5                   10                  15

Ala Gly Xaa Ile Ala
            20

(2) INFORMATION FOR SEQ ID NO: 69:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 69:

Lys Leu Ala Ser Lys Ala Gly Lys Ile Ala Gly Lys Ile Ala Lys Val
1               5                   10                  15

Ala Leu Lys Ala Leu
            20

(2) INFORMATION FOR SEQ ID NO: 70:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /note= "Xaa is ornithine."

(xi) SEQUENCE DESCRIPTION: SEQ ID NO: 70:

Lys Ile Ala Gly Lys Ile Ala Lys Ile Ala Gly Xaa Ile Ala Lys Ile
1               5                   10                  15

Gly Lys Ile Ala
            20

(2) INFORMATION FOR SEQ ID NO: 71:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

Lys Ile Ala Gly Lys Ile Ala Lys Ile Ala Gly Arg Ile Ala Lys Ile
1               5                   10                  15

Ala Gly Lys Ile Ala
            20

(2) INFORMATION FOR SEQ ID NO: 72:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /note= "Xaa is norleucine."

(xi) SEQUENCE DESCRIPTION: SEQ ID NO: 72:

Lys Ile Ala Gly Lys Ile Ala Lys Ile Ala Gly Xaa Ile Ala Lys Ile
1               5                   10                  15

Ala Gly Lys Ile Ala
            20

(2) INFORMATION FOR SEQ ID NO: 73:

(i) SEQUENCE CHARACTERISTICS:
        (A) LENGTH: 21 amino acids

```
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 12
      (D) OTHER INFORMATION: /note= "Xaa is norvaline."

(xi) SEQUENCE DESCRIPTION: SEQ ID NO: 73:

Lys Ile Ala Gly Lys Ile Ala Lys Ile Ala Gly Xaa Ile Ala Lys Ile
1               5                   10                  15

Ala Gly Lys Ile Ala
            20

(2) INFORMATION FOR SEQ ID NO: 74:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 12
      (D) OTHER INFORMATION: /note= "Xaa is ornithine."

(xi) SEQUENCE DESCRIPTION: SEQ ID NO: 74:

Lys Phe Ala Gly Lys Phe Ala Lys Phe Ala Gly Xaa Phe Ala Lys Phe
1               5                   10                  15

Ala Gly Lys Phe Ala
            20

(2) INFORMATION FOR SEQ ID NO: 75:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 12
      (D) OTHER INFORMATION: /note= "Xaa is ornithine."

(xi) SEQUENCE DESCRIPTION: SEQ ID NO: 75:

Lys Ile Ala Gly Lys Phe Ala Lys Ile Ala Gly Xaa Phe Ala Lys Ile
1               5                   10                  15

Ala Gly Lys Phe Ala
            20

(2) INFORMATION FOR SEQ ID NO: 76:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (ix) FEATURE:
```

(A) NAME/KEY: Modified-site
    (B) LOCATION: one-of(6, 13, 20)
    (D) OTHER INFORMATION: /note= "Xaa is norleucine."

(ix) FEATURE:
    (A) NAME/KEY: Modified-site
    (B) LOCATION: 12
    (D) OTHER INFORMATION: /note= "Xaa is ornithine."

(xi) SEQUENCE DESCRIPTION: SEQ ID NO: 76:

Lys Ile Ala Gly Lys Xaa Ala Lys Ile Ala Gly Xaa Xaa Ala Lys Ile
1               5                  10                  15

Ala Gly Lys Xaa Ala
        20

(2) INFORMATION FOR SEQ ID NO: 77:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 77:

Lys Met Ala Ser Lys Ala Gly Lys Ile Ala Gly Lys Ile Ala Lys Val
1               5                  10                  15

Ala Leu Lys Ala Leu
        20

(2) INFORMATION FOR SEQ ID NO: 78:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 78:

Lys Ile Ala Ser Lys Ala Gly Lys Ile Ala Gly Lys Ile Ala Lys Val
1               5                  10                  15

Ala Leu Lys Ala Leu
        20

(2) INFORMATION FOR SEQ ID NO: 79:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 9
    (D) OTHER INFORMATION: /note= "Xaa is norleucine."

(xi) SEQUENCE DESCRIPTION: SEQ ID NO: 79:

Lys Ile Ala Ser Lys Ala Gly Lys Xaa Ala Gly Lys Ile Ala Lys Val
1               5                  10                  15

Ala Leu Lys Ala Leu
        20

(2) INFORMATION FOR SEQ ID NO: 80:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "Xaa is norleucine."

(xi) SEQUENCE DESCRIPTION: SEQ ID NO: 80:

Lys Leu Ala Ser Lys Ala Gly Lys Xaa Ala Gly Lys Ile Ala Lys Val
1               5                   10                  15

Ala Leu Lys Ala Leu
            20

(2) INFORMATION FOR SEQ ID NO: 81:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /note= "Xaa is norleucine."

(xi) SEQUENCE DESCRIPTION: SEQ ID NO: 81:

Lys Xaa Ala Ser Lys Ala Gly Lys Xaa Ala Gly Lys Ile Ala Lys Val
1               5                   10                  15

Ala Leu Lys Ala Leu
            20

(2) INFORMATION FOR SEQ ID NO: 82:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /note= "Xaa is
            p-aminophenylalanine."

(xi) SEQUENCE DESCRIPTION: SEQ ID NO: 82:

Lys Ile Ala Gly Lys Ile Ala Lys Ile Ala Gly Xaa Ile Ala Lys Ile
1               5                   10                  15

Ala Gly Lys Ile Ala
            20

(2) INFORMATION FOR SEQ ID NO: 83:

(i) SEQUENCE CHARACTERISTICS:
        (A) LENGTH: 21 amino acids
        (B) TYPE: amino acid (C) STRANDEDNESS: single
        (D) TOPOLOGY: linear (ii) MOLECULE TYPE: peptide (xi) SEQUENCE DESCRIPTION: SEQ ID NO: 83:

Lys Ile Ala Gly Ala Ile Ala Lys Ile Ala Gly Lys Ile Ala Lys Ile
1               5                   10                  15

Ala Gly Lys Ile Ala
            20

(2) INFORMATION FOR SEQ ID NO: 84:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 84:

Lys Ile Ala Gly Lys Ile Ala Lys Ile Ala Gly Ala Ile Ala Lys Ile
1               5                   10                  15

Ala Gly Lys Ile Ala
            20

(2) INFORMATION FOR SEQ ID NO: 85:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

Lys Ile Ala Gly Lys Ile Ala Lys Ile Ala Gly Lys Ile Ala Lys Ile
1               5                   10                  15

Ala Gly Ala Ile Ala
            20

(2) INFORMATION FOR SEQ ID NO: 86:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Lys Ile Ala Lys Lys Ile Ala Lys Ile Ala Lys Lys Ile Ala Lys Ile
1               5                   10                  15

Ala Lys Lys Ile Ala
            20

(2) INFORMATION FOR SEQ ID NO: 87:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Lys Phe Ala Lys Lys Phe Ala Lys Phe Ala Lys Lys Phe Ala Lys Phe
1               5                   10                  15

Ala Lys Lys Phe Ala
            20

(2) INFORMATION FOR SEQ ID NO: 88:

(i) SEQUENCE CHARACTERISTICS:
           (A) LENGTH: 21 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 88:

Lys Phe Ala Lys Lys Ile Ala Lys Phe Ala Lys Lys Ile Ala Lys Phe
1               5                   10                  15

Ala Lys Lys Ile Ala
            20

(2) INFORMATION FOR SEQ ID NO: 89:

(i) SEQUENCE CHARACTERISTICS:
           (A) LENGTH: 21 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 89:

Ala Ile Ala Gly Lys Ile Ala Lys Ile Ala Gly Lys Ile Ala Lys Ile
1               5                   10                  15

Ala Gly Lys Ile Ala
            20

(2) INFORMATION FOR SEQ ID NO: 90:

(i) SEQUENCE CHARACTERISTICS:
           (A) LENGTH: 21 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 90:

Lys Ile Ala Gly Lys Ile Ala Ala Ile Ala Gly Lys Ile Ala Lys Ile
1               5                   10                  15

Ala Gly Lys Ile Ala
            20

(2) INFORMATION FOR SEQ ID NO: 91:

(i) SEQUENCE CHARACTERISTICS:
           (A) LENGTH: 21 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 91:

```
Lys Ile Ala Gly Lys Ile Ala Lys Ile Ala Gly Lys Ile Ala Ala Ile
1               5                   10                  15
Ala Gly Lys Ile Ala
            20
```

(2) INFORMATION FOR SEQ ID NO: 92:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

```
Gly Met Ala Ser Lys Ala Gly Lys Ile Ala Gly Lys Ile Ala Lys Val
1               5                   10                  15
Ala Leu Lys Ala Leu
            20
```

(2) INFORMATION FOR SEQ ID NO: 93:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

```
Gly Ile Gly Ala Val Leu Lys Val Leu Thr Thr Gly Leu Pro Ala Leu
1               5                   10                  15
Ile Ser Trp Ile Lys Arg Lys Arg Gln Gln
            20                  25
```

(2) INFORMATION FOR SEQ ID NO: 94:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

```
Leu Lys Lys Leu Lys Lys Leu Leu Lys Leu Leu
1               5                   10
```

(2) INFORMATION FOR SEQ ID NO: 95:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

```
Leu Leu Lys Lys Leu Lys Lys Leu Leu Lys Leu Leu
1               5                   10
```

(2) INFORMATION FOR SEQ ID NO: 96:

(i) SEQUENCE CHARACTERISTICS:
    (A) LENGTH: 13 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 96:

Lys Leu Leu Lys Lys Leu Lys Lys Leu Leu Lys Leu Leu
1               5                   10

(2) INFORMATION FOR SEQ ID NO: 97:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 97:

Lys Lys Leu Leu Lys Lys Leu Lys Lys Leu Leu Lys Leu Leu
1               5                   10

(2) INFORMATION FOR SEQ ID NO: 98:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

Lys Lys Leu Leu Lys Lys Leu Lys Lys Leu Leu Lys Lys Leu Arg Arg
1               5                   10                  15

(2) INFORMATION FOR SEQ ID NO: 99:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 99:

Lys Leu Lys Lys Leu Leu Lys Lys Leu Lys Lys Leu Leu Lys Leu Leu
1               5                   10                  15

(2) INFORMATION FOR SEQ ID NO: 100:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 100:

Leu Lys Lys Leu Leu Lys Lys Leu Lys Lys Leu Leu Lys Lys Asn
1               5                   10                  15

(2) INFORMATION FOR SEQ ID NO: 101:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 15
        (D) OTHER INFORMATION: /note= "Xaa is homoserine."

(xi) SEQUENCE DESCRIPTION: SEQ ID NO: 101:

```
Leu Lys Lys Leu Leu Lys Lys Leu Lys Lys Leu Leu Lys Lys Xaa
1               5                   10                  15
```

(2) INFORMATION FOR SEQ ID NO: 102:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 102:

```
Leu Lys Leu Leu Lys Lys Leu Leu Lys Lys Asn Lys Lys Leu Leu Lys
1               5                   10                  15

Lys Leu
```

(2) INFORMATION FOR SEQ ID NO: 103:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 103:

```
Leu Lys Leu Leu Lys Lys Leu Leu Lys Lys Pro Lys Lys Leu Leu Lys
1               5                   10                  15

Lys Leu
```

(2) INFORMATION FOR SEQ ID NO: 104:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 104:

```
Leu Leu Lys Lys Leu Lys Lys Leu Leu Lys Lys Leu Gln Gly Pro Pro
1               5                   10                  15

Gln Gly Gln Ser Pro Gln
            20
```

(2) INFORMATION FOR SEQ ID NO: 105:

(i) SEQUENCE CHARACTERISTICS:

(A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 105:

Leu Ala Ser Lys Ala Gly Ala Ile Ala Gly Lys Ile Ala Lys Lys Leu
1               5                   10                  15

Leu Lys Lys Leu
            20

(2) INFORMATION FOR SEQ ID NO: 106:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 106:

Leu Lys Lys Leu Lys Lys Leu
1               5

(2) INFORMATION FOR SEQ ID NO: 107:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 107:

Leu Leu Lys Lys Leu Lys Lys Leu
1               5

(2) INFORMATION FOR SEQ ID NO: 108:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 108:

Lys Leu Leu Lys Lys Leu Lys Lys Leu
1               5

(2) INFORMATION FOR SEQ ID NO: 109:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 109:

Lys Lys Leu Leu Lys Lys Leu Lys Lys Leu
1               5                   10

(2) INFORMATION FOR SEQ ID NO: 110:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 110:

```
Leu Lys Lys Leu Leu Lys Lys Leu Lys Lys Leu
1               5                   10
```

(2) INFORMATION FOR SEQ ID NO: 111:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

```
Ala Lys Lys Leu Leu Lys Lys Leu Lys Lys Leu
1               5                   10
```

(2) INFORMATION FOR SEQ ID NO: 112:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 112:

```
Leu Lys Lys Leu Lys Lys Leu Leu Lys Lys Leu
1               5                   10
```

(2) INFORMATION FOR SEQ ID NO: 113:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

```
Leu Leu Lys Lys Leu Lys Lys Leu Leu Lys Lys Leu
1               5                   10
```

(2) INFORMATION FOR SEQ ID NO: 114:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 114:

```
Lys Leu Leu Lys Lys Leu Lys Lys Leu Leu Lys Lys Leu
1               5                   10
```

(2) INFORMATION FOR SEQ ID NO: 115:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 115:

Lys Lys Leu Leu Lys Lys Leu Lys Lys Leu Leu Lys Lys Leu
1               5                   10

(2) INFORMATION FOR SEQ ID NO: 116:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 116:

Leu Lys Lys Leu Leu Lys Lys Leu Lys Lys Leu Leu Lys Lys Leu
1               5                   10                  15

(2) INFORMATION FOR SEQ ID NO: 117:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 117:

Leu Lys Lys Leu Leu Lys Lys Leu Lys Lys Leu Leu Lys Arg
1               5                   10

(2) INFORMATION FOR SEQ ID NO: 118:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 118:

Lys Phe Ala Lys Lys Phe Ala
1               5

(2) INFORMATION FOR SEQ ID NO: 119:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 119:

Lys Ile Ala Lys Lys Ile Ala 1               5

(2) INFORMATION FOR SEQ ID NO: 120:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 120:

Arg Phe Ala Arg Arg Phe Ala
1               5

(2) INFORMATION FOR SEQ ID NO: 121:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 121:

Lys Phe Ala Lys Phe Ala Lys Lys Phe Ala
1               5                   10

(2) INFORMATION FOR SEQ ID NO: 122:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 122:

Lys Lys Phe Ala Lys Phe Ala Lys Lys Phe Ala
1               5                   10

(2) INFORMATION FOR SEQ ID NO: 123:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 123:

Lys Lys Leu Ala Lys Leu Ala Lys Lys Leu Ala
1               5                   10

(2) INFORMATION FOR SEQ ID NO: 124:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 124:

```
Lys Leu Ala Lys Leu Ala Lys Lys Leu Ala
1               5                   10
```

(2) INFORMATION FOR SEQ ID NO: 125:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 125:

```
Lys Phe Ala Lys Lys Phe Ala Lys Phe Ala Lys Lys Phe Ala
1               5                   10
```

(2) INFORMATION FOR SEQ ID NO: 126:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 126:

```
Arg Phe Ala Arg Arg Phe Ala Arg Phe Ala Arg Arg Phe Ala
1               5                   10
```

(2) INFORMATION FOR SEQ ID NO: 127:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 127:

```
Glu Lys Lys Leu Leu Lys Lys Leu Lys Lys Leu
1               5                   10
```

(2) INFORMATION FOR SEQ ID NO: 128:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 128:

```
Lys Lys Lys Leu Leu Lys Lys Leu Lys Lys Leu
1               5                   10
```

(2) INFORMATION FOR SEQ ID NO: 129:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 129:

Lys Leu Lys Lys Lys Phe Leu Lys Lys Leu
1               5                   10

(2) INFORMATION FOR SEQ ID NO: 130:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 130:

Leu Lys Lys Leu Leu Glu Lys Leu Lys Lys Leu
1               5                   10

(2) INFORMATION FOR SEQ ID NO: 131:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 131:

Leu Lys Lys Leu Leu Lys Glu Leu Lys Lys Leu
1               5                   10

(2) INFORMATION FOR SEQ ID NO: 132:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: one-of(1, 2, 5, 8, 9)
        (D) OTHER INFORMATION: /note= "Xaa=ornithine."

(xi) SEQUENCE DESCRIPTION: SEQ ID NO: 132:

Xaa Xaa Leu Leu Xaa Glu Leu Xaa Xaa Leu
1               5                   10

(2) INFORMATION FOR SEQ ID NO: 133:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 133:

Leu Lys Lys Leu Leu Lys Lys Leu Lys Lys Leu Cys
1               5                   10

(2) INFORMATION FOR SEQ ID NO: 134:

(i) SEQUENCE CHARACTERISTICS:
        (A) LENGTH: 10 amino acids
        (B) TYPE: amino acid

```
            (C) STRANDEDNESS: single
            (D) TOPOLOGY: linear (ii) MOLECULE TYPE: peptide (ix) FEATURE:
            (A) NAME/KEY: Modified-site
            (B) LOCATION: one-of(1, 2, 5, 8, 9)
            (D) OTHER INFORMATION: /note= "Xaa=ornithine."

(xi) SEQUENCE DESCRIPTION: SEQ ID NO: 134:

Xaa Xaa Leu Leu Xaa Asp Leu Xaa Xaa Leu
1               5                   10

(2) INFORMATION FOR SEQ ID NO: 135:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 135:

Lys Lys Phe Gly Lys Lys Phe Val Lys Ile Leu Lys Lys
1               5                   10

(2) INFORMATION FOR SEQ ID NO: 136:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 136:

Lys Trp Lys Leu Phe Lys Lys Ile Glu Lys Val
1               5                   10

(2) INFORMATION FOR SEQ ID NO: 137:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 137:

Leu Lys Lys Leu Leu Lys Lys
1               5

(2) INFORMATION FOR SEQ ID NO: 138:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 138:

Leu Lys Lys Leu Leu Lys Leu Leu Lys
1               5
```

(2) INFORMATION FOR SEQ ID NO: 139:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

```
Lys Lys Leu Leu Lys Lys Leu Lys Lys Leu Leu Lys Lys Leu
1               5                   10
```

(2) INFORMATION FOR SEQ ID NO: 140:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: one-of(2, 5, 6, 8, 9)
        (D) OTHER INFORMATION: /note= "Xaa=ornithine."

(xi) SEQUENCE DESCRIPTION: SEQ ID NO: 140:

```
Leu Xaa Leu Leu Xaa Xaa Leu Xaa Xaa Leu
1               5                   10
```

(2) INFORMATION FOR SEQ ID NO: 141:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa=ornithine."

(xi) SEQUENCE DESCRIPTION: SEQ ID NO: 141:

```
Leu Xaa Lys Leu Leu Lys Lys Leu Lys Lys Leu
1               5                   10
```

(2) INFORMATION FOR SEQ ID NO: 142:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: one-of(2, 3, 6, 7, 9, 10)
        (D) OTHER INFORMATION: /note= "Xaa=ornithine."

(xi) SEQUENCE DESCRIPTION: SEQ ID NO: 142:

```
Leu Xaa Xaa Leu Leu Xaa Xaa Leu Xaa Xaa Leu
1               5                   10
```

(2) INFORMATION FOR SEQ ID NO: 143:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: one-of(1, 2, 5, 6, 8, 9)
        (D) OTHER INFORMATION: /note= "Xaa=ornithine."

(xi) SEQUENCE DESCRIPTION: SEQ ID NO: 143:

```
Xaa Xaa Leu Leu Xaa Xaa Leu Xaa Xaa Leu
1               5                   10
```

(2) INFORMATION FOR SEQ ID NO: 144:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: one-of(1, 2, 5, 8, 9)
        (D) OTHER INFORMATION: /note= "Xaa=ornithine."

(xi) SEQUENCE DESCRIPTION: SEQ ID NO: 144:

```
Xaa Xaa Leu Leu Xaa Gln Leu Xaa Xaa Leu
1               5                   10
```

(2) INFORMATION FOR SEQ ID NO: 145:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 145:

```
Arg Leu Leu Arg Arg Leu Arg Arg Leu
1               5
```

(2) INFORMATION FOR SEQ ID NO: 146:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 146:

```
Val Lys Lys Leu Leu Lys Lys Leu Lys Lys Leu
1               5                   10
```

(2) INFORMATION FOR SEQ ID NO: 147:

(i) SEQUENCE CHARACTERISTICS:
        (A) LENGTH: 14 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 147:

Lys Lys Leu Leu Lys Lys Leu Lys Lys Leu Leu Lys Lys Leu
1               5                   10

(2) INFORMATION FOR SEQ ID NO: 148:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 148:

Lys Leu Lys Lys Leu Lys Lys Leu Phe Lys
1               5                   10

(2) INFORMATION FOR SEQ ID NO: 149:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 149:

Gly Ile Lys Lys Phe Leu Lys Lys Ala Gly Lys Phe Gly Lys Ala Phe
1               5                   10                  15

(2) INFORMATION FOR SEQ ID NO: 150:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 150:

Ile Ala Gly Ala Ile Ala Lys Ile Ala Gly Lys Ile Ala Lys Ile Ala
1               5                   10                  15

Gly Ala Ile Ala
            20

(2) INFORMATION FOR SEQ ID NO: 151:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 151:

Leu Lys Lys Leu Leu Lys Glu Leu Leu Lys Leu
1               5                   10

(2) INFORMATION FOR SEQ ID NO: 152:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 152:

```
Lys Val Ala Leu Lys Ala Leu Lys Lys Val Ala Leu Lys Ala Leu Lys
1               5                   10                  15

Val Ala Leu Lys Ala Leu
            20
```

(2) INFORMATION FOR SEQ ID NO: 153:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 153:

```
Lys Ile Ala Lys Lys Ile Ala Lys Ile Ala Lys Lys Ile Ala
1               5                   10
```

(2) INFORMATION FOR SEQ ID NO: 154:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 154:

```
Gly Ile Gly Lys Phe Leu Lys Lys Ala Lys Lys Phe Gly Lys Ala Phe
1               5                   10                  15

Val Lys Ile Leu Lys Lys
            20
```

(2) INFORMATION FOR SEQ ID NO: 155:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 155:

```
Gly Ile Gly Lys Phe Leu Lys Lys Ala Lys Lys Phe Gly Lys Ala Phe
1               5                   10                  15

Val Lys Ile Met Lys Lys
            20
```

(2) INFORMATION FOR SEQ ID NO: 156:

(i) SEQUENCE CHARACTERISTICS:
        (A) LENGTH: 26 amino acids
        (B) TYPE: amino acid
        (C) STRANDEDNESS: single

```
        (D) TOPOLOGY: linear (ii) MOLECULE TYPE: peptide (xi) SEQUENCE DESCRIPTION: SEQ ID NO: 156:

Lys Ala Lys Leu Phe Ala Lys Ala Gly Ala Gly Ala Val Leu Lys Ala
1               5                   10                  15

Leu Lys Lys Gly Leu Lys Ala Leu Ile Lys
            20              25
```

BIOLOGICALLY ACTIVE PEPTIDES WITH REDUCED TOXICITY IN ANIMALS AND A METHOD FOR PREPARING SAME

RELATED APPLICATION DATA

This application is a continuation-in-part of U.S. patent application Ser. No. 08/893,006 filed Jul. 15, 1997, now abandoned, which is a continuation-in-part of U.S. patent application Ser. No. 08/465,330 filed Jun. 5, 1995, now abandoned, which is a divisional of U.S. patent application Ser. No. 08/184,462 filed Jan. 18, 1994, now abandoned, which is a continuation-in-part of U.S. patent application Ser. No. 07/891,201 filed Jun. 1, 1992, now abandoned. Each of these U.S. patents and applications is entirely incorporated herein by reference.

BACKGROUND AND SUMMARY OF THE INVENTION

This invention relates to biologically active peptides. More particularly, this invention relates to biologically active peptides with reduced toxicity. Further, this invention relates to a method of modifying biologically active peptides, that are either N-terminally (amino-terminal) substituted or unsubstituted, to reduce their toxicity in animals.

In accordance with an aspect of the present invention, there is provided an unsubstituted biologically active peptide or protein. In another aspect, there is provided a N-terminal substituted peptide or protein having the formula:

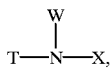

wherein X is a biologically active peptide or protein, and N is a nitrogen atom. The peptide or protein is preferably an ion channel-forming peptide or protein. T is a lipophilic moiety, and W is another T group or hydrogen.

The term "lipophilic," as used herein, means that the lipophilic moiety enhances the interaction of the peptide or protein with a lipid membrane, such as, for example, a cell membrane.

Lipophilic moieties which may be employed, include, but are not limited to, any moiety which may be placed on the N-terminal of the peptide through a condensation reaction with nitrogen. The lipophilic moiety T may be, for example, a carboxylic acid, a phosphoric acid, preferably an alkylphosphoric acid, a phosphonic acid, preferably an alkylphosphonic acid, a sulfonic acid, preferably an alkylsulfonic acid, or an alkyl group. Preferably T is:

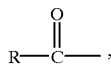

wherein R is a hydrocarbon having at least two and no more than 16 carbon atoms.

In one embodiment, R is an alkyl group. The alkyl group may be a straight chain or branched chain alkyl group, or a cycloalkyl group. For example, R may be $CH_3(CH_2)_n-$, wherein n is from 1 to 14. Preferably, n is from 3 to 12, more preferably from 4 to 11, still more preferably from 6 to 11, and most preferably n is 6, whereby T is an octanoyl group.

In another embodiment, R is an aromatic (including phenyl and naphthyl), or an alkyl aromatic group. For example, R may be

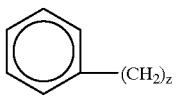

wherein z is from 0 to 6. Preferably, z is 1 or 2.

In another embodiment, R is

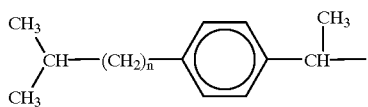

wherein n is from 1 to 5. Preferably n is 1, whereby R is an ibuprofyl group.

In yet another embodiment, T is:

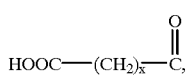

wherein x is from 1 to 14. Preferably, x is 2, and T is a succinyl group.

In another embodiment, T is:

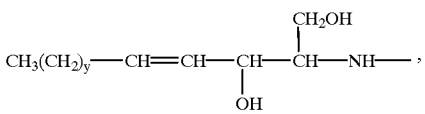

wherein y is from 1 to 14. Preferably, y is 12, whereby T is a sphingosine group.

In yet another embodiment T is

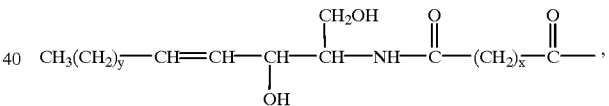

wherein x and y are hereinabove described. Preferably, x is 2, and y is 12.

In one embodiment, W is hydrogen.

Applicant has found that when biologically active peptides have substitutions at the N-terminal such as those hereinabove described, such peptides have increased biological activity against target cells, viruses, and virally-infected cells, as compared with unsubstituted peptides or peptides substituted at the N-terminal with an acetyl group. Applicant also has found that the N-terminal substitutions hereinabove described significantly increase the biological activity of "short" peptides, i.e., peptides having no more than 14 amino acid residues.

In another embodiment of this invention the biologically active peptides are not N-terminally substituted and have broad spectrum anti-tumor and anti-microbial activity.

As hereinabove stated, the biologically active peptides or proteins of the present invention are preferably ion channel-forming peptides. An ion channel-forming peptide or protein or ionophore is a peptide or protein which increases the permeability for ions across a natural or synthetic lipid membrane. B. Christensen, et al., *PNAS* Vol. 85, pgs. 5072–5076 (July 1988) describes a methodology which indicates whether or not a peptide or protein has ion channel-forming properties and is therefore an ionophore. As used herein, an ion channel-forming peptide or ion channel-forming protein is a peptide or protein which has ion channel-forming properties as determined by the method of Christensen, et al. This Christensen article is entirely incorporated herein by reference.

An amphiphilic peptide or protein is a peptide or protein which includes both hydrophobic and hydrophilic peptide or protein regions.

The ion channel-forming peptides employed in the present invention are generally water soluble to a concentration of at least 20 mg/ml at neutral pH in water. In addition, the structure of such peptides provides for flexibility of the peptide molecule. Such peptides are capable of forming an alphahelical structure. When the peptide is placed in water, it does not assume an amphiphilic structure. When the peptide encounters an oily surface or membrane, the peptide chain folds upon itself into a rodlike structure.

In general, such peptides have at least 7 amino acids, and in many cases have at least 20 amino acids. In most cases, such peptides do not have in excess of 40 amino acids.

The peptides and/or analogues or derivatives thereof may be administered to a host, for example a human or non-human animal, in an amount effective to inhibit growth of a target cell, virus, or virally-infected cell. Thus, for example, the peptides and/or analogues or derivatives thereof may be used as anti-microbial agents, anti-viral agents, anti-bacterial agents, anti-tumor agents, anti-parasitic agents, and spermicides, as well as agents exhibiting other bioactive functions.

The term "anti-microbial" as used herein means that the peptides or proteins of the present invention inhibit, prevent, or destroy the growth or proliferation of microbes, such as bacteria, fungi, viruses, or the like.

The term "anti-bacterial" as used herein means that the peptides or proteins employed in the present invention produce effects adverse to the normal biological functions of bacteria, including death, destruction, or prevention of the growth or proliferation of the bacteria when contacted with the peptides or proteins.

The term "antibiotic" as used herein means that the peptides or proteins employed in the present invention produce effects adverse to the normal biological functions of the non-host cell, tissue, or organism, including death, destruction, or prevention of the growth or proliferation of the non-host cell, tissue, or organism when contacted with the peptides or proteins.

The term "spermicidal" as used herein means that the peptides or proteins employed in the present invention inhibit, prevent, or destroy the motility of sperm.

The term "anti-fungal" as used herein means that the peptides or proteins employed in the present invention inhibit, prevent, or destroy the growth or proliferation of fungi.

The term "anti-viral" as used herein means that the peptides or proteins employed in the present invention inhibit, prevent, or destroy the growth or proliferation of viruses, or of virally-infected cells.

The term "anti-tumor" as used herein means that the peptides or proteins inhibit the growth of or destroy tumors, including cancerous tumors.

The term "anti-parasitic" as used herein means that the peptides or proteins employed in the present invention inhibit, prevent, or destroy the growth or proliferation of parasites.

The peptides or proteins of the present invention have a broad range of potent anti-tumor and antibiotic activity against a plurality of tumor types and microorganisms, including gram-positive and gram-negative bacteria, fungi, protozoa, and the like, as well as parasites. The peptides or proteins of the present invention allow a method for treating or controlling tumor growth and microbial infection caused by organisms which are sensitive to the peptides or proteins. Such treatment may comprise administering to a host organism or tissue susceptible to or affiliated with a microbial infection an anti-tumor or anti-microbial amount of at least one of the peptides or proteins.

In another embodiment of this invention, methods are provided for reducing the toxicity of unmodified peptides or of N-terminally modified peptides in a host without reducing the anti-tumor or anti-microbial activity of the peptides. This method includes forming a methane sulfonate derivative or analogue of an unsubstituted peptides or N-terminal substituted peptide having the formula:

wherein X is a biologically active peptide or protein, the peptide being an ion channel-forming peptide or protein, T is a lipophilic moiety or hydrogen. The anti-tumor or anti-microbial activity of the methane sulfonate derivative or analogue of the unsubstituted or N-terminal substituted peptide is not reduced or is not significantly reduced as compared to the corresponding peptide not derivatized with a methane sulfonate group. The phrase "not significantly reduced," as used in this application, means that the methane sulfonate derivatives or analogues retain anti-tumor or anti-microbial activity of the underivatized compounds. Preferably, the methane sulfonate derivatives or analogues retain at least 50%, and preferably 75% or more, of the anti-tumor or anti-microbial activity of the underivatized compounds.

In one embodiment of the invention, the methane sulfonate derivative can be formed by suspending a free base of the unsubstituted or N-terminal substituted peptide in water, and then mixing the suspended peptide and at least 0.5 equivalents of a sodium bisulfite-formaldehyde complex (or other suitable bisulfite-formaldehyde complex) for each free amino group in the peptide. This reaction proceeds for a period of 10 minutes or more to produce the methane sulfonate derivative or analogue of the peptide.

The amount of the bisulfite-formaldehyde complex can be varied without departing from the invention. Preferably, the suspended free base is mixed with 0.5 to 10 equivalents of the bisulfite-formaldehyde complex for each free amino group in the peptide. The use of 1 to 5 equivalents is preferred, and 1.1 to 3 equivalents is particularly preferred.

In the process according to this embodiment of the invention, the mixing period also can be varied widely. Preferably the peptide free base and complex are mixed for a period of 10 minutes to 2 hours, or 10 minutes to 1 hour. A mixing period in the range of from 15 minutes to 30 minutes is particularly preferred.

The starting free base of the unsubstituted peptide or N-terminal substituted peptide can be prepared by neutralizing a salt of the peptide. This neutralization can take place by treating the salt with a base solution, such as a sodium carbonate solution. After neutralization, the free base peptide, which may precipitate, can be isolated prior to suspending it in the water.

After the reaction procedure is completed, the methane sulfonate derivative or analogue of the peptide product can be recovered, e.g., by filtering. Additionally, this product can be lyophilized, if desired.

One method according to this embodiment of the invention can be summarized by the reaction equation provided below:

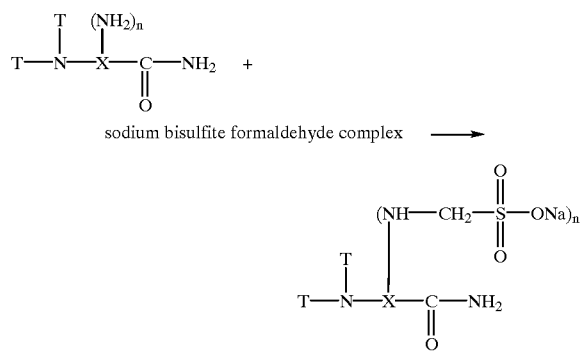

sodium bisulfite formaldehyde complex ⟶ wherein X is a biologically active peptide or protein, N is a nitrogen atom and T is a lipophilic moiety or hydrogen. The peptide or protein is preferably an ion channel-forming peptide or protein.

In another embodiment or the invention the methane sulfonate derivative is formed by mixing the peptide salt with 12.5 equivalents of 30% formaldehyde solution and 6.25 equivalents of 1M sodium bicarbonate solution for each amino group in the peptide. The adduct of the peptide with formaldehyde precipitates and can be collected by centrifugation of filtration. The sodium methane sulfonate derivative is then formed by mixing the formaldehyde adduct with sodium metabisulfite.

The methane sulfonate analogue of the peptide is shown to have reduced toxicity in vivo, but retains its anti-tumor and anti-microbial activity.

Because of the antibiotic, anti-microbial, anti-viral, and anti-bacterial properties of the peptides or proteins, they may also be used as preservatives, sterilants, or disinfectants of materials susceptible to microbial or viral contamination.

The peptide or proteins and/or derivatives or analogues thereof may be administered in combination with a non-toxic pharmaceutical carrier or vehicle such as a filler, a non-toxic buffer, or a physiological saline solution. Such pharmaceutical compositions may be used topically or systemically and may be in any suitable form such as a liquid, solid, semi-solid, injectable solution, tablet, ointment, lotion, paste, capsule, or the like. The peptide or protein compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptides or proteins of the present invention may be administered to a host, in particular a human or non-human animal, in an effective antibiotic and/or anti-tumor and/or anti-fungal and/or anti-viral and/or anti-microbial and/or anti-bacterial and/or anti-parasitic and/or spermicidal amount.

Depending on the use, a composition in accordance with the invention will contain an effective anti-microbial amount and/or an effective spermicidal amount and/or an effective anti-fungal amount and/or an effective anti-viral amount and/or an effective anti-tumor amount and/or an effective anti-parasitic amount and/or an effective antibiotic amount of one or more of the peptides or proteins of the present invention which have such activity. The peptides or proteins may be administered by direct application of the peptides or proteins to the target cell, virus, or virally-infected cell, or indirectly applied through systemic administration.

The peptides or proteins of the present invention may also be employed in promoting or stimulating healing of a wound in a host.

The term "wound healing" as used herein includes various aspects of the wound healing process. These aspects include, but are not limited to, increased contraction of the wound, increased deposition of connective tissue, as evidenced by, for example, increased deposition of collagen in the wound, and increased tensile strength of the wound, i.e., the peptides or proteins increase wound breaking strength. The peptides or proteins of the present invention may also be employed so as to reverse the inhibition of wound healing caused by conditions which depress or compromise the immune system.

The peptides or proteins of the present invention may be used in the treatment of external burns and to treat and/or prevent skin and burn infections. In particular, the peptides or proteins may be used to treat skin and burn infections caused by organisms such as, but not limited to, *P. aeruginosa* and *S. aureus*.

The peptides or proteins are also useful in the prevention or treatment of eye infections. Such infections may be caused by bacteria such as, but not limited to, *P. aeruginosa*, *S. aureus*, and *N. gonorrhoeae*, by fungi such as, but not limited to, *C. albicans* and *A. fumigatus*, by parasites such as, but not limited to, *A. castellani*, or by viruses.

The peptides or proteins may also be effective in killing cysts, spores, or trophozoites of infection-causing organisms. Such organisms include, but are not limited to Acanthamoeba, which form trophozoites or cysts, *C. albicans*, which form spores, and *A. fumigatus*, which also form spores.

The peptides or proteins of the present invention may also be employed in the treatment of tumors. In general, they are active against tumors that arise in tissues and organs such as, but not limited to, breast, lung, colon, rectum, cervix, ovaries prostate, stomach, as well as melanoma and leukemias. More specifically, they are active against non-small cell lung carcinomas and adenocarcinomas of, for example, the breast, cervix, prostate, lung, colon, rectum, stomach, and ovaries. In addition, the peptides and proteins of the present invention are active against tumors that are resistant to other anti-tumor agents. A significant reason for resistance, the removal of anti-tumor agents by the efflux pump, is not believed to apply to the peptides and proteins of the present invention which are believed to function via the unique mechanism of forming ion channels.

The peptides or proteins may also be administered to plants in an effective anti-microbial or anti-viral or anti-parasitic amount to prevent or treat microbial, viral, or parasitic contamination thereof.

The peptides or proteins of the present invention may also be employed in the treatment of serious lung infections. In particular, the peptides or proteins may be used to treat lung infections caused by organisms such as, but not limited to, *P. aeruginosa* in cystic fibrosis patients. In general, in the treatment of such infections, the peptides or proteins are administered to a subject in need of treatment by an inhalation procedure. For example, the active peptide or protein ingredient can be delivered by inhalation using either a nebulizer, metered dose inhaler (MDI), or a dry powder inhaler (DPI).

In employing such compositions by inhalation, the active peptide or protein is present in the following amounts: for a nebulizer, a solution of between 5 and 200 mg/ml; for MDI or DPI, an amount between 0.5 and 45 mg.

The peptides or proteins also may be administered to a subject for treating sepsis, septic shock, and other related ailments, in that such peptides neutralize bacterial endotoxins. In general, the peptides or proteins are positively charged, while, in general, the bacterial endotoxins are negatively charged. The peptides or proteins are particularly useful in that such compounds neutralize bacterial endotoxins without neutralizing essential proteins in plasma (such as heparin, for example).

"Treat," "treated," or "treating," as used in this application, may mean complete elimination of a disease, ailment, or symptoms, or it may mean reducing, suppressing, or ameliorating the severity of the disease, ailment, or symptoms.

The peptides or proteins, when used in topical compositions, are generally present in an amount of at least 0.1%, by weight. In most cases, it is not necessary to employ the peptide in an amount greater than 2.0%, by weight.

In employing such compositions systemically (intramuscular, intravenous, intraperitoneal), the active peptide or protein is present in an amount to achieve a serum level of the peptide of at least about 5 μg/ml. In general, the serum level of peptide or protein need not exceed 500 μg/ml. A preferred serum level is about 100 μg/ml. Such serum levels may be achieved by incorporating the peptide or protein in a composition to be administered systemically at a dose of from 1 to about 10 mg/kg. In general, the peptide(s) or protein(s) need not be administered at a dose exceeding 100 mg/kg.

The peptides or proteins may be produced by known techniques and obtained in substantially pure form. For example, the peptides may be synthesized on an automatic peptide synthesizer. *Journal of the American Chemical Society*, Vol. 85, pgs. 2149–54 (1963) (which article is entirely incorporated herein by reference). It also is possible to produce such peptides or proteins by genetic engineering techniques. The codons encoding specific amino acids are known to those skilled in the art, and therefore, DNA encoding the peptides may be constructed by appropriate techniques, and one may clone such DNA into an appropriate expression vehicle (e.g., a plasmid) which is transfected into an appropriate organism for expression of the peptide or protein.

In one embodiment of the invention, upon production or synthesis of the peptide or protein, the N-terminal (NH$_2$ or amino terminal) of the peptide is reacted such that the lipophilic moiety is attached to the N-terminal of the peptide. For example, the reaction may be a condensation reaction with an amine. When the lipophilic moiety T is

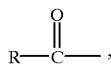

the N-terminal is reacted with a carboxylic acid of the formula R—COOH, wherein R is a hydrocarbon having at least 2 carbon atoms. The reaction may be carried out in the presence of a coupling agent, such as, for example, DCC, or DIC, and HOBT, or in the presence of an acid chloride. Such a reaction results in the formation of an N-terminal substituted peptide or protein having the structural formula hereinabove described.

In one embodiment, X is a peptide which is a basic (positively charged) polypeptide having at least sixteen amino acids, wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acid, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Pro, Val, Trp, Tyr, norleucine (Nle), norvaline (Nva), and cyclohexylalanine (Cha). The neutral hydrophilic amino acids may be selected from the class consisting of Asn, Gln, Ser, Thr, and homoserine (Hse). The basic hydrophilic amino acids may be selected from the class consisting of Lys, Arg, His, Orn, homoarginone (Har), 2,4-diaminobutyric acid (Dbu), and p-aminophenylalanine.

Each of the groups of four amino acids may be of the sequence ABCD, BCDA, CDAB, or DABC, wherein A and B are each hydrophobic amino acids and may be the same or different, one of C, or D is a basic hydrophilic amino acid, and the other of C or D is a basic or neutral hydrophilic amino acid and may be the same or different. In one embodiment, the polypeptide chain may comprise 5 or 6 groups of this sequence. In each group, each of A, B, C, and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary, provided that in each group of the at least four groups of amino acids there are two hydrophobic and two hydrophilic amino acids as hereinabove noted.

Thus, the biologically active polypeptide may comprise a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic amino acids, one of C or D is a basic hydrophilic amino acid, and the other of C or D is basic or neutral hydrophilic amino acid. The resulting polypeptide chain, therefore, may have one of the following sequences:

$(X_1)_a(A\text{-}B\text{-}C\text{-}D)_n(Y_1)_b$
$(X_2)_a(B\text{-}C\text{-}D\text{-}A)_n(Y_2)_b$
$(X_3)_a(C\text{-}D\text{-}A\text{-}B)_n(Y_3)_b$
$(X_4)_a(D\text{-}A\text{-}B\text{-}C)_n(Y_4)_b$ wherein $X_1$ is D or C-D- or B-C-D-;
$Y_1$ is -A or -A-B or -A-B-C;
$X_2$ is A-, D-A- or C-D-A-;
$Y_2$ is -B, -B-C or B-C-D;
$X_3$ is B-, A-B-, D-A-B-;
$Y_3$ is -C, -C-D, -C-D-A;
$X_4$ is C-, B-C-, A-B-C-;
$Y_4$ is -D, -D-A, -D-A-B;
a is 0 or 1; b is 0 or 1; and n is at least 4.

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and does not adversely affect the folding characteristics of the chain to that which is significantly different from one in which the hereinabove noted groups of four amino acids are not spaced from each other.

As representative examples of such peptides, the following may be mentioned:

I Ala-Phe-Ser-Lys-Ala-Phe-Ser-Lys-Ala-Phe-Ser-Lys-Ala-Phe-Ser-Lys (SEQ ID NO:1)
II Ala-Phe-Ser-Lys-Ala-Phe-Ser-Lys-Ala-Phe-Ser-Lys-Ala-Phe-Ser-Lys-Ala-Phe-Ser-Lys. (SEQ ID NO:2)
III Phe-Ser-Lys-Ala-Phe-Ser-Lys-Ala-Phe-Ser-Lys-Ala-Phe-Ser-Lys-Ala- (SEQ ID NO:3)
IV Ser-Lys-Ala-Phe-Ser-Lys-Ala-Phe-Ser-Lys-Ala-Phe-Ser-Lys-Ala-Phe-Ser-Lys-Ala-Phe- (SEQ ID NO:4)
V Lys-Ala-Phe-Ser-Lys-Ala-Phe-Ser-Lys-Ala-Phe-Ser-Lys-Ala-Phe-Ser (SEQ ID NO:5)

The peptide may have amino acids extending from either end of the chain. For example, the chains may have a Ser-Lys sequence before the "Ala" end, and/or an Ala-Phe sequence after the "Lys" end. Other amino acid sequences may also be attached to the "Ala" and/or the "Lys" end.

Similarly, in any polypeptide chain having at least four groups of amino acids of the sequence as described above, the chain may have, for example, a C-D sequence before the first A-B-C-D group. Also other amino acid sequences may be attached to the "A" and/or the "D" end of one of these polypeptide chains. Also, there may be amino acids in the chain which space one or more groups of the hereinabove noted four amino acids from each other.

In accordance with another embodiment, X is a magainin peptide.

A magainin peptide is either a magainin such as magainin I, II, or III, or an analogue or derivative thereof. The magainin peptides preferably include the following basic peptide structure $X_{12}$:

$R_{11}$-$R_{11}$-$R_{12}$-$R_{13}$-$R_{11}$-$R_{14}$-$R_{12}$-$R_{11}$-$R_{14}$-$R_{12}$-$R_{11}$-$R_{11}$-$R_{11}$-$R_{14a}$-$(R_{15})_n$-$R_{14a}$-$R_{14}$ wherein $R_{11}$ is a hydrophobic amino acid; $R_{12}$ is a basic hydrophilic amino acid; $R_{13}$ is a hydrophobic, neutral hydrophilic, or basic hydrophilic amino acid; $R_{14}$ and $R_{14a}$ are hydrophobic or basic hydrophilic amino acids; $R_{15}$ is glutamic acid or aspartic acid; and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

Thus, for example, a magainin peptide may include the following structure:

-$Y_{12}$-$X_{12}$- where $X_{12}$ is the hereinabove described basic peptide structure, and $Y_{12}$ is
(i) $R_{12}$
(ii) $R_{14a}$-$R_{12}$
(iii) $R_{11}$-$R_{14a}$-$R_{12}$
(iv) $R_{14}$-$R_{11}$-$R_{14a}$-$R_{12}$ where $R_{11}$, $R_{12}$, $R_{14}$, and $R_{14a}$ are as previously defined.

A magainin peptide may also have the following structure:

-$X_{12}$-$Z_{12}$- wherein $X_{12}$ is as previously defined and $Z_{12}$ is:
(i) $R_{16}$, where $R_{16}$ is a basic hydrophilic amino acid or asparagine or glutamine; or
(ii) $R_{16}$-$R_{17}$, where $R_{17}$ is a neutral hydrophilic amino acid, a hydrophobic amino acid, or a basic hydrophilic amino acid.

Preferably, $R_{17}$ is a basic hydrophilic amino acid.

A magainin peptide may also have the following structure:

$(Y_{12})_a$-$X_{12}$-$Z_{12})_b$ where $X_{12}$, $Y_{12}$, and $Z_{12}$ are as previously defined, a is 0 or 1, and b is 0 or 1.

As representative examples of such peptides, the following may be mentioned:

I Gly-Ile-Gly-Lys-Phe-Leu-Lys-Lys-Ala-Lys-Lys-Phe-Gly-Lys-Ala-Phe-Val-Lys-Ile-Leu-Lys-Lys (SEQ ID NO: 154) (OH) or (NH$_2$)
II Gly-Ile-Gly-Lys-Phe-Leu-Lys-Lys-Ala-Lys-Lys-Phe-Gly-Lys-Ala-Phe-Val-Lys-Ile-Met-Lys-Lys (SEQ ID NO: 155)(OH) or (NH$_2$)

The magainin peptides may also include the following basic peptide structure $X_{13}$:

$R_{14}$-$R_{11}$-$R_{14a}$-$R_{12}$-$R_{11}$-$R_{11}$-$R_{12}$-$R_{13}$-$R_{11}$-$R_{14}$-$R_{12}$-$R_{11}$-$R_{11}$-$R_{12}$, wherein $R_{11}$,$R_{12}$,$R_{13}$,$R_{14}$, and $R_{14}$a are amino acids as hereinabove described.

The magainin peptide may also include the following structure: -$X_{13}$-$Z_{13}$-, wherein $X_{13}$ is the hereinabove described basic peptide structure and $Z_{13}$ is $(R_{11})_n$-$(R_{11})_n$-$(R_{11})_n$-$(R_{14a})_n$-$(R_{15})_n$-$(R_{14a})_n$-$(R_{14})_n$-$(R_{16})_n$-$(R_{17})_n$, wherein $R_{11}$, $R_{14}$, $R_{14a}$, $R_{15}$ $R_{16}$, and $R_{17}$ are as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequences as given in the accompanying sequence listing, as well as appropriate analogues and derivatives thereof:

(a) (SEQ ID NO:6) (OH) or (NH$_2$)
    (Magainin I)
(b) (SEQ ID NO:7) (OH) or (NH$_2$)
    (Magainin II)
(c) (SEQ ID NO:8) (OH) or (NH$_2$)
    (Magainin III)

The following are examples of peptide derivatives or analogs of the basic structure:

(d) (SEQ ID NO:9)  (OH) or (NH$_2$)
(e) (SEQ ID NO:10) (OH) or (NH$_2$)
(f) (SEQ ID NO:11) (OH) or (NH$_2$)

Magainin peptides are described in *Proc. Natl. Acad Sci.* Vol. 84 pp. 5449–53 (Aug. 87), which article is entirely incorporated herein by reference. The term "magainin peptides" as used herein refers to the basic magainin structure as well as derivatives and analogs thereof, including, but not limited to, the representative derivatives or analogs.

In accordance with a further embodiment, X may be a PGLa peptide or an XPF peptide. A PGLa peptide is either PGLa or an analogue or derivative thereof. The PGLa peptides preferably include the following basic peptide structure $X_{14}$:

$R_{11}$-$R_{17}$-$R_{12}$-$R_{11}$-$R_{14}$-$R_{14}$-$R_{14}$-$R_{12}$-$R_{11}$-$R_{11}$-$R_{12}$-$R_{11}$-$R_{11}$-$R_{12}$, where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl ends.

Thus, for example, a PGLa peptide may have the following structure:

-$Y_{14}$-$X_{14}$- where $X_{14}$ is as previously defined and
$Y_{14}$ is
(i) $R_{11}$; or
(ii) $R_{14}$-$R_{11}$,
where $R_{11}$ and $R_{14}$ are as previously defined.

For example, a PGLa peptide may also have the following structure:

-$X_{14}$-$Z_{14}$- where $X_{14}$ is as previously defined; and $Z_{14}$ is:
(i) $R_{11}$; or
(ii) $R_{11}$-$R_{11}$,
where $R_{11}$ is as previously defined.

A PGLa peptide may also have the following structure:

$(Y_{14})_a$-$X_{14}$-$(Z_{14})_b$ where $X_{14}$, $Y_{14}$, and $Z_{14}$ are as previously defined, a is 0 or 1, and b is 0 or 1.

An XPF peptide is either XPF or an analogue or derivative thereof. The XPF peptides preferably include the following basic peptide structure $X_{16}$:

$R_{11}$-$R_{17}$-$R_{12}$-$R_{11}$-$R_{14}$-$R_{18}$-$R_{17}$-$R_{11}$-$R_{14}$-$R_{12}$-$R_{11}$-$R_{11}$-$R_{12}$-$R_{11}$-$R_{11}$-$R_{11}$-$R_{11}$-$R_{12}$-$(R_{15})_n$-$R_{11}$, wherein $R_{11}$, $R_{12}$, $R_{14}$, $R_{15}$, and $R_{17}$ are as previously defined; $R_{18}$ is glutamine, asparagine, a basic hydrophilic amino acid, or a hydrophobic amino acid; and n is 0 or 1.

The XPF peptides generally include at least nineteen amino acids and may include up to forty amino acids. Accordingly, the hereinabove described basic peptide structure of XPF may include additional amino acids at the amino end, or at the carboxyl end, or at both the amino and carboxyl ends.

Thus, for example, an XPF peptide may include the following structure:

-$Y_{16}$-$X_{16}$- where $X_{16}$ is as previously defined and $Y_{16}$ is
(i) $R_{11}$, or
(ii) $R_{14}$-$R_{11}$,
where $R_{11}$ and $R_{14}$ are as previously defined.

An XPF peptide may include the following structure:

-$X_{16}$-$Z_{16}$- where $X_{16}$ is as previously defined and $Z_{16}$ is:
(i) $R_{11}$;
(ii) $R_{11}$-$R_{18}$;
(iii) $R_{11}$-$R_{18}$-Proline; or
(iv) $R_{11}$-$R_{18}$-Proline-$R_{12}$, wherein $R_{11}$, $R_{12}$, and $R_{18}$ are as previously defined.

An XPF peptide may also have the following structure:

$(Y_{16})_a$-$X_{16}$-$(Z_{16})_b$ where $X_{16}$, $Y_{16}$, and $Z_{16}$ are as previously defined, a is 0 or 1, and b is 0 or 1.

Preferred are XPF or PGLa peptides, which are characterized by the following primary amino acid sequences, as given in the accompanying sequence listing:

PGLa: (SEQ ID NO:12) (NH$_2$)
XPF: (SEQ ID NO:13)

A review of XPF and PGLa can be found in Hoffman et al, *EMBO J.*, 2:711–714, 1983; Andreu, et al, J. Biochem., 149:531–535, 1985; Gibson, et al *J. Biol. Chem.*, 261:5341–5349, 1986; and Giovannini, et al, Biochem. J., 243:113–120, 1987. These articles each are entirely incorporated herein by reference.

In accordance with yet another embodiment, X is a CPF peptide or an appropriate analogue or derivative thereof.

CPF peptides, as well as analogues and derivatives thereof, are herein sometimes referred to collectively as CPF peptides.

The CPF peptide may be one which includes the following basic peptide structure $X_{20}$:

$R_{21}$-$R_{21}$-$R_{22}$-$R_{22}$-$R_{21}$-$R_{21}$-$R_{23}$-$R_{21}$-$R_{21}$-$R_{21}$-$R_{23}$-$R_{21}$-$R_{21}$-$R_{24}$-$R_{25}$-$R_{21}$, wherein $R_{21}$ is a hydrophobic amino acid;
$R_{22}$ is a hydrophobic amino acid or a basic hydrophilic amino acid;
$R_{23}$ is a basic hydrophilic amino acid;
$R_{24}$ is a hydrophobic or neutral hydrophilic amino acid; and
$R_{25}$ is a basic or neutral hydrophilic amino acid.

The hereinabove basic structure is hereinafter symbolically indicated as $X_{20}$.

The hydrophobic amino acids are Ala, Cys, Phe, Gly, Ile, Leu, Met, Val, Trp, Tyr, norleucine (Nle), norvaline (Nva), and cyclohexylalanine (Cha).

The neutral hydrophilic amino acids are Asn, Gln, Ser, Thr, and homoserine (Hse).

The basic hydrophilic amino acids are Lys, Arg, His, Orn, homoarginine (Har), 2,4-diaminobutyric acid (Dbu), and p-aminophenylalanine.

The CPF peptide may include only the hereinabove noted amino acids or may include additional amino acids at the amino and/or carboxyl ends or both the amino and carboxyl ends. In general, the peptide does not include more than 40 amino acids.

The CPF peptides including the above basic structure preferably have from 1 to 4 additional amino acids at the amino end.

Accordingly, such preferred peptides may be represented by the structural formula:

$Y_{20}$-$X_{20}$- wherein $X_{20}$ is the hereinabove described basic peptide structure and $Y_{20}$ is (i) $R_{25}$-;
(ii) $R_{22}$-$R_{25}$-;
(iii) $R_{21}$-$R_{22}$-$R_{25}$;
(iv) $R_{22}$-$R_{21}$-$R_{22}$-$R_{25}$; or preferably
(v) Glycine -$R_{21}$-$R_{22}$-$R_{25}$, wherein $R_{21}$, $R_{22}$, and $R_{25}$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

-$X_{20}$-$Z_{20}$, wherein $X_{20}$ is the hereinabove defined basic peptide structure and $Z_{20}$ is (ii) $R_{21}$-$R_{21}$-;
(iii) $R_{21}$-$R_{21}$-$R_{24}$;
(iv) $R_{21}$-$R_{21}$-$R_{24}$-$R_{24}$;
(v) $R_{21}$-$R_{21}$-$R_{24}$-$R_{24}$-$R_{26}$;
(vi) $R_{21}$-$R_{21}$-$R_{24}$-$R_{24}$-$R_{26}$-Gln; or
(vii) $R_{21}$-$R_{21}$-$R_{24}$-$R_{24}$-$R_{26}$-Gln-Gln, wherein $R_{21}$ and $R_{24}$ are as previously defined, and $R_{26}$ is proline or a hydrophobic amino acid.

Preferred peptides may be represented by the following structural formula $(Y_{20})_a$-$X_{20}$-$(Z_{20})_b$ wherein $X_{20}$, $Y_{20}$ and $Z_{20}$ are as previously defined, a is 0 or 1, and b is 0 or 1.

Representative examples of CPF peptides which may be employed, some of which have been described in the literature, include the following sequences as given in the accompanying sequence listing:

(SEQ ID NO:14)
(SEQ ID NO:15)
(SEQ ID NO:16)
(SEQ ID NO:17)
(SEQ ID NO:18)
(SEQ ID NO:19)
(SEQ ID NO:20)
(SEQ ID NO:21)
(SEQ ID NO:22)
(SEQ ID NO:23)
(SEQ ID NO:24)
(SEQ ID NO:25)
(SEQ ID NO:26)

A review of the CPF peptides can be found in Richter, K., Egger, R., and Kreil (1986) *J. Biol. Chem.,* 261, 3676–3680; Wakabayashi, T., Kato, H., and Tachibaba, S. (1985) *Nucleic Acids Research,* 13, 1817–1828; and Gibson, B. W., Poulter, L., Williams, D. H., and Maggio, J. E. (1986) *J. Biol. Chem.,* 261, 5341–5349. These articles each are entirely incorporated herein by reference.

In accordance with yet another embodiment, X is a peptide which includes one of the following basic structures $X_{31}$ through $X_{37}$ wherein:

$X_{31}$ is -$[R_{31}$-$R_{32}$-$R_{32}$-$R_{33}$-$R_{31}$-$R_{32}$-$R_{32}]$-$_n$;
$X_{32}$ is -$[R_{32}$-$R_{32}$-$R_{33}$-$R_{31}$-$R_{32}$-$R_{32}$-$R_{31}]$-$_n$;
$X_{33}$ is -$[R_{32}$-$R_{33}$-$R_{31}$-$R_{32}$-$R_{32}$-$R_{31}$-$R_{32}]$-$_n$;
$X_{34}$ is -$[R_{33}$-$R_{31}$-$R_{32}$-$R_{32}$-$R_{31}$-$R_{32}$-$R_{32}]$-$_n$;
$X_{35}$ is -$[R_{31}$-$R_{32}$-$R_{32}$-$R_{31}$-$R_{32}$-$R_{32}$-$R_{33}]$-$_n$;
$X_{36}$ is -$[R_{32}$-$R_{32}$-$R_{31}$-$R_{32}$-$R_{32}$-$R_{33}$-$R_{31}]$-$_n$; and
$X_{37}$ is -$[R_{32}$-$R_{31}$-$R_{32}$-$R_{32}$-$R_{33}$-$R_{31}$-$R_{32}]$-$_n$;

wherein $R_{31}$ is a basic hydrophilic amino acid, $R_{32}$ is a hydrophobic amino acid, $R_{33}$ is a neutral hydrophilic, basic hydrophilic, or hydrophobic amino acid, and n is from 1 to 5.

The basic hydrophilic amino acids may be selected from the class consisting of Lys, Arg, His, Orn, homoarginine (Har), 2,4-diaminobutyric acid (Dbu), and p-aminophenylalanine.

The hydrophobic amino acids may be selected from the class consisting of Ala, Cys, Phe, Gly, Ile, Leu, Met, Pro, Val, Trp and Tyr, norleucine (Nle), norvaline (Nva), and cyclohexylalanine (Cha).

The neutral hydrophilic amino acids may be selected from the class consisting of Asn, Gln, Ser, Thr, and homoserine (Hse).

In accordance with one embodiment, when the peptide includes the structure $X_{31}$, the peptide may include the following structure:

$Y_{31}$-$X_{31}$, wherein $X_{31}$ is as hereinabove described, and $Y_{31}$ is:

(i) $R_{32}$;
(ii) $R_{32}$-$R_{32}$;
(iii) $R_{31}$-$R_{32}$-$R_{32}$;
(iv) $R_{33}$-$R_{31}$-$R_{32}$-$R_{32}$;
(v) $R_{32}$-$R_{33}$-$R_{31}$-$R_{32}$-$R_{32}$; or
(vi) $R_{32}$-$R_{32}$-$R_{33}$-$R_{31}$-$R_{32}$-$R_{32}$, wherein $R_{31}$, $R_{32}$, and $R_{33}$ are as hereinabove described.

In accordance with another embodiment, when the peptide includes the structure $X_{31}$, the peptide may include the following structure:

$X_{31}$-$Z_{31}$, wherein $X_{31}$ is as hereinabove described, and $Z_{31}$ is:

(i) $R_{31}$;
(ii) $R_{31}$-$R_{32}$;
(iii) $R_{31}$-$R_{32}$-$R_{32}$;
(iv) $R_{31}$-$R_{32}$-$R_{32}$-$R_{33}$;
(v) $R_{31}$-$R_{32}$-$R_{32}$-$R_{33}$-$R_{31}$; or
(vi) $R_{31}$-$R_{32}$-$R_{32}$-$R_{33}$-$R_{31}$-$R_{32}$, wherein $R_{31}$, $R_{32}$, and $R_{33}$ are as hereinabove described.

In accordance with yet another embodiment, the peptide may include the following structure:

$(Y_{31})_a$-$X_{31}$-$(Z_{31})_b$, wherein $Y_{31}$ and $Z_{31}$ are as previously defined, a is 0 or 1, and b is 0 or 1.

When the peptide includes the structure $X_{32}$, the peptide may include the following structure:

$Y_{32}$-$X_{32}$, wherein $X_{32}$ is as hereinabove described, and $Y_{32}$ is:

(i) $R_{31}$;
(ii) $R_{32}$-$R_{31}$;
(iii) $R_{32}$-$R_{32}$-$R_{31}$;
(iv) $R_{31}$-$R_{32}$-$R_{32}$-$R_{31}$;
(v) $R_{33}$-$R_{31}$-$R_{32}$-$R_{32}$-$R_{32}$; or
(vi) $R_{32}$-$R_{33}$-$R_{31}$-$R_{32}$-$R_{32}$-$R_{31}$, wherein $R_{31}$, $R_{32}$, and $R_{33}$ are as hereinabove described.

In another embodiment, when the peptide includes the structure $X_{32}$, the peptide may include the following structure:

$X_{32}$-$Z_{32}$, wherein $X_{32}$ is as hereinabove described, and $Z_{32}$ is:
(i) $R_{32}$;
(ii) $R_{32}$-$R_{32}$;
(iii) $R_{32}$-$R_{32}$-$R_{33}$;
(iv) $R_{32}$-$R_{32}$-$R_{33}$-$R_{31}$;
(v) $R_{32}$-$R_{32}$-$R_{33}$-$R_{31}$-$R_{32}$; or
(vi) $R_{32}$-$R_{32}$-$R_{33}$-$R_{31}$-$R_{32}$-$R_{32}$, wherein $R_{31}$, $R_{32}$, and $R_{33}$ are as hereinabove described.

In accordance with yet another embodiment, the peptide may include the following structure:

$(Y_{32})_a$-$X_{32}$-$(Z_{32})_b$, wherein $Y_{32}$ and $Z_{32}$ are as previously defined, a is 0 or 1, and b is 0 or 1.

In accordance with another embodiment, when the peptide includes the structure $X_{33}$, the peptide may include the following structure:

$Y_{33}$-$X_{33}$, wherein $X_{33}$ is as hereinabove described, and $Y_{33}$ is:
(i) $R_{32}$;
(ii) $R_{31}$-$R_{32}$;
(iii) $R_{32}$-$R_{31}$-$R_{32}$;
(iv) $R_{32}$-$R_{32}$-$R_{31}$-$R_{32}$;
(v) $R_{31}$-$R_{32}$-$R_{32}$-$R_{31}$-$R_{32}$; or
(vi) $R_{33}$-$R_{31}$-$R_{32}$-$R_{32}$-$R_{31}$-$R_{32}$, wherein $R_{31}$, $R_{32}$, and $R_{33}$ are as hereinabove described.

In accordance with another embodiment, when the peptide includes the structure $X_{33}$, the peptide may include the following structure:

$X_{33}$-$Z_{331}$ wherein $X_{33}$ is as hereinabove described, and $Z_{33}$ is:
(i) $R_{32}$;
(ii) $R_{32}$-$R_{33}$;
(iii) $R_{32}$-$R_{33}$-$R_{31}$;
(iv) $R_{32}$-$R_{33}$-$R_{31}$-$R_{32}$;
(v) $R_{32}$-$R_{33}$-$R_{31}$-$R_{32}$-$R_{32}$; or
(vi) $R_{32}$-$R_{33}$-$R_{31}$-$R_{32}$-$R_{32}$-$R_{31}$, wherein $R_{31}$, $R_{32}$, and $R_{33}$ are as hereinabove described.

In accordance with yet another embodiment, the peptide may include the following structure:

$(Y_{33})_a$-$X_{33}$-$(Z_{33})_b$, wherein $X_{33}$, $Y_{33}$, and $Z_{33}$ are as previously defined, a is 0 or 1, and b is 0 or 1.

In accordance with yet another embodiment, when the peptide includes the structure $X_{34}$, the peptide may include the following structure:

$Y_{34}$-$X_{34}$, wherein $X_{34}$ is as hereinabove described, and $Y_{34}$ is:
(i) $R_{32}$;
(ii) $R_{32}$-$R_{32}$;
(iii) $R_{31}$-$R_{32}$-$R_{32}$;
(iv) $R_{32}$-$R_{31}$-$R_{32}$-$R_{32}$;
(v) $R_{32}$-$R_{32}$-$R_{31}$-$R_{32}$-$R_{32}$; or
(vi) $R_{31}$-$R_{32}$-$R_{32}$-$R_{31}$-$R_{32}$-$R_{32}$, wherein $R_{31}$ and $R_{32}$ are as hereinabove described.

In accordance with another embodiment, when the peptide includes the structure $X_{34}$, the peptide may include the following structure:

$X_{34}$-$Z_{34}$, wherein $X_{34}$ is as hereinabove described, and $Z_{34}$ is:
(i) $R_{33}$;
(ii) $R_{33}$-$R_{31}$;
(iii) $R_{33}$-$R_{31}$-$R_{32}$;
(iv) $R_{33}$-$R_{31}$-$R_{32}$-$R_{32}$;
(v) $R_{33}$-$R_{31}$-$R_{32}$-$R_{32}$-$R_{31}$; or
(vi) $R_{33}$-$R_{31}$-$R_{32}$-$R_{32}$-$R_{31}$-$R_{32}$, wherein $R_{31}$, $R_{32}$, and $R_{33}$ are as hereinabove described.

In accordance with yet another embodiment, the peptide may include the following structure:

$(Y_{34})_a$-$X_{34}$-$(Z_{34})_b$, wherein $X_{34}$, $Y_{34}$, and $Z_{34}$ are as previously defined, a is 0 or 1, and b is 0 or 1.

In accordance with a further embodiment, when the peptide includes the structure $X_{35}$, the peptide may include the following structure:

$Y_{35}$-$X_{35}$, wherein $X_{35}$ is as hereinabove described, and $Y_{35}$ is:
(i) $R_{33}$;
(ii) $R_{32}$-$R_{33}$;
(iii) $R_{32}$-$R_{32}$-$R_{33}$;
(iv) $R_{31}$-$R_{31}$-$R_{32}$-$R_{32}$-$R_{33}$;
(v) $R_{32}$-$R_{31}$-$R_{32}$-$R_{32}$-$R_{33}$; or
(vi) $R_{32}$-$R_{32}$-$R_{31}$-$R_{32}$-$R_{32}$-$R_{33}$, wherein $R_{31}$, $R_{32}$, and $R_{33}$ are as hereinabove described.

In accordance with another embodiment, when the peptide includes the structure $X_{35}$, the peptide may include the following structure:

$X_{35}$-$Z_{35}$, wherein $X_{35}$ is as hereinabove described, and $Z_{35}$ is:
(i) $R_{31}$;
(ii) $R_{31}$-$R_{32}$;
(iii) $R_{31}$-$R_{32}$-$R_{32}$;
(iv) $R_{31}$-$R_{32}$-$R_{32}$-$R_{31}$;
(v) $R_{31}$-$R_{32}$-$R_{32}$-$R_{31}$-$R_{32}$; or
(vi) $R_{31}$-$R_{32}$-$R_{32}$-$R_{31}$-$R_{32}$-$R_{32}$, wherein $R_{31}$ and $R_{32}$ are as hereinabove described.

In accordance with yet another embodiment, the peptide may include the following structure:

$(Y_{35})_a$-$X_{35}$-$(Z_{35})_b$, wherein $X_{35}$, $Y_{35}$, and $Z_{35}$ are as previously defined, a is 0 or 1, and b is 0 or 1.

In accordance with a further embodiment, when the peptide includes the structure $X_{36}$, the peptide may include the following structure:

$Y_{36}$-$X_{36}$, wherein $X_{36}$ is as hereinabove described, and $Y_{36}$ is:
(i) $R_{31}$;
(ii) $R_{33}$-$R_{31}$;
(iii) $R_{32}$-$R_{33}$-$R_{31}$;
(iv) $R_{32}$-$R_{32}$-$R_{33}$-$R_{31}$;
(v) $R_{31}$-$R_{32}$-$R_{32}$-$R_{33}$-$R_{31}$; or
(vi) $R_{32}$-$R_{31}$-$R_{32}$-$R_{32}$-$R_{33}$-$R_{31}$, wherein $R_{31}$, $R_{32}$, and $R_{33}$ are as hereinabove described.

In accordance with another embodiment, when the peptide includes the structure $X_{36}$, the peptide may include the following structure:

$X_{36}$-$Z_{36}$, wherein $X_{36}$ is as hereinabove described, and $Z_{36}$ is:
(i) $R_{32}$;
(ii) $R_{32}$-$R_{32}$;
(iii) $R_{32}$-$R_{32}$-$R_{31}$;
(iv) $R_{32}$-$R_{32}$-$R_{31}$-$R_{32}$;
(v) $R_{32}$-$R_{32}$-$R_{31}$-$R_{32}$-$R_{32}$; or
(vi) $R_{32}$-$R_{32}$-$R_{31}$-$R_{31}$-$R_{32}$-$R_{33}$, wherein $R_{31}$, $R_{32}$, and $R_{33}$ are as hereinabove described.

In accordance with yet another embodiment, the peptide may include the following structure:

$(Y_{36})_a$-$X_{36}$-$(Z_{36})_b$, wherein $X_{36}$, $Y_{36}$, and $Z_{36}$ are as previously defined, a is 0 or 1, and b is 0 or 1.

In accordance with one embodiment, when the peptide includes the structure $X_{37}$, the peptide may include the structure $Y_{37}$-$X_{37}$, wherein $X_{37}$ is as hereinabove described, and $Y_{37}$ is:

(i) $R_{32}$;
(ii) $R_{31}$-$R_{32}$;
(iii) $R_{33}$-$R_{31}$-$R_{32}$
(iv) $R_{32}$-$R_{33}$-$R_{31}$-$R_{32}$;
(v) $R_{32}$-$R_{32}$-$R_{33}$-$R_{31}$-$R_{32}$; or
(v) $R_{31}$-$R_{32}$-$R_{32}$-$R_{33}$-$R_{31}$-$R_{32}$, wherein $R_{31}$, $R_{32}$, and $R_{33}$ are as hereinabove described.

In accordance with a further embodiment, when the peptide includes the structure $X_{37}$, the peptide may include the following structure:

$X_{37}$-$Z_{37}$, wherein $X_{37}$ is as hereinabove described, and $Z_{37}$ is:

(i) $R_{32}$;
(ii) $R_{32}$-$R_{31}$;
(iii) $R_{32}$-$R_{31}$-$R_{32}$;
(iv) $R_{32}$-$R_{31}$-$R_{32}$-$R_{32}$;
(v) $R_{32}$-$R_{31}$-$R_{32}$-$R_{32}$-$R_{33}$; or
(vi) $R_{32}$-$R_{31}$-$R_{32}$-$R_{32}$-$R_{33}$-$R_{31}$, wherein $R_{31}$, $R_{32}$, and $R_{33}$ are as hereinabove described.

In accordance with yet another embodiment, the peptide may include the following structure:

$(Y_{37})_a$-$X_{37}$-$(Z_{37})_b$, wherein $X_{37}$, $Y_{37}$, and $Z_{37}$ are as previously defined, a is 0 or 1, and b is 0 or 1.

In a preferred embodiment of the peptides according to formulae $X_{31}$ to $X_{37}$, n is 3, and most preferably the peptide is of one of the following structures as given in the accompanying sequence listing:

| | |
|---|---|
| (Lys Ile Ala Gly Lys Ile Ala)₃ | (SEQ ID NO: 27). |
| (Lys Ile Ala Lys Ile Ala Gly)₃ | (SEQ ID NO: 28). |
| (Lys Ile Ala Gly Lys Ile Gly)₃ | (SEQ ID NO: 29). |
| (Lys Leu Ala Gly Lys Leu Ala)₃ | (SEQ ID NO: 30). |
| (Lys Phe Ala Gly Lys Phe Ala)₃ | (SEQ ID NO: 31). |
| (Lys Ala Leu Ser Lys Ala Leu)₃ | (SEQ ID NO: 32). |
| (Lys Leu Leu Lys Ala Leu Gly)₃ | (SEQ ID NO: 33). |
| (Lys Ala Ile Gly Lys Ala Ile)₃ | (SEQ ID NO: 34). |
| (Gly Ile Ala Lys Ile Ala Lys)₃ | (SEQ ID NO: 35). |
| (Lys Ile Ala Lys Ile Phe Gly)₃ | (SEQ ID NO: 36). |
| (Gly Ile Ala Arg Ile Ala Lys)₃ | (SEQ ID NO: 37). |
| (Lys Phe Ala Arg Ile Ala Gly)₃ | (SEQ ID NO: 38). |
| (Gly Phe Ala Lys Ile Ala Lys)₃ | (SEQ ID NO: 39). |
| (Lys Ile Ala Gly Orn Ile Ala)₃ | (SEQ ID NO: 40). |
| (Lys Ile Ala Arg Ile Ala Gly)₃ | (SEQ ID NO: 41). |
| (Orn Ile Ala Gly Lys Ile Ala)₃ | (SEQ ID NO: 42). |
| (Gly Ile Ala Arg Ile Phe Lys)₃ | (SEQ ID NO: 43). |
| (Lys Nle Ala Gly Lys Nle Ala)₃ | (SEQ ID NO: 44). |
| (Lys Nle Ala Gly Lys Ile Ala)₃ | (SEQ ID NO: 45). |
| (Lys Ile Ala Gly Lys Nle Ala)₃ | (SEQ ID NO: 46). |
| (Lys Nva Ala Gly Lys Nva Ala)₃ | (SEQ ID NO: 47). |
| (Lys Nva Ala Gly Lys Ile Ala)₃ | (SEQ ID NO: 48). |
| (Lys Leu Leu Ser Lys Leu Gly)₃ | (SEQ ID NO: 49). |
| (Lys Leu Leu Ser Lys Phe Gly)₃ | (SEQ ID NO: 50). |
| (Lys Ile Ala Gly Lys Nva Ala)₃ | (SEQ ID NO: 51). |
| (His Ile Ala Gly His Ile Ala)₃ | (SEQ ID NO: 52). |
| (Ala Gly Lys Ile Ala Lys Ile)₃ | (SEQ ID NO: 53). |
| (Ile Ala Lys Ile Ala Gly Lys)₃ | (SEQ ID NO: 54). |
| (Lys Ile Ala Gly Arg Ile Ala)₃ | (SEQ ID NO: 55). |
| (Arg Ile Ala Gly Arg Ile Ala)₃ | (SEQ ID NO: 56). |
| (Lys Val Ala Gly Lys Ile Ala)₃ | (SEQ ID NO: 57). |
| (Lys Ile Ala Gly Lys Val Ala)₃ | (SEQ ID NO: 58). |
| (Ala Lys Ile Ala Gly Lys Ile)₃ | (SEQ ID NO: 59). |
| (Orn Ile Ala Gly Orn Ile Ala)₃ | (SEQ ID NO: 60). |
| (Lys Phe Ala Gly Lys Ile Ala)₃ | (SEQ ID NO: 61). |
| (Lys Ile Ala Gly Lys Phe Ala)₃ | (SEQ ID NO: 62). |
| (Lys Cha Ala Gly Lys Ile Ala)₃ | (SEQ ID NO: 63). |
| (Lys Nle Ala Lys Ile Ala Gly)₃ | (SEQ ID NO: 64). |
| (Arg Ile Ala Gly Lys Ile Ala)₃ | (SEQ ID NO: 65). |
| (Har Ile Ala Gly Har Ile Ala)₃ | (SEQ ID NO: 66). |
| (Xaa Ile Ala Gly Lys Ile Ala)₃ | (SEQ ID NO: 67). |
| (Lys Ile Ala Gly Xaa Ile Ala)₃ | (SEQ ID NO: 68). |

In (SEQ ID NO:67) and (SEQ ID NO:68), Xaa is p-aminophenylalanine.

In accordance with another embodiment, X is a peptide which includes the following basic structure $X_{40}$:

$R_{31}$-$R_{32}$-$R_{32}$-$R_{33}$-$R_{34}$-$R_{32}$-$R_{32}$-$R_{31}$-$R_{32}$-$R_{32}$-$R_{32}$-$R_{34}$-$R_{32}$, wherein $R_{31}$, $R_{32}$, and $R_{33}$ are as hereinabove described, and $R_{34}$ is a basic hydrophilic or hydrophobic amino acid.

In accordance with one embodiment, the peptide may include the following structure:

$Y_{40}$-$X_{40}$, wherein $X_{40}$ is as hereinabove described, and $Y_{40}$ is:

(i) $R_{32}$;
(ii) $R_{32}$-$R_{32}$;
(iii) $R_{34}$-$R_{32}$-$R_{32}$
(iv) $R_{33}$-$R_{34}$-$R_{32}$-$R_{32}$;
(v) $R_{32}$-$R_{33}$-$R_{34}$-$R_{32}$-$R_{32}$;
(vi) $R_{32}$-$R_{32}$-$R_{33}$-$R_{34}$-$R_{32}$-$R_{32}$; or
(vii) $R_{31}$-$R_{32}$-$R_{32}$-$R_{33}$-$R_{34}$-$R_{32}$-$R_{32}$, wherein $R_{31}$, $R_{32}$, $R_{33}$, and $R_{34}$ are as hereinabove described.

In accordance with another embodiment, X is a peptide which includes the following structure:

$X_{40}$-$Z_{40}$, wherein $X_{40}$ is as hereinabove described and $Z_{40}$ is:

(i) $R_{31}$;
(ii) $R_{31}$-$R_{32}$;
(iii) $R_{31}$-$R_{32}$-$R_{32}$;
(iv) $R_{31}$-$R_{32}$-$R_{32}$-$R_{33}$;
(v) $R_{31}$-$R_{32}$-$R_{32}$-$R_{33}$-$R_{34}$;
(vi) $R_{31}$-$R_{32}$-$R_{32}$-$R_{33}$-$R_{34}$-$R_{32}$; or
(vii) $R_{31}$-$R_{32}$-$R_{32}$-$R_{33}$-$R_{34}$-$R_{32}$-$R_{32}$, wherein $R_{31}$, $R_{32}$, $R_{33}$, and $R_{34}$ are as hereinabove described.

In accordance with yet another embodiment, the peptide may include the following structure:

$(Y_{40})_a$-$X_{40}$-$(Z_{40})_b$, wherein $X_{40}$, $Y_{40}$, and $Z_{40}$ are as previously defined, a is 0 or 1, and b is 0 or 1.

In a preferred embodiment, the peptide has the following structural formula as given in the accompanying sequence listing:

(SEQ ID NO: 69)

In another preferred embodiment, the peptide has the following structural formula as given in the accompanying sequence listing:

(SEQ ID NO: 70)

In accordance with a further embodiment, the peptide has one of the following structural formulae as given in the accompanying sequence listing:

(SEQ ID NO: 71)
(SEQ ID NO: 72)
(SEQ ID NO: 73)
(SEQ ID NO: 74)
(SEQ ID NO: 75)
(SEQ ID NO: 76)
(SEQ ID NO: 77)
(SEQ ID NO: 78)

(SEQ ID NO: 79)
(SEQ ID NO: 80)
(SEQ ID NO: 81)
(SEQ ID NO: 82)
(SEQ ID NO: 83)
(SEQ ID NO: 84)
(SEQ ID NO: 85)

In accordance with another embodiment, X is a peptide which includes one of the following structural formulae:

(i)—(Lys Ile Ala Lys Lys Ile Ala)$_n$-,
(ii)—(Lys Phe Ala Lys Lys Phe Ala)$_n$-, and
(iii)—(Lys Phe Ala Lys Lys Ile Ala)$_n$-, wherein n is from 1 to 5. Preferably, n is 3, and the peptide has one of the following structural formulae:

(Lys Ile Ala Lys Lys Ile Ala)$_3$ (SEQ ID NO: 86)
(Lys Phe Ala Lys Lys Phe Ala)$_3$ (SEQ ID NO: 87)
(Lys Phe Ala Lys Lys Ile Ala)$_3$ (SEQ ID NO: 88)

In accordance with another embodiment, the X is a peptide which is selected from the group consisting of the following structural formulae as given in the accompanying sequence listing:

(SEQ ID NO: 89)
(SEQ ID NO: 90)
(SEQ ID NO: 91)
(SEQ ID NO: 92)

In accordance with yet another embodiment, X is a cecropin or sarcotoxin.

The term "cecropin" includes the basic structure as well as analogues and derivatives thereof. The cecropins and analogues and derivatives thereof are described in *Ann. Rev. Microbiol.,* 1987, Vol. 41, pages 103–26, in particular page 108, and in Christensen, et al., *PNAS,* Vol. 85, pgs. 5072–76, which are hereby incorporated by reference.

The term "sarcotoxin" includes the basic materials as well as analogues and derivatives thereof. The sarcotoxins and analogues and derivatives thereof are described in *Molecular Entomology,* pages 369–78, in particular page 375, Alan R. Liss, Inc. (1987), which is hereby incorporated by reference.

In accordance with another embodiment, X is melittin or an analogue or derivative thereof. Melittin is an amphipathic peptide consisting of 26 amino acid residues, and is isolated from honeybee (Apis mellifera) venom. Habermann, et al., *Hoppe-Seyler's Zeitschrift Physiol. Chem.,* Vol. 348, pgs. 37–50 (1987) (which document is entirely incorporated herein by reference). Melittin has the following structural formula as represented by the three-letter amino acid code:

```
Gly Ile Gly Ala Val Leu Lys Val Leu Thr Thr Gly Leu Pro Ala Leu (SEQ ID NO: 93)
                5               10                      15
Ile Ser Trp Ile Lys Arg Lys Arg Gln Gln
                20              25
```

In another embodiment, X is an amphiphilic peptide which is a hybrid of a cecropin peptide and a melittin peptide or an analogue thereof. Such hybrid peptides are described in U.S. Pat. No. 5,714,467 which is herein incorporated by reference. An example of such a peptide is given below.

I Lys-Ala-Lys-Leu-Phe-Ala-Lys-Ala-Gly-Ala-Gly-Ala-Val-Leu-Lys-Ala-Leu-Lys-Lys-Gly-Leu-Lys-Ala-Leu-Ile-Lys (SEQ ID NO: 156) (—OH or —NH$_2$)

In another embodiment, X is an amphiphilic peptide which includes the following basic structure $X_{50}$:

$R_{41}$-$R_{42}$-$R_{42}$-$R_{41}$-$R_{42}$-$R_{42}$-$R_{41}$-$R_{41}$-$R_{42}$-$R_{41}$-$R_{41}$.

$R_{41}$ is a hydrophobic amino acid, and $R_{42}$ is a basic hydrophilic or neutral hydrophilic amino acid.

In one embodiment, the peptide includes the basic structure $Y_{50}$-$X_{50}$, wherein $X_{50}$ is as hereinabove described and $Y_{50}$ is:

(I) $R_{41}$;
(ii) $R_{42}$-$R_{41}$; or
(iii) $R_{42}$-$R_{42}$-$R_{41}$, wherein $R_{41}$ and $R_{42}$ are as hereinabove described.

In one embodiment, $R_{41}$ is leucine. In another embodiment, $R_{42}$ is lysine. Representative examples of peptides in accordance with this aspect of the present invention include those having the following structures:

(SEQ ID NO: 94)
(SEQ ID NO: 95)
(SEQ ID NO: 96)
(SEQ ID NO: 97)

In accordance with another embodiment, X is an amphiphilic peptide which includes the following basic structure $X_{52}$:

$R_{42}$-$R_{41}$-$R_{42}$-$R_{42}$-$R_{41}$-$R_{41}$-$R_{42}$-$R_{42}$-$R_{41}$-$R_{42}$-$R_{42}$, wherein $R_{41}$ is a hydrophobic amino acid, and $R_{42}$ is a basic hydrophilic or neutral hydrophilic amino acid.

In one embodiment $R_{41}$ is leucine. In another embodiment, $R_{42}$ is lysine.

In one embodiment, the peptide includes the basic structure $Y_{52}$-$X_{52}$, wherein $X_{52}$ is as hereinabove described, and $Y_{52}$ is:

(I) $R_{42}$;
(ii) $R_{41}$-$R_{42}$;
(iii) $R_{41}$-$R_{41}$-$R_{42}$;
(iv) $R_{42}$-$R_{41}$-$R_{41}$-$R_{42}$; or
(v) $R_{42}$-$R_{42}$-$R_{41}$-$R_{41}$-$R_{42}$, wherein $R_{41}$ and $R_{42}$ are as hereinabove described.

In one embodiment, the peptide may have the following structure:

(SEQ ID NO.: 98)

```
Lys Lys Leu Leu Lys Lys Leu Lys Lys Leu Leu Lys Lys Leu Arg Arg (SEQ ID NO.: 98)
                5               10                      15
```

In another embodiment, the peptide includes the basic structure $X_{52}$-$Z_{52}$, wherein $X_{52}$ is as hereinabove described, and $Z_{52}$ is:
- (I) $R_{41}$;
- (ii) $R_{41}$-$R_{41}$;
- (iii) $R_{41}$-$R_{41}$-$R_{42}$;
- (iv) $R_{41}$-$R_{41}$-$R_{42}$-$R_{42}$; or
- (v) $R_{41}$-$R_{41}$-$R_{42}$-$R_{42}$-$R_{41}$, wherein $R_{41}$ and $R_{42}$ are as hereinabove described.

In one embodiment, the peptide may have the following structure:

Lys Leu Lys Lys Leu Leu Lys Lys Leu Lys Lys Leu Leu Lys Lys Leu (SEQ ID NO: 99)
              5                   10              15

(SEQ ID NO: 99)

In another embodiment, the peptide may include the structure:

$(Y_{52})_a$-$X_{52}$-$(Z52)_b$, wherein $X_{52}$, $Y_{52}$, and $Z_{52}$ are as hereinabove described, a is 0 or 1, and b is 0 or 1.

In another embodiment, X is a biologically active amphiphilic peptide which includes the following basic structure $X_{54}$:

$R_{41}$-$R_{42}$-$R_{42}$-$R_{41}$-$R_{41}$-$R_{42}$-$R_{42}$-$R_{41}$-$R_{42}$-$R_{42}$-$R_{41}$-$R_{41}$-$R_{42}$-$R_{42}$-$R_{42}$-$R_{43}$;

wherein $R_{41}$ and $R_{42}$ are as hereinabove described, and $R_{43}$ is a neutral hydrophilic amino acid.

In one embodiment, the peptide may have the following structure:

(SEQ ID NO: 100)

In another embodiment, the peptide may have the following structure:

(SEQ ID NO: 101)

In another embodiment, X is a biologically active amphiphilic peptide which includes the following basic structure $X_{56}$;

$R_{41}$-$R_{42}$-$R_{42}$-$R_{41}$-$R_{41}$-$R_{42}$-$R_{42}$-$R_{41}$ -$R_{41}$-$R_{42}$-$R_{42}$-$R_{44}$, wherein $R/_{41}$ and $R_{42}$ are as hereinabove described, and $R_{44}$ is a neutral hydrophilic amino acid or proline.

In one embodiment, the peptide may include the structure: $X_{56}$-$Z_{56}$ wherein $X_{56}$ is as hereinabove described, and $Z_{56}$ is:
- (I) -$R_{42}$;
- (ii) -$R_{42}$-$R_{42}$;
- (iii) -$R_{42}$-$R_{42}$-$R_{41}$;
- (iv) -$R_{42}$-$R_{42}$-$R_{41}$-$R_{41}$;
- (v) -$R_{42}$-$R_{42}$-$R_{41}$-$R_{41}$-$R_{42}$;
- (vi) -$R_{42}$-$R_{42}$-$R_{41}$-$R_{41}$-$R_{42}$-$R_{42}$; or
- (vii) -$R_{42}$-$R_{42}$-$R_{41}$-$R_{41}$-$R_{42}$-$R_{42}$-$R_{41}$, wherein $R_{41}$ and $R_{42}$ are as hereinabove described.

In a preferred embodiment, the peptide may have one of the following structures:

(SEQ ID NO: 102); or (SEQ ID NO: 103).

In another embodiment, X is a biologically active amphiphilic peptide which includes the following basic structure $X_{58}$;

$R_{41}$-$R_{41}$-$R_{42}$-$R_{42}$-$R_{41}$-$R_{42}$-$R_{42}$-$R_{41}$-$R_{41}$-$R_{42}$-$R_{42}$-$R_{41}$-$R_{43}$, wherein $R_{41}$, $R_{42}$, and $R_{43}$ are as hereinabove described.

In one embodiment, the peptide includes the structure $X_{58}$-$Z_{58}$, wherein $X_{58}$ is as hereinabove described, and $Z_{58}$ is:
- (I) -$R_{41}$;
- (ii) -$R_{41}$-$R_{45}$;
- (iii) -$R_{41}$-$R_{45}$-$R_{45}$;
- (iv) -$R_{41}$-$R_{45}$-$R_{45}$-$R_{43}$;
- (v) -$R_{41}$-$R_{45}$-$R_{45}$-$R_{43}$-$R_{41}$;
- (vi) -$R_{41}$-$R_{45}$-$R_{45}$-$R_{43}$-$R_{41}$-$R_{43}$;
- (vii) -$R_{41}$-$R_{45}$-$R_{45}$-$R_{43}$-$R_{41}$-$R_{43}$-$R_{43}$;
- (viii) -$R_{41}$-$R_{45}$-$R_{45}$-$R_{43}$-$R_{41}$-$R_{43}$-$R_{43}$-$R_{45}$; or
- (ix) -$R_{41}$-$R_{45}$-$R_{45}$-$R_{43}$-$R_{41}$-$R_{43}$-$R_{43}$-$R_{45}$-$R_{43}$, wherein $R_{41}$ and $R_{43}$ are as hereinabove described, and $R_{45}$ is proline.

In one embodiment, the peptide has the following structure:

(SEQ ID NO: 104).

In another embodiment, X is a biologically active amphiphilic peptide which includes the following basic structure $X_{60}$:

$R_{41}$-$R_{41}$-$R_{43}$-$R_{42}$-$R_{41}$-$R_{41}$-$R_{41}$-$R_{41}$-$R_{41}$-$R_{41}$-$R_{42}$-$R_{41}$-$R_{41}$-$R_{42}$-$R_{42}$-$R_{41}$-$R_{41}$-$R_{42}$-$R_{42}$-$R_{41}$-, wherein $R_{41}$, $R_{42}$, and $R_{43}$ are as hereinabove described. In one embodiment, the peptide may have the following structure:

(SEQ ID NO: 105).

In accordance with another embodiment, X is a peptide which includes the following basic structure $X_{62}$:

-$R_{41}$-$R_{42}$-$R_{42}$-$R_{41}$-$R_{42}$-$R_{42}$-$R_{41}$-, wherein $R_{41}$ and $R_{42}$ are as hereinabove described.

In one embodiment, the peptide includes the following structure $Y_{62}$-$X_{62}$ where $X_{62}$ is as hereinabove described, and $Y_{62}$ is
- (I) -$R_{11}$;
- (ii) -$R_{42}$-$R_{41}$;
- (iii) -$R_{42}$-$R_{42}$-$R_{41}$; or
- (iv) -$R_{41}$-$R_{42}$-$R_{42}$-$R_{41}$, wherein $R_{41}$ and $R_{42}$ are as hereinabove described.

Representative examples of such peptides include the following, the sequences of which are given in the accompanying sequence listing:

(SEQ ID NO: 106)
(SEQ ID NO: 107)
(SEQ ID NO: 108)
(SEQ ID NO: 109)
(SEQ ID NO: 110)
(SEQ ID NO: 111)
(SEQ ID NO: 141)
(SEQ ID NO: 142)
(SEQ ID NO: 143)
(SEQ ID NO: 144)
(SEQ ID NO: 145)
(SEQ ID NO: 146)

In one embodiment, the peptide includes the structure $X_{62}$-$Z_{62}$, wherein $X_{62}$ is as hereinabove described, and $Z_{62}$ is:
- (I) -$R_{41}$;
- (ii) -$R_{41}$-$R_{42}$;

(iii) $-R_{41}-R_{42}-R_{42}$; or (iv) $-R_{41}-R_{42}-R_{42}-R_{41}$, where $R_{41}$ and $R_{42}$ are as hereinabove described.

A representative example includes the following peptide having the structural formula given below and listed in the accompanying sequence listing:

(SEQ ID NO: 112)

In another embodiment, the peptide has the structure $(Y_{62})_a-X_{62}-(Z_{62})_b$, wherein $X_{62}$, $Y_{62}$, and $Z_{62}$ are as hereinabove described, a is 0 or 1, and b is 0 or 1.

Representative examples of such peptides include the following, the structures of which are given in the accompanying sequence listing:

(SEQ ID NO: 113)

(SEQ ID NO: 114)

(SEQ ID NO: 115)

(SEQ ID NO: 116)

In another embodiment, X is a peptide having the following structural formula:

(SEQ ID NO: 117)

In another embodiment, X is a biologically active amphiphilic peptide including the following basic structure $X_{64}$:

$-R_{42}-R_{42}-R_{42}-R_{41}-R_{41}-R_{42}-R_{42}-R_{41}$-, wherein $R_{41}$ and $R_{42}$ are as hereinabove described.

In one embodiment, the peptide may include the structure $Y_{64}-X_{64}$, wherein $X_{64}$ is as hereinabove described, and $Y_{64}$ is:

(I) $R_{41}$; or (ii) $R_{42}-R_{41}$, wherein $R_{41}$ and $R_{42}$ are as hereinabove described.

In another embodiment, the peptide may include the structure $X_{64}-Z_{64}$, wherein $X_{64}$ is as hereinabove described, and $Z_{64}$ is:

(I) $R_{42}$;

(ii) $R_{42}-R_{42}$; or (iii) $R_{42}-R_{42}-R_{41}$, wherein $R_{41}$ and $R_{42}$ are as hereinabove described.

In yet another embodiment, the peptide has the structure:

$(Y_{64})_a-X_{64}-(Z_{64})_b$, wherein $X_{64}$, $Y_{64}$, and $Z_{64}$ are as hereinabove described, a is 0 or 1, and b is 0 or 1.

Representative examples of such peptides include the following:

(SEQ ID NO: 127)

(SEQ ID NO: 128)

(SEQ ID NO: 129)

In yet another embodiment, X is a biologically active amphiphilic peptide including the following basic structure $X_{66}$:

$R_{41}-R_{42}-R_{42}-R_{41}-R_{41}-R_{41}-R_{42}-R_{41}-R_{42}-R_{42}-R_{41}$, wherein $R_{41}$ and $R_{42}$ are hereinabove described and $R_{46}$ is glutamic acid. A representative example of such a peptide is the following:

(SEQ ID NO: 130)

In yet another embodiment, X is a biologically active amphiphilic peptide including the following basic structure $X_{68}$:

$-R_{42}-R_{42}-R_{41}-R_{41}-R_{42}-R_{46}-R_{41}-R_{42}-R_{42}-R_{41}$-, wherein $R_{41}$, $R_{42}$, and $R_{46}$ are hereinabove described.

In one embodiment, the peptide includes the following basic structure $Y_{68}-X_{68}$, wherein $X_{68}$ is as hereinabove described, and $Y_{68}$ is $R_{41}$ (defined above).

Representative examples of such peptides include the following:

(SEQ ID NO: 131)

(SEQ ID NO: 132).

In another embodiment, X is a biologically active amphiphilic peptide including the following basic structure $X_{70}$:

$-R_{41}-R_{42}-R_{42}-R_{41}-R_{41}-R_{42}-R_{42}-R_{41}-R_{42}-R_{42}-R_{41}-R_{41}$-, wherein $R_{41}$ and $R_{42}$ are hereinabove described. A representative example of such a peptide has the following structure:

(SEQ ID NO: 133).

In another embodiment, X is a biologically active amphiphilic peptide including the following basic structure $X_{72}$:

$-R_{42}-R_{12}-R_{41}-R_{41}-R_{42}-R_{47}-R_{41}-R_{42}-R_{42}-R_{41}$-, wherein $R_{41}$ and $R_{42}$ are hereinabove described, and $R_{47}$ is aspartic acid. A representative example of such a peptide has the following structure:

(SEQ ID NO: 134).

In yet another embodiment, X is a biologically active amphiphilic peptide having the following structure:

(SEQ ID NO: 135).

In yet another embodiment, X is a biologically active amphiphilic peptide including the following structure $X_{74}$:

$R_{42}-R_{41}-R_{42}-R_{41}-R_{41}-R_{42}-R_{42}-R_{41}-R_{46}-R_{42}-R_{41}$, wherein $R_{41}$, $R_{42}$, and $R_{46}$ are hereinabove described. A representative example of such a peptide has the following structure:

(SEQ ID NO: 136).

In another embodiment, X is a biologically active amphiphilic peptide including the following structure $X_{76}$:

$-R_{41}-R_{42}-R_{42}-R_{41}-R_{41}-R_{42}$-, wherein $R_{41}$ and $R_{42}$ are hereinabove described.

In another embodiment, the peptide includes the structure $Y_{76}-X_{76}$-, wherein $X_{76}$ is as hereinabove described, and $Y_{76}$ is:

(I) $-R_{42}$;

(ii) $-R_{42}-R_{42}$;

(iii) $-R_{41}-R_{42}-R_{42}$;

(iv) $-R_{41}-R_{41}-R_{42}-R_{42}$;

(v) $-R_{42}-R_{41}-R_{41}-R_{42}-R_{42}$; or (vi) $-R_{42}-R_{42}-R_{41}-R_{41}-R_{42}-R_{42}$, wherein $R_{41}$ and $R_{42}$ are as hereinabove described.

In another embodiment, the peptide includes the structure $X_{76}-Z_{76}$, wherein $X_{76}$ is as hereinabove described, and $Z_{76}$ is:

(I) $R_{48}$;

(ii) $R_{49}-R_{41}$; or (iii) $R_{48}-R_{41}-R_{42}$, wherein $R_{41}$ and $R_{42}$ are as hereinabove described, and $R_{48}$ is a basic hydrophilic, neutral hydrophilic, or hydrophobic amino acid.

In yet another embodiment, the peptide has the following structural formula:

$(Y_{76})_a-X_{76}-(Z_{76})_b$, wherein $X_{76}$, $Y_{76}$, and $Z_{76}$ are as hereinabove described, a is 0 or 1, and b is 0 or 1.

Representative examples of such peptides include the following:

(SEQ ID NO: 137)

(SEQ ID NO: 138)

(SEQ ID NO: 139).

In yet another embodiment, X is a biologically active amphiphilic peptide including the following structural formula $X_{78}$:

-$R_{41}$-$R_{42}$-$R_{41}$-$R_{41}$-$R_{42}$-$R_{42}$-$R_{41}$-$R_{42}$-$R_{42}$-$R_{41}$, wherein $R_{41}$ and $R_{42}$ are as hereinabove described. A representative example of such a peptide has the following structure:

(SEQ ID NO: 140).

In another embodiment, X has the following structure:

(SEQ ID NO: 149).

In another embodiment, X is a biologically active amphiphilic peptide including the following structural formula $X_{80}$:

-$R_{41}$-$R_{42}$-$R_{42}$-$R_{41}$-$R_{41}$-$R_{42}$-$R_{46}$-$R_{41}$-$R_{41}$-$R_{42}$-$R_{41}$-, wherein $R_{41}$, $R_{42}$, and $R_{46}$ are as hereinabove described. A representative example of such a peptide has the following structure:

(SEQ ID NO: 151).

In accordance with yet another embodiment, X is an ion channel-forming peptide or protein.

Ion channel-forming proteins or peptides which may be employed include defensins, also known as human neutrophil anti-microbial peptides (HNP), major basic protein (MBP) of eosinophils, bactericidal permeability-increasing protein (BPI), and a pore-forming cytotoxin called variously perforin, cytolysin, or pore-forming protein. Defensins are described in Selsted, et al., *J. Clin. Invest.,* Vol. 76, pgs. 1436–1439 (1985). MBP proteins are described in Wasmoen, et al., *J. Biol. Chem.,* Vol. 263, pgs. 12559–12563 (1988). BPI proteins are described in Ooi, et al., *J. Biol. Chem.,* Vol. 262, pgs. 14891–14894 (1987). Perforin is described in Henkart, et al., *J. Exp. Med.,* 160: 75 (1984), and in Podack, et al., *J. Exp. Med.,* 160:695 (1984). The above articles each are entirely incorporated herein by reference.

The term "ion channel-forming proteins" includes the basic structures of the ion channel-forming proteins as well as analogues and derivatives.

In accordance with yet another embodiment, each of the amino acid residues of the peptides or proteins may be a D-amino acid or glycine. Although the scope of this particular embodiment is not to be limited to any theoretical reasoning, it is believed that the above-mentioned peptides or proteins, when consisting entirely of D-amino acid or glycine residues, may have increased resistance to proteolytic enzymes while retaining their activity. Such peptides thus may be administered orally. Also, in accordance with another embodiment, all of the amino acid residues may be D-amino acid or glycine residues, or L-amino acid or glycine residues.

It is also to be understood that the peptides or proteins may be administered in combination with one another.

In accordance with another embodiment, the N-terminal substituted peptides or proteins of the present invention may be employed in combination with an ion having pharmacological properties for the purposes hereinabove described.

An ion having pharmacological properties is one which, when introduced into a target cell, virus, or virally-infected cell, inhibits and/or prevents and/or destroys the growth of the target cell, virus, or virally-infected cell.

Such an ion having pharmacological properties is one which, in the absence of an ion channel forming peptide, is unable to cross a natural or synthetic lipid membrane, in particular a cell or virus membrane, in sufficient amounts to affect a cell or virus adversely.

The peptide or protein and ion having pharmacological properties may be administered as a single composition or in separate compositions, and the single or separate compositions may include additional materials, actives, and/or inactives, in addition to the peptide or protein and ion having pharmacological properties. As representative examples of ions having pharmacological properties which may be employed, there may be mentioned fluoride, peroxide, bicarbonate, silver, zinc, mercury, arsenic, copper, platinum, antimony, gold, thallium, nickel, selenium, bismuth, and cadmium ions.

The peptide or protein and the ion having pharmacological properties, whether administered or prepared in a single composition or in separate compositions, are employed in amounts effective to inhibit and/or prevent and/or destroy the growth of the target cell, virus, or virally-infected cell. In effect, the ion potentiates the action of the peptide, i.e., the amount of ion is effective to reduce the maximum effective concentration of the peptide or protein for inhibiting growth of a target cell, virus, or virally-infected cell.

The ion having pharmacological properties, when used topically, is generally employed in a concentration of from 0.05% to 2.0%. When used systemically, the ion is generally employed in an amount of from 1 to 10 mg. per kg. of host weight. Peptide or protein dosages may be within the ranges hereinabove described.

It is also to be understood that the peptide or protein and ion having pharmacological properties, may be delivered or administered in different forms. For example, the ion may be administered orally, while the peptide may be administered by IV or IP.

As representative examples of administering the peptide or protein and ion for topical or local administration, the peptide could be administered in an amount of up to about 1% weight to weight and the ion delivered in an amount of about 50 mM (about 0.1%). Alternatively, the ion, in the form of a salt such as sodium fluoride, could be administered orally in conjunction with systemic administration of the peptide or protein. For example, the peptide or protein may be administered IV or IP to achieve a serum dose of 100 micrograms per milliliter (10 milligrams per kilogram) in conjunction with an oral dose of ion, in particular, sodium fluoride, of 10 meq per kilogram.

In accordance with another embodiment, the peptides or proteins of the present invention may be administered to a host in combination with an antibiotic selected from the class consisting of bacitracins, gramacidin, polymyxin, vancomycin, teichoplanin, aminoglycosides, hydrophobic antibiotics, penicillin, monobactams, or derivatives or analogues thereof.

The bacitracins, gramacidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicine (e.g., gentamicin $C_1$, gentamicin $C_2$, gentamicin $C_{1a}$), netilmicin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to, benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides, such as erythromycin, roxythromycin, clarithromycin, etc.; 9-N-alkyl derivatives of erythromycin; midecamycin acetate; azithromycin; flurithromycin; rifabutin; rokitamycin; a 6-0-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-0-methyl-1-4"-O-carbamoyl erythromycin known as A-63075 (Abbott); 3-formylrifamycin SV-hydrazones with diazabicycloalkyl side chains, such as CGP-27557 and CGP-2986 (Ciba-Geigy); and 16-membered macrolides having a 3-0-alpha-L-cladinosyl moiety, such as 3-0-alpha-L-cladinosyldeepoxy rosaramicin; tylosins and acyl demycinosyl tylosins.

In addition to the macrolides hereinabove described, rifamycin, carbenicilllin, and nafcillin may be employed as well.

Other antibiotics which may be used (whether or not hydrophobic) are antibiotics which are 50-S ribosome inhibitors such as lincomycin; clindamycin; and chloramphenicol; etc.; and antibiotics which have a large lipid like lactone ring, such as mystatin; pimaricin, etc.

The peptide or protein and antibiotic may be administered by direct administration to a target cell by systemic or topical administration to a host which includes the target cell, in order to prevent, destroy, or inhibit the growth of a target cell. Target cells whose growth may be prevented, inhibited, or destroyed by the administration of the peptides and antibiotic include Gram-positive and Gram-negative bacteria, as well as fungal cells.

The antibiotic, such as those hereinabove described, or derivatives or analogues thereof, when used topically, is generally employed in a concentration of about 0.1% to about 10% (by weight). When used systemically, the antibiotic or derivative or analogue thereof is generally employed in an amount of from 1.25 mg. to about 45 mg. per kg. of host weight per day. Peptide or protein dosages may be those as hereinabove described.

As representative examples of administering the peptide or protein and antibiotic for topical or local administration, the peptide or protein could be administered in an amount of from 0.1% to about 10% weight to weight, and the antibiotic is delivered in an amount of from about 0.1% to about 10% weight to weight.

In accordance with another embodiment, the peptides or proteins of the present invention may be administered in combination with an anti-parasitic agent or an anti-fungal agent.

Anti-parasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents may also have anti-fungal activity, and that anti-fungal agents may have anti-parasitic activity.

In accordance with another embodiment, the peptides or proteins of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfoxacin, temafloxacin, and rufloxacin.

BRIEF DESCRIPTION OF THE DRAWINGS

The invention will be more fully understood when considered in view of the specific examples that follow and the attached drawing, wherein:

FIG. 14 is a body weight curve for SCID mice dosed twice a week with either MSI-344(SEQ ID NO: 154 —OH) or MSI-1857(SEQ ID NO: 154 —OH methane sulfonate).

FIG. 15 is a standard curve relating antibacterial activity (zone diameter) to the concentration of MSI-1324(OCT-SEQ ID NO: 143 —$NH_2$ methane sulfonate).

FIG. 16 shows the concentration of MSI-1324)OCT-SEQ ID NO: 143 —NH$_2$ methane sulfonate) in plasma after a single iv dose.

DETAILED DESCRIPTION OF THE INVENTION

Figure 1:
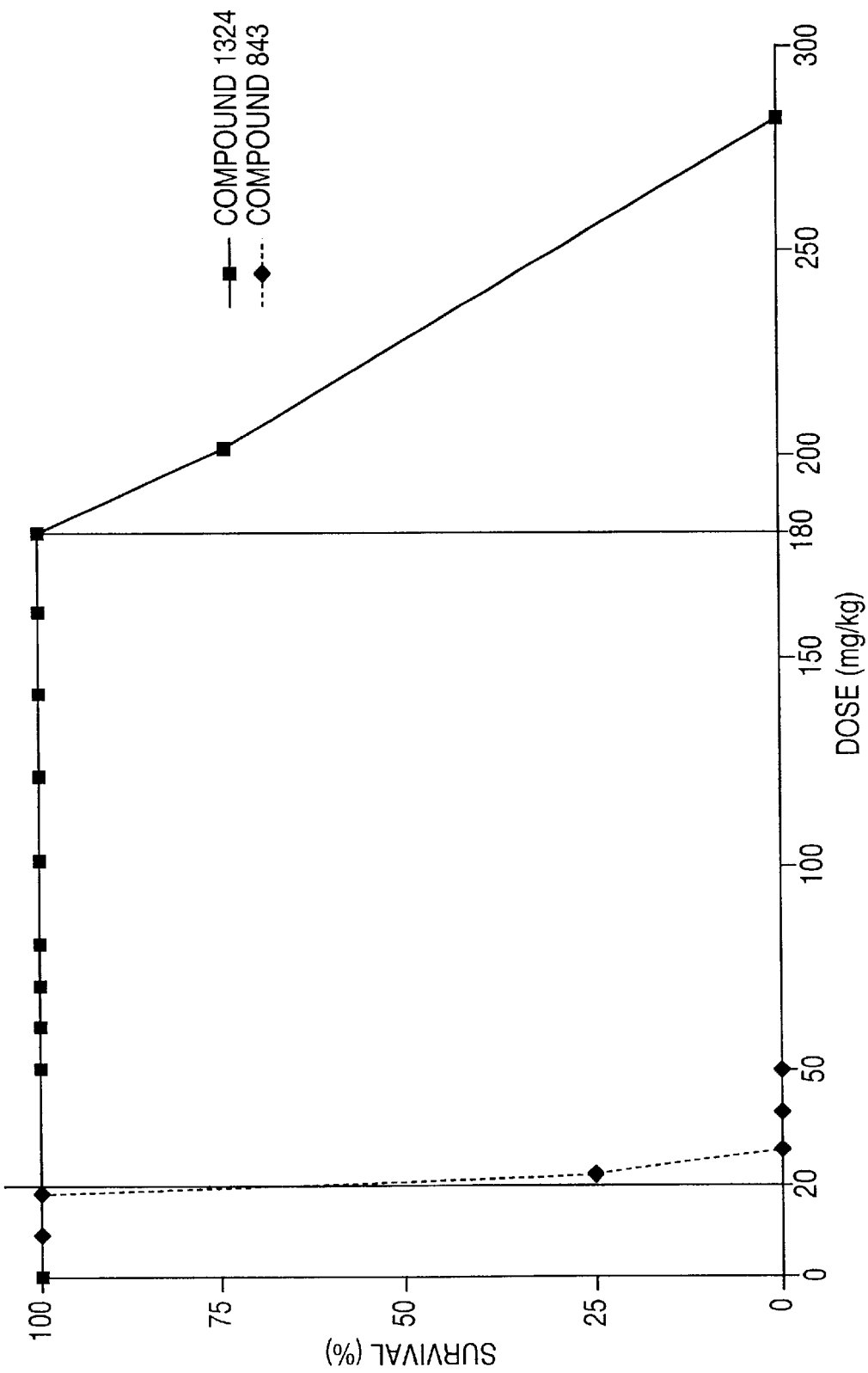
FIG. 1 is a graphical comparison of the maximum tolerated dose of Compound 843 and its methane sulfonate derivative, Compound 1324 (see Example 8, Table VII).
Figure 2:
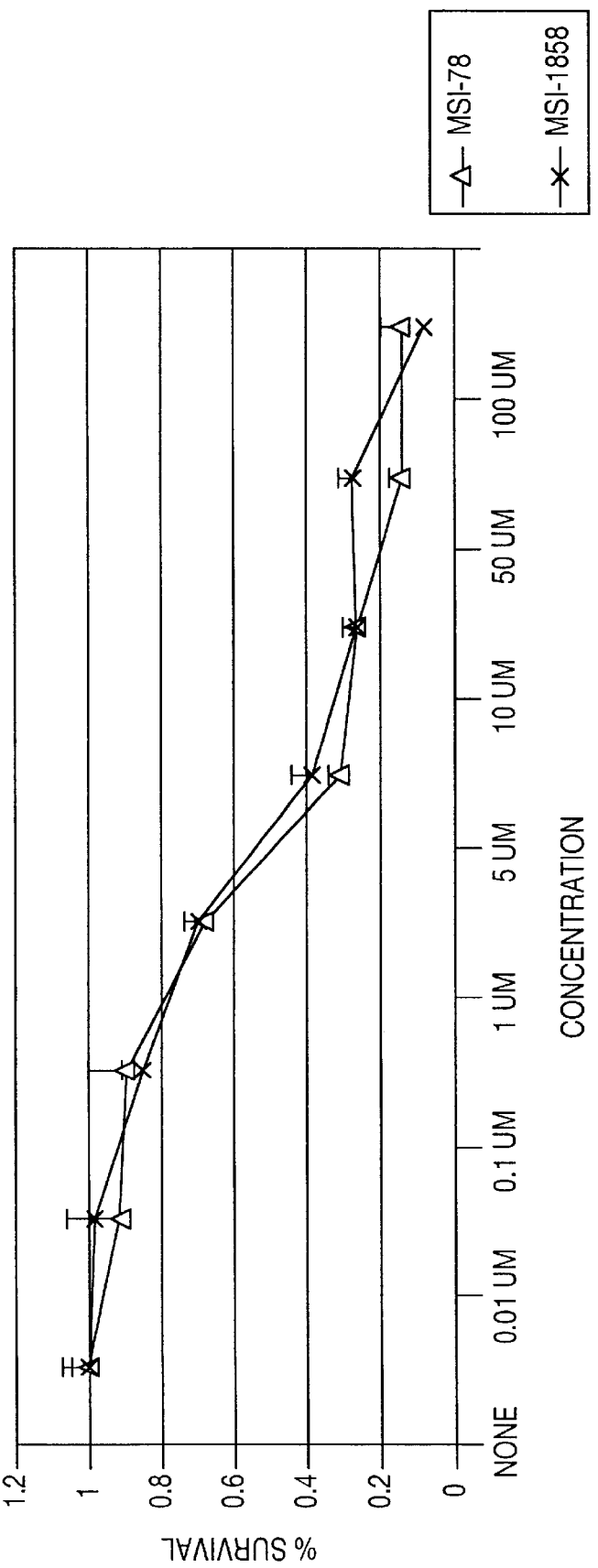
FIG. 2 is a survival curve for A-549 human lung carcinoma cells treated with MSI-78(SEQ ID NO: 154 —$NH_2$) and MSI-1858(SEQ ID NO: 154 —$NH_2$ methane sulfonate).
Figure 3:
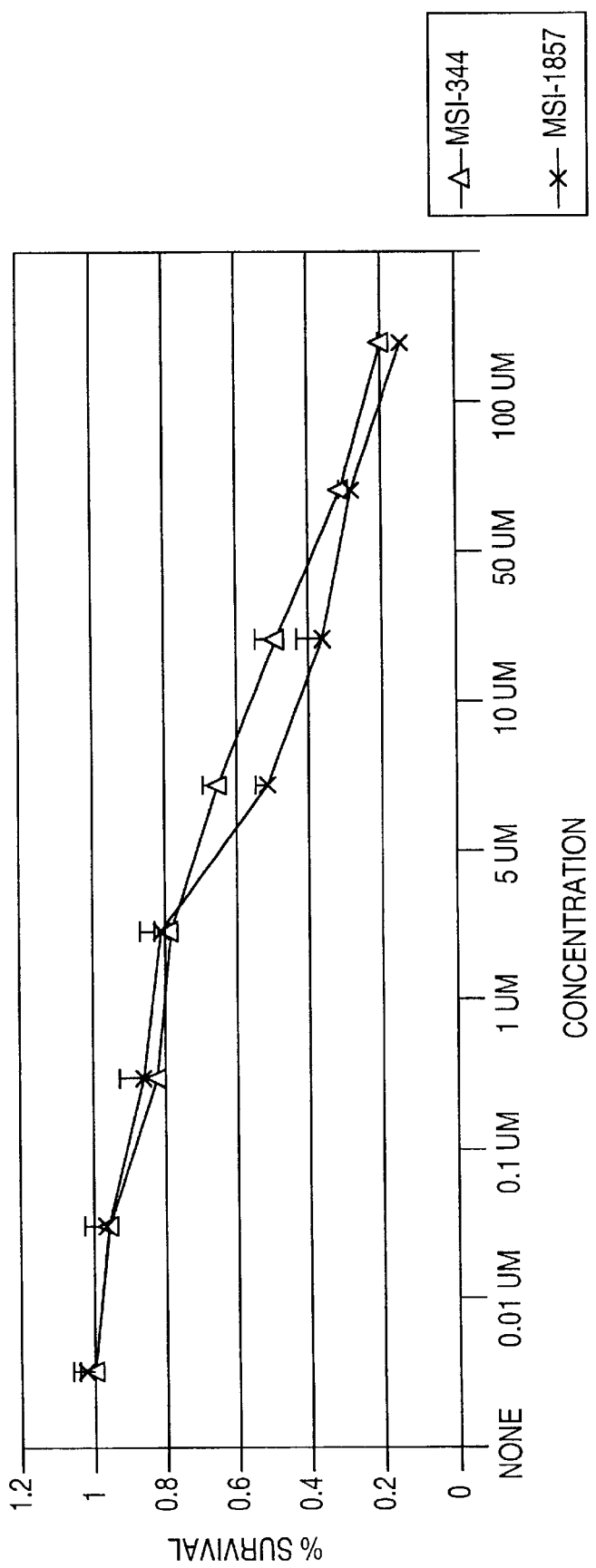
FIG. 3 is a survival curve for A-549 human lung carcinoma cells treated with MSI-344(SEQ ID NO: 154 —OH) and MSI-1857(SEQ ID NO: 154 —OH methane sulfonate).
Figure 4:
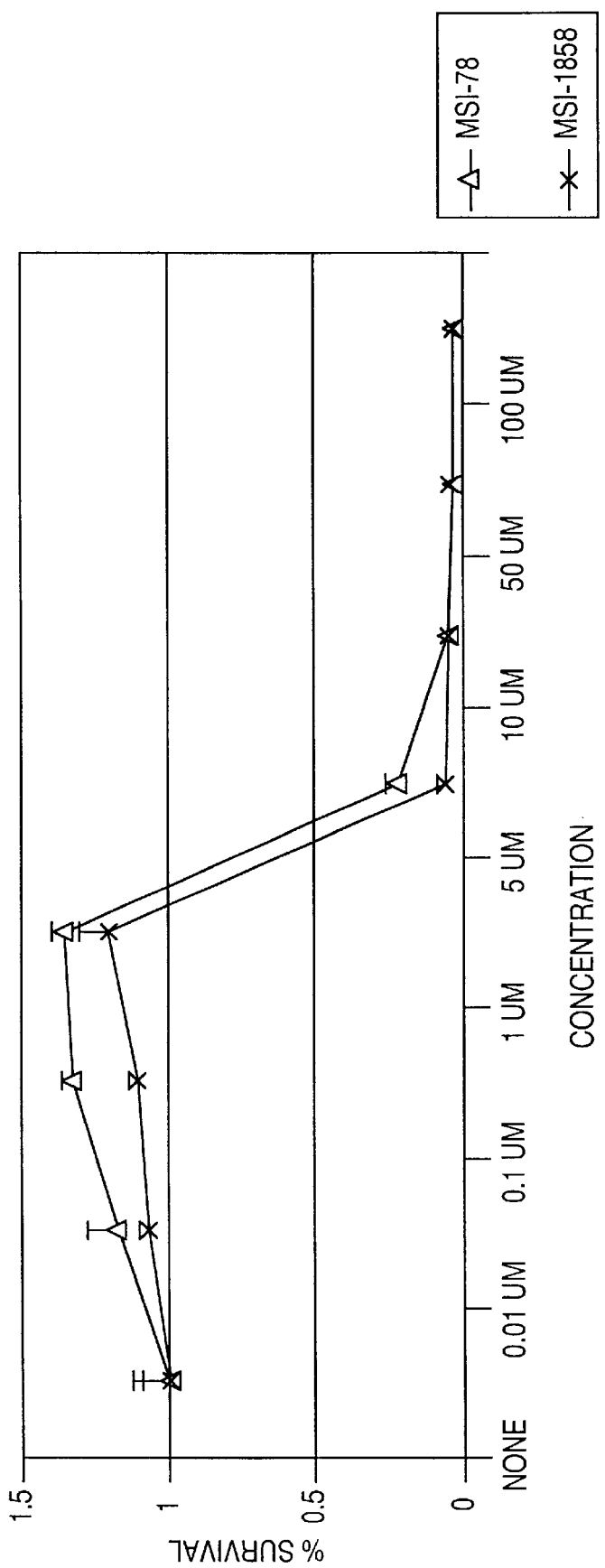
FIG. 4 is a survival curve for MDA-435 human breast carcinoma cells treated with MSI-78(SEQ ID NO: 154 —$NH_2$) and MSI-1858(SEQ ID NO: 154 —$NH_2$ methane sulfonate).
Figure 5:
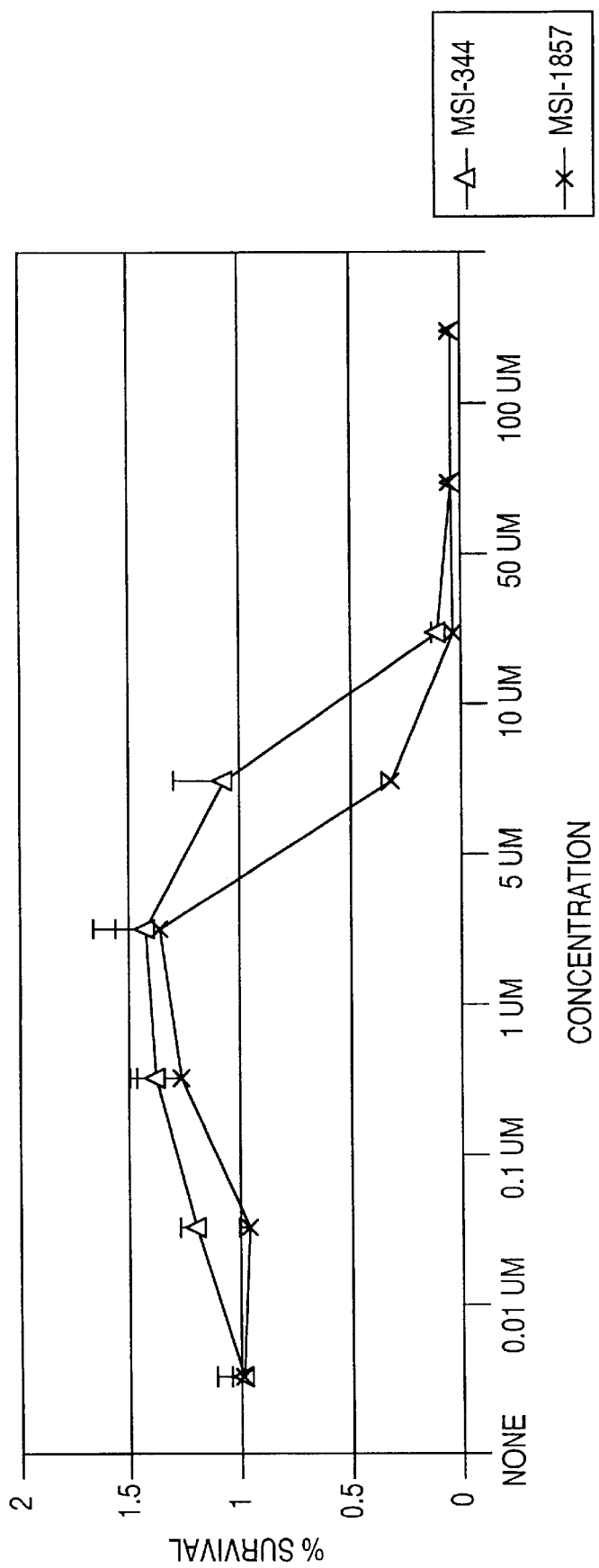
FIG. 5 is a survival curve for MDA-435 human breast carcinoma cells treated with MSI-344(SEQ ID NO: 154 —OH) and MSI-1857(SEQ ID NO: 154 —OH methane sulfonate).
Figure 6:
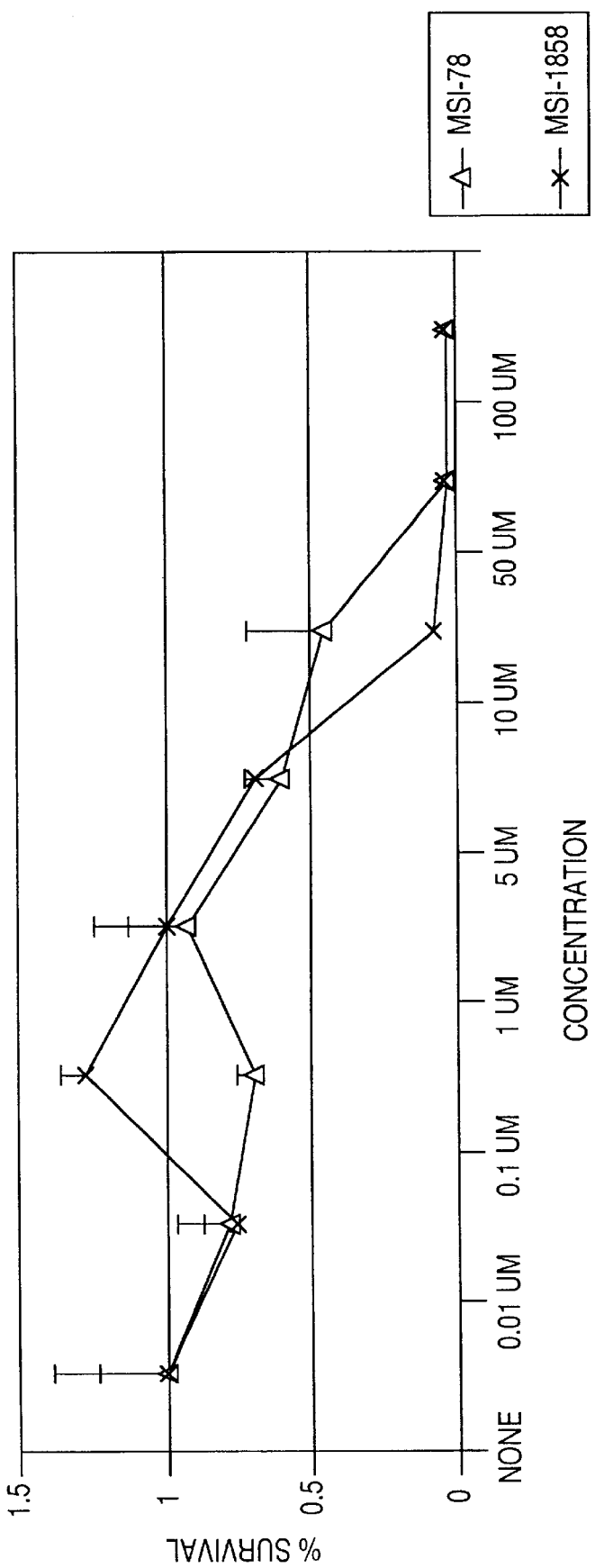
FIG. 6 is a survival curve for K-562 human chronic myelogenous leukemia cells treated with MSI-78(SEQ ID NO: 154 —$NH_2$) and MSI-1858(SEQ ID NO: 154 —$NH_2$ methane sulfonate).
Figure 7:
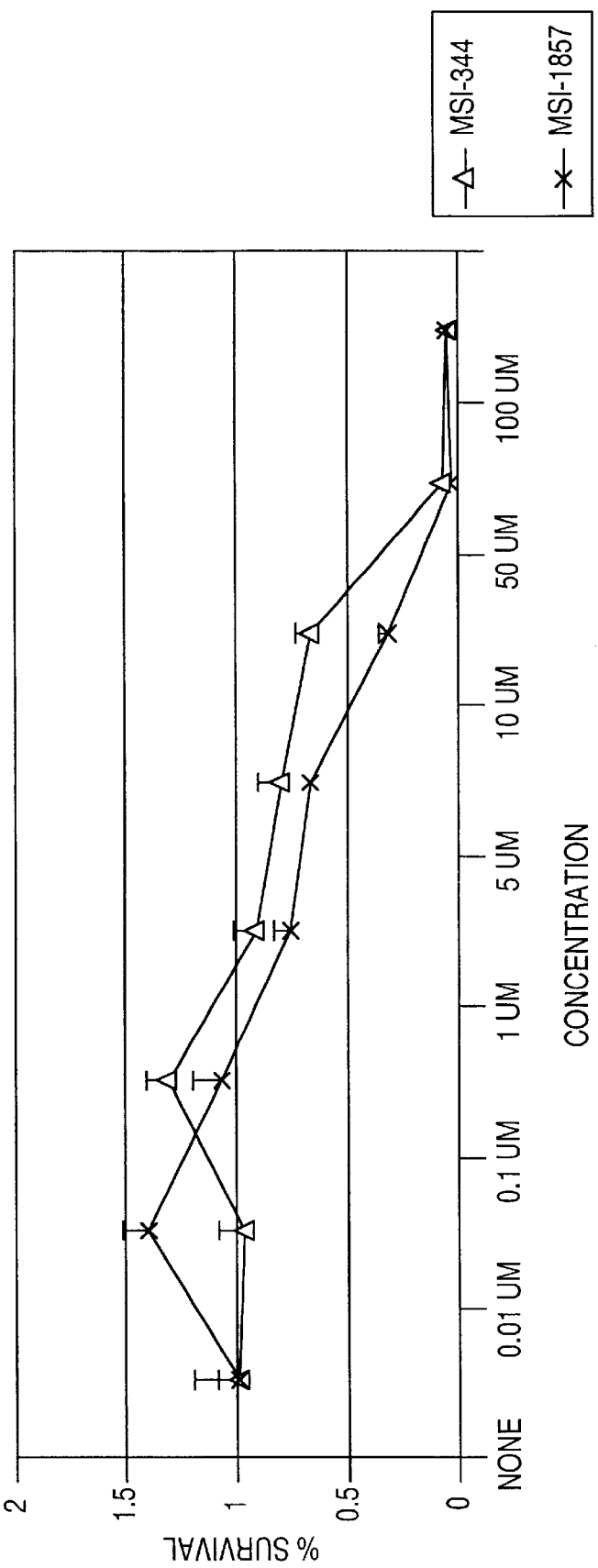
FIG. 7 is a survival curve for K-562 human chronic myelogenous leukemia cells treated with MSI-344(SEQ ID NO: 154 —OH) and MSI-1857(SEQ ID NO: 154 —OH methane sulfonate).
Figure 8:
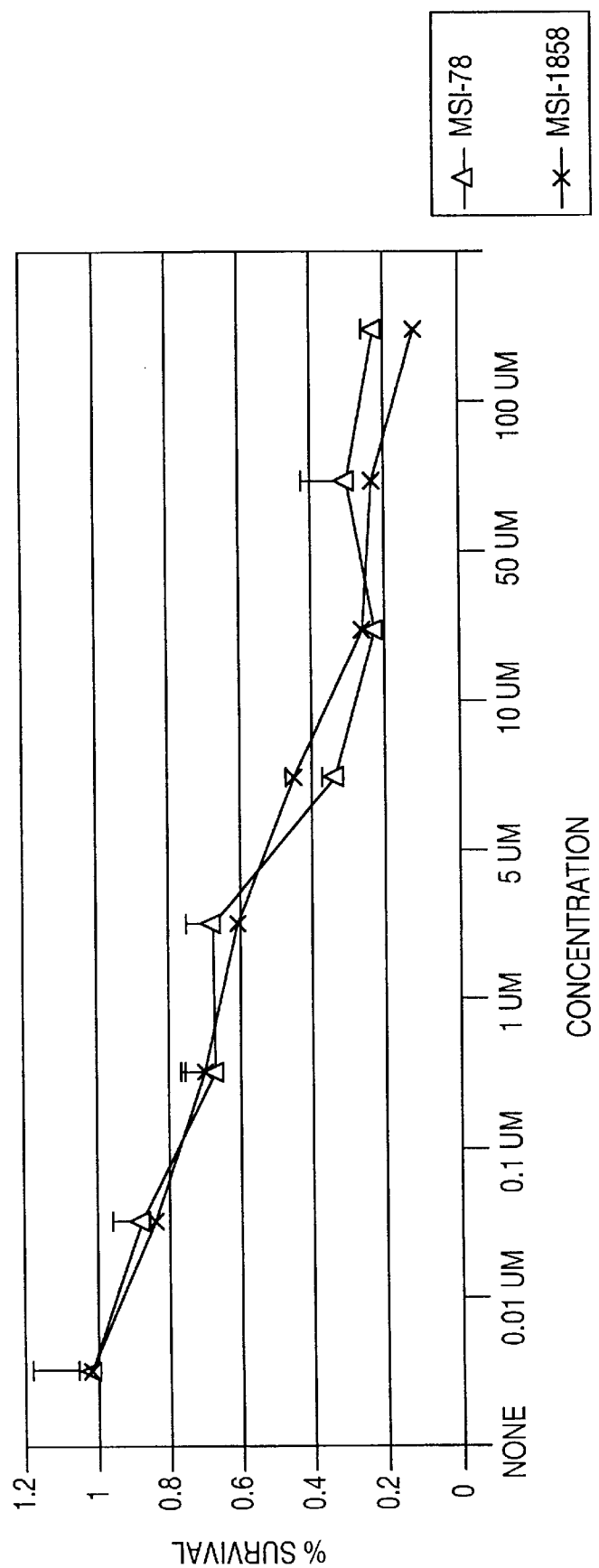
FIG. 8 is a survival curve for WM 1617 human melanoma cells treated with MSI-78(SEQ ID NO: 154 —$NH_2$) and MSI-1858(SEQ ID NO: 154 —$NH_2$ methane sulfonate).
Figure 9:
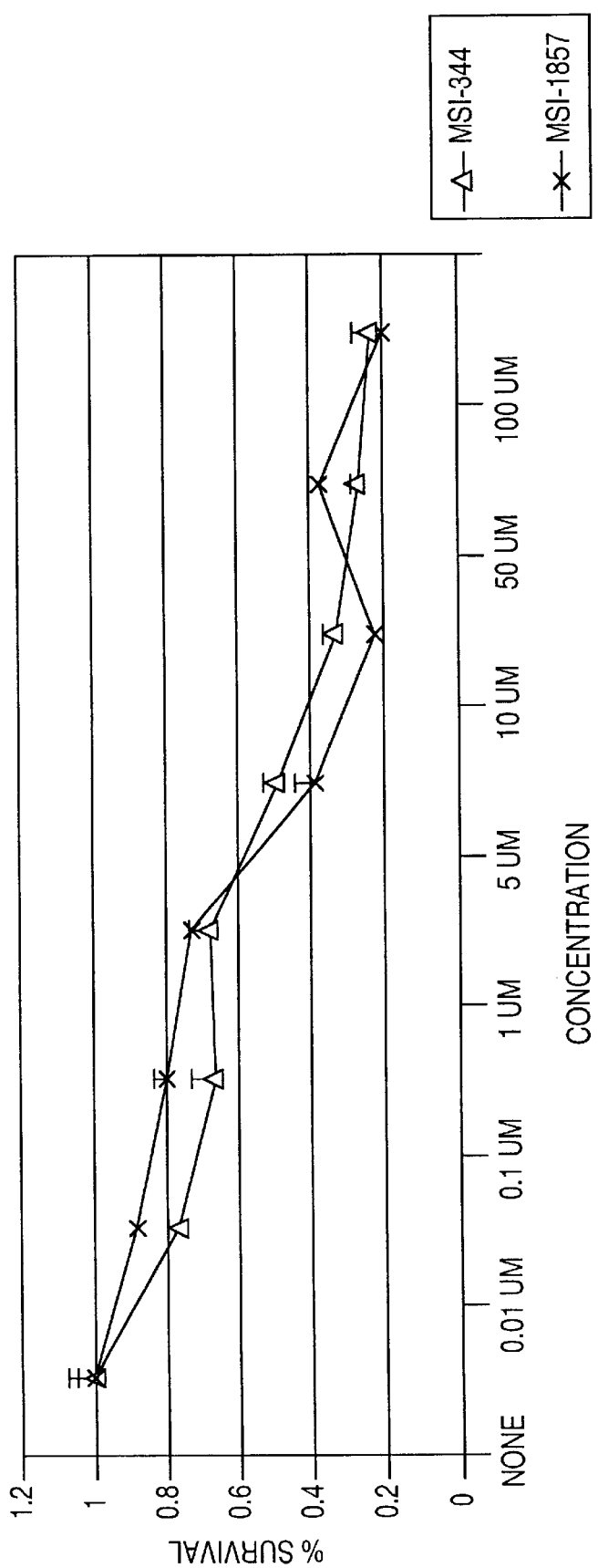
FIG. 9 is a survival curve for WM 1617 human melanoma cells treated with MSI-344(SEQ ID NO: 154 —OH) and MSI-1857(SEQ ID NO: 154 —OH methane sulfonate).

The present invention will be further described in the following specific examples. These examples should be construed as illustrating the invention and not as limiting the same.

EXAMPLE 1

Table I, which follows, indicates the Minimal Inhibitory Concentration (MIC) in pg/ml of various peptides against *S.aureus* strain ATCC 25923(S), *P. aeruginosa* strain ATCC 27853(P), *E. coli* ATCC strain 25922(E), and *C. 4albicans* (CA). A "D" indicates that each amino acid residue is a D-amino acid residue or a glycine residue. The peptides are unsubstituted at the N-terminal; substituted with an acetyl group at the N-terminal, as indicated by Ac-; substituted with an octanoyl group at the N-terminal, as indicated by Oct-; substituted with spinogosine, as indicated by Sph-; substituted with a succinyl group, as indicated by Suc-; substituted with a hexanoyl group, as indicated by Hex-; substituted with a heptanoyl group, as indicated by Hep-; substituted with a valeryl group, as indicated by Val-; substituted with a myristryl group, as indicated by Myr-; or substituted with an ibuprofyl group, as indicated by Ibu-;

The procedure for the anti-bacterial assay is based upon the guidelines of the National Committee for Clinical Laboratory Standards, Document M7-T2, Volume 8, No. 8, 1988, which document is entirely incorporated herein by reference.

Stock solutions of peptides, with and without the appropriate substitutions, were prepared at a concentration of 512 µg/ml in sterile deionized distilled water and stored at −70° C.

The stock peptide solution was diluted in serial dilutions (1:2) down the wells of a microtiter plate so that the final concentrations of peptides in the wells were 0.25, 0.50, 1, 2, 4, 8, 16, 32, 64, 128 and 256 µg/ml. 1–5×10$^5$ CFUs/ml of either *S. aureus* ATCC 25923, *E. coli* ATCC 25922, *P. aeruginosa* ATCC 27853, or *C. albicans*, were added to the wells in full strength Mueller Hinton broth (BBL 11443) from a mid-log culture. The inoculum was standardized spectrophotometrically at 600 nm and was verified by colony counts. The plates were incubated for 16–20 hours at 37° C., and the minimal inhibitory concentration (MIC) for each peptide was determined. Minimal inhibitory concentration is defined as the lowest concentration of peptide which produces a clear well in the microtiter plate. The minimal inhibitory concentration of each of the peptides with and/or without the appropriate substitutions is given in Table I below.

TABLE I

Minimal Inhibitory Concentration (µg/ml)

| Peptide | S | P | E | CA |
|---|---|---|---|---|
| Oct-(SEQ ID NO: 27)-NH2 | 2 | 4 | 2 | 16 |
| Oct-(SEQ ID NO: 27)-OH | 8 | 8 | 4 | 32 |
| Ac-(SEQ ID NO: 27)-NH2 | 32 | 128 | 8 | N/A |
| (SEQ ID NO: 27)-NH2 | 8,16 | 64,128 | 8 | N/A |
| (SEQ ID NO: 27)-OH | 128 | 128 | 8 | N/A |

TABLE I-continued

Minimal Inhibitory Concentration (µg/ml)

| Peptide | S | P | E | CA |
|---|---|---|---|---|
| Sph-Suc-(SEQ ID NO: 27)-NH2 | 64 | >256 | 32 | N/A |
| Suc-((SEQ ID NO: 27)-NH2 | >256 | >256 | 32 | 128 |
| Peptide | S | P | E | CA |
| Ibu-(SEQ ID NO: 27)-NH2 | 2 | 4 | 8 | 128 |
| (SEQ ID NO: 66)-NH2 | 4 | 32 | 32 | 64 |
| Oct-(SEQ ID NO: 66)-NH2 | 4 | 16 | 8 | 256 |
| (SEQ ID NO: 86)-OH | 128 | 32 | 2 | 256 |
| Oct-(SEQ ID NO: 86)-OH | 8 | 4 | 2 | 128 |
| Oct-(SEQ ID NO: 106)-NH2 | 128 | 32,64 | 128 | 64,128 |
| Oct-(SEQ ID NO: 107)-NH2 | 128 | 256 | >256 | 128 |
| Oct-(SEQ ID NO: 108)-NH2 | 16 | 4 | 64 | 64 |
| Oct-(SEQ ID NO: 109)-NH2 | 8 | 4 | 16 | 32 |
| (SEQ ID NO: 110)-NH2 | >256 | 32,64 | 64,128 | N/A |
| Ac-(SEQ ID NO: 110)-NH2 | 256 | 8,16 | 32,64 | N/A |
| Oct-(SEQ ID NO: 110)-NH2 | 4 | 4 | 8 | 32 |
| Oct-D-(SEQ ID NO: 110)-NH2 | 4 | 4 | 16 | 32 |
| Hex-(SEQ ID NO: 110)-NH2 | 16 | 8 | 16 | 64 |
| Hep-(SEQ ID NO: 110)-NH2 | 8 | 4 | 16 | 32 |
| Val-(SEQ ID NO: 110)-NH2 | 64 | 8 | 32 | 32 |
| Myr-(SEQ ID NO: 110)-NH2 | 16 | 16 | 16 | >256 |
| Oct-(SEQ ID NO: 111)-NH2 | 64 | 8 | 32 | 32 |
| (SEQ ID NO: 113)-NH2 | 16,32 | 8,16 | 32 | N/A |
| Ac-(SEQ ID NO: 113)-NH2 | 32 | 64 | 64 | N/A |
| Oct-(SEQ ID NO: 113)-NH2 | 8 | 8 | 8 | 128 |
| Oct-(SEQ ID NO: 118)-NH2 | >256 | >256 | >256 | >256 |
| Oct-(SEQ ID NO: 119)-NH2 | >256 | >256 | >256 | >256 |
| Oct-(SEQ ID NO: 120)-NH2 | 64 | 128 | 256 | 64 |
| Oct-(SEQ ID NO: 121)-NH2 | 128 | 256 | 256 | 256 |
| Oct-(SEQ ID NO: 122)-NH2 | 32 | 32 | 64 | 64 |
| Oct-(SEQ ID NO: 123)-NH2 | 32 | 16 | 32 | 32 |
| Peptide | S | P | E | CA |
| Oct-(SEQ ID NO: 124)-NH2 | 128 | 64 | 256 | 128 |
| Oct-(SEQ ID NO: 125)-NH2 | 8 | 8 | 16 | 64 |
| Oct-(SEQ ID NO: 126)-NH2 | 8 | 8 | 8 | 64 |
| Oct-(SEQ ID NO: 127)-NH2 | >256 | 32 | 32 | 128 |
| Oct-(SEQ ID NO: 128)-NH2 | 128 | 64 | 32 | 32 |
| Oct-(SEQ ID NO: 129)-NH2 | 128 | 16 | 32 | 128 |
| Oct-(SEQ ID NO: 130)-NH2 | 4 | 4 | 4 | 8 |
| Oct-(SEQ ID NO: 131)-NH2 | 8 | 8 | 4 | 64 |
| Oct-(SEQ ID NO: 132)-NH2 | 32 | 8 | 8 | 64 |
| Oct-(SEQ ID NO: 133)-NH2 | 16 | 32 | 32 | 128 |
| Oct-(SEQ ID NO: 134)-NH2 | 64 | 8 | 16 | 64 |
| Oct-(SEQ ID NO: 135)-NH2 | 32 | 8 | 64 | 64 |
| Oct-(SEQ ID NO: 136)-NH2 | 256 | 64 | 256 | 256 |
| Oct-(SEQ ID NO: 137)-NH2 | 256 | 256 | >256 | 256 |
| Oct-(SEQ ID NO: 138)-NH2 | 4 | 8 | 8 | 64 |
| Oct-(SEQ ID NO: 139)-NH2 | 16 | 32 | 16 | 128 |
| Oct-(SEQ ID NO: 140)-NH2 | 32 | 8 | 16 | 64 |
| Oct-(SEQ ID NO: 141)-NH2 | 4 | 4 | 8 | 32 |
| Oct-(SEQ ID NO: 142)-NH2 | 4 | 2 | 8 | 32 |
| Oct-(SEQ ID NO: 143)-NH2 | 16 | 2 | 16 | 16 |
| Oct-(SEQ ID NO: 144)-NH2 | 8 | 4 | 16 | 32 |
| Oct-(SEQ ID NO: 145)-NH2 | 4 | 8 | 16 | 64 |
| Oct-(SEQ ID NO: 146)-NH2 | 8 | 4 | 16 | 32 |
| Oct-(SEQ ID NO: 147)-NH2 | 32 | 32 | 32 | 128 |
| Oct-(SEQ ID NO: 148)-NH2 | 32 | 8 | 32 | 128 |
| (SEQ ID NO: 149)-NH2 | 256 | 32 | 32 | 64 |
| Oct-(SEQ ID NO: 149)-NH2 | 64 | 16 | 32 | 126 |
| Peptide | S | P | E | CA |
| Hex-(SEQ ID NO: 150)-NH2 | 16 | 128 | 32 | 128 |
| Myr-(SEQ ID NO: 151)-NH2 | 64 | 128 | 64 | >256 |
| Oct-(SEQ ID NO: 153)-NH2 | 8 | 8 | 32 | 64 |

The above results indicate that when a biologically active peptide is substituted with a lipophilic moiety of the present invention, the peptide has increased biological activity against a variety of microorganisms.

EXAMPLE 2

Stock cultures of *P. gingivalis*, *S. mutans*, or *A. viscosus* were maintained on Brucella blood agar plates with hemin and vitamin K$_1$ (BBL, Cockeysville, Md.) and were grown under anaerobic conditions (Coy Anaerobic Chamber, Ann Arbor, Mich.) with an atmosphere of 80% $N_2$-10%$H_2$-10%$CO_2$ at 37° C. Experimental cultures were grown up in Brain heart infusion (BHI) broth (BBL, Cockeysville, Md.), plus hemin (2.5 mg/liter) (Sigma Chemical Co., St. Louis, Ill.), plus vitamin $K_1$ (0.25 mg/liter) (Sigma Chemical Co., St. Louis, Mo.). For susceptibility testing, cultures were taken from overnight (24 hour) broth cultures and diluted in fresh BHI broth (plus hemin plus vitamin $K_1$) to deliver $1 \times 10^6$ colony-forming units (CFUs)/ml in each microtiter test well.

Anti-microbial susceptibility tests were performed according to the guidelines of the National Committee for Clinical Laboratory Standards (NCCLS) (Document M11-T2, 1989, incorporated herein by reference). Microtiter plates (Corning, Corning, N.Y.) were filled aseptically with BHI broth (plus hemin plus vitamin $K_1$) to a volume of 100 $\mu$l by the use of a Beckman Biomek 1000 robotic instrument (Beckman Instruments, Palo Alto, Calif.). Peptides were tested in duplicate lanes by adding manually 100 $\mu$l of a 1.024 mg/ml peptide solution in water (w/v) to the top wells of a microtiter plate lane. The peptide was diluted serially 1:2 by mixing and transferring 100 $\mu$l from the top well down to the bottom well in the lane by use of the Beckman Biomek 1000 (Beckman Instruments, Palo Alto, Calif.). The last 100 $\mu$l from the bottom well was discarded. One hundred microtiters of the bacteria were added in BHI (plus hemin plus vitamin $K_1$) to each test well to give final peptide dilutions from 0.25 $\mu$l/ml. The plates were incubated in the anaerobic chamber at 37° C. for 24–48 hours. After incubation, the minimum inhibitory concentration (MIC) was determined as the lowest concentration of peptide which inhibits growth as determined by visual inspection and optical density when read on a Dynatech $MR_{5000}$ microtiter plate reader at 630 nm (Dynatech Laboratories, Chantilly, Va.). The results are given in Table II below.

$\mu$g/mouse) from *E. coli* serotype 0111:B4 and galactosamine (8 mg/mouse). Treatment doses of Oct-(SEQ ID NO: 143)—$NH_2$ were 0, 5, 7.5, 10, 12.5 or 15 mg/kg (10 mice/group), and when administered prior to 0.5 $\mu$g lipopolysaccharide/mouse resulted in 10%, 0%, 30%, 0%, 50%, and 60% survival at five days post-lipopolysaccharide administration, respectively. When these doses were administered prior to the administration of 0.1 $\mu$g lipopolysaccharide/mouse, the results were 40%, 90%, 100%, 100%, and 100% survival at five days post-lipopolysaccharide administration, respectively.

EXAMPLE 5

A stock solution (10×) of 0.6 mM dye was prepared by adding 1.68 mg of (1-ethyl-2-(3-[1-ethylnaphthol (1,2-d)-thiazolin-2-ylidene] -2-methylpropenyl)naphtho-(1,2-d)-thiazolium bromide (Signa E-7762) to 5 ml of 200 proof ethanol. 1 ml of this solution was added to 9 ml ethanol to give 0.06 mM of dye (60 $\mu$M dye).

A stock solution of lipopolysaccharide (LPS) from *E. coli* serotype 0111:B4 was prepared at 1.5 mg/ml. 400 $\mu$l of this solution was mixed with 4.6 ml pyrogen free water to give a 120 $\mu$g/ml solution.

Row 1 and rows 3 through 12 of a microtiter plate were filled with 100 $\mu$l of pyrogen free water or with 10 mg/ml of bovine serum albumin. 200 $\mu$l of peptide then was added to row 2 of the microtiter plate at a concentration of 1 mg/ml. 200 $\mu$l of pyrogen free water was added to each of the control wells in two lanes (having dye and LPS but no peptide or having dye and no LPS and no peptide). 100 $\mu$l then was serially diluted from row 2 through row 12 of the microtiter plate. 50 $\mu$l of PBS (pH 7.4) and 50 $\mu$l of the LPS solution then were added to row 1 of the plate (blank wells).

Equal volumes of the LPS solution, the dye, and PBS (pH 7.4 approx. 150 mM) were mixed to form a dye-buffer-LPS

TABLE II

| | MIC ($\mu$l/ml) | | | | | | |
| | *P. gingivalis* (strain) | | | | | | |
| Peptide | 381 | A7A1-28 | FAY-19M-1 | 9-14K-1 | 450 | S. mutans | A. viscos |
| --- | --- | --- | --- | --- | --- | --- | --- |
| (SEQ ID NO. 27)-$NH_2$ | 128 | 16 | 64 | 8,128 | 4 | 16 | 16 |
| Oct-(SEQ ID NO. 27)-$NH_2$ | 16 | 4 | 4 | 4 | 16 | 16 | 16 |
| Oct-(SEQ ID NO. 27)-OH | 2 | 1 | 2 | 2 | 1 | 16 | 32 |
| (SEQ ID NO. 66)-$NH_2$ | 16 | 4 | 8 | 2 | 4 | 8 | 8 |
| Oct-(SEQ ID NO. 66)-$NH_2$ | 4 | 8 | 2 | 2 | 2 | 32 | 16 |
| (SEQ ID NO. 86)-$NH_2$ | 8 | 2 | 8,128 | 8 | 4 | 4 | 16 |
| (SEQ ID NO. 86)-OH | 16 | 4 | 8 | 16 | 4 | 16 | 32 |
| Oct-(SEQ ID NO. 86)-OH | 1 | 1 | 1 | 1 | 1 | 16 | 32 |

EXAMPLE 3

CD-1 male mice (average body weight, 22.8g) were inoculated with live *E. coli* strain 21915-1 ($2.3 \times 10^5$ CFU mouse) by injection intraperitoneally. Oct-(SEQ ID NO: 143)—$NH_2$ then was injected intravenously via the tail vein at 1 and 5 hours post-inoculation. Control mice were inoculated and treated with 0.9% saline. Each different treatment group had 10 mice per group. All control mice died. Treatment doses of Oct-(SEQ ID NO: 143)—$NH_2$ were 1, 5, 10 and 20 mg/kg in toto, and resulted in 20%, 40%, 90% and 90% survival at six days post-inoculation, respectively.

EXAMPLE 4

Oct-(SEQ ID NO: 143)—$NH_2$ was injected intravenously into male C57BL/6J mice (average body weight 20.1 g) approximately two minutes prior to intraperitoneal injection of a solution of lipopolysaccharide (either 0.1 $\mu$g or 0.5 mixture having LPS at a final concentration of 40 $\mu$g/ml and dye at a final concentration of 20 $\mu$M. The dye-buffer LPS mixture then was incubated for 10 minutes at room temperature in the dark.

100 $\mu$l of the dye-LPS buffer mixture then was added to every well of the microtiter plate except to the blank wells and to the control lane that does not have LPS or peptide. The plate was incubated for 10 minutes at room temperature in the dark, and the absorbance at 460 nm and 510 nm was read. From these absorbances, the LPS50 value, which is the concentration in mg/ml of peptide necessary to inhibit the binding of 50% of the lipopolysaccharide to the dye, was calculated.

The above procedure was carried out for the peptides listed in Table III below and demonstrates that N-terminally modified anti-microbial peptides can also inhibit the binding of LPS to a hydrophobic dye.

TABLE III

| Compound | LPS 50 |
| --- | --- |
| Oct-(SEQ ID NO: 106)-NH2 | 6.80 |
| Oct-(SEQ ID NQ: 107)-NH2 | 15.00 |
| Oct-(SEQ ID NO: 109)-NH2 | 0.60 |
| Oct-(SEQ ID NO: 110)-NH2 | 0.84 |
| Oct-D(SEQ ID NO: 110)-NH2 | 0.97 |
| Oct-(SEQ ID NO: 111)-NH2 | 1.00 |
| Oct-(SEQ ID NO: 121)-NH2 | 20.00 |
| Oct-(SEQ ID NO: 123)-NH2 | 1.70 |
| Oct-(SEQ ID NO: 137)-NH2 | 4.80 |
| Oct-(SEQ ID NO: 138)-NH2 | 1.00 |
| Oct-(SEQ ID NO: 142)-NH2 | 0.70 |
| Oct-(SEQ ID NO: 143)-NH2 | 0.90 |

EXAMPLE 6

General Method for the Preparation of Sodium Methane Sulfonate Derivatives of N-Terminally Modified Peptides The free base of an N-terminally modified peptide was generated by neutralizing the acetate or trifluoroacetate salt with saturated sodium carbonate solution. The precipitated peptide was isolated either by centrifugation or by filtration, followed by washing with water. A formaldehyde-sodium bisulfite complex was prepared by dissolving 5 gm of sodium bisulfite in a mixture of 75 ml of water and 4 ml of 35–40% formaldehyde with stirring. The solution was cooled and ethanol added. The precipitate obtained was filtered, washed with water, and dried. The product was recrystallized from water-ethanol. The peptide free base was suspended in water and Formaldehyde-sodium bisulfite complex (Aldrich #11, 270-4; Milwaukee, Wis.) (1.1–3.0 equivalents for each free amino group) was added slowly while stirring the reaction mixture. After stirring for about 15–30 minutes, the solution was filtered and lyophilized.

EXAMPLE 7

The in vitro anti-microbial activities of the methane sulfonate derivatives were determined according to the methods described in Examples 1 and 2. The activities against ATCC strains of S. aureus, E. coli, P. aeruginosa, and C. albicans, and the hemolysis of red blood cells were compared to the parent compound (Table IV). The activities for Compound 843 (Oct-SEQ ID NO:143) methane sulfonate against clinical strains of P. aeruginosa isolated from cystic fibrosis patients were compared to the parent compound (Table V). The activity for Compound 469 (Oct-SEQ ID NO:27) methane sulfonate against P. gingivalis was compared to the parent compound (Table VI). These results indicate that the methane sulfonate analogues have anti-microbial activities comparable to the parent compounds.

TABLE IV

Anti-microbial Activity of Methane Sulfonate Derivatives Compared to Parent Compound
MIC (µg/ml)

| Compound | S. aureus ATCC 29213 | E. coli ATCC 25922 | P. aeruginosa ATCC 27853 | C. albicans ATCC 90028 | % Hemolysis (500 µg/ml) |
| --- | --- | --- | --- | --- | --- |
| OCT-SEQ ID NO: 143-NH$_2$ sodium methane sulfonate derivative | 8 | 8 | 2 | 64 | 2% |
| OCT-SEQ ID NO: 143-NH$_2$ | 16 | 4 | 2 | 64 | 25% |
| OCT-SEQ ID NO: 27-NH$_2$ sodium methane sulfonate derivative | 4 | 8 | 32 | 64 | 75% |
| OCT-SEQ ID NO: 27-NH$_2$ | 2 | 4 | 4-8 | 64 | 100% |
| SEQ ID NO: 154-NH$_2$ sodium methane sulfonate derivative | 32 | 32 | 32-64 | ND | ND |
| SEQ ID NO: 154-NH$_2$ | 16 | 32 | 16-32 | ND | ND |
| SEQ ID NO: 154-OH sodium methane sulfonate derivative | 128 | 32 | 256 | ND | ND |
| SEQ ID NO: 154-OH | 128 | 8 | 16 | ND | ND |
| SEQ ID NO: 155-NH$_2$ sodium methane sulfonate derivative | 64 | 128 | 64 | ND | ND |
| SEQ ID NO: 155-NH$_2$ | 16 | 16 | 32 | ND | ND |

TABLE V

Activity of Compound 843 (Oct-SEQ ID NO:143)
Methane Sulfonate Derivatives
Against Clinical Isolates of P. aeruginosa
MIC (µg/ml)
Pseudomonas aeruginosa

| Compound | LS-31 | LS-40 | LS-43 | ATCC 27853 |
| --- | --- | --- | --- | --- |
| Parent Compound 843 | 16 | 4 | 2 | 4 |
| Compound 1324 (the methane sulfonate derivative of Compound 843) | 16 | 4 | 2 | 4 |

TABLE VI

Activity of Compound 469 (Oct-SEQ ID NO:27) and its Methane Sulfonate Analogue Against *P. gingivalis*

| Compound | MIC ($\mu$g/ml) *P. gingivalis* ATTC 33277 |
|---|---|
| Compound 1662 (the methane sulfonate of Compound 469) | 8 |
| Parent Compound 469 (Oct-KIAGKIA)$_3$-NH$_2$) | 4 |

EXAMPLE 8

Effect of Methane Sulfonate Addition on the Maximal Tolerated Dose of Compound 843 (Oct-SEQ ID NO:143) in Mice Summary Mice received single intravenous administrations of Compound 1324, the methane sulfonate analogue of Compound 843, and were monitored for survival for at least 4 days. There were no deaths at a dose of less than or equal to 180 mg/kg. This demonstrates that the chemical modification of Compound 843 to produce Compound 1324 results in a 9-fold increase in safety.

Objective

To determine the maximal tolerated dose (MTD) and estimate the lethal dose 50% (LD50) of Compound 1324 sodium when administered intravenously in a single-bolus in mice.

Materials and Methods

Animals: On arrival and study initiation, three groups Thirty-seven male CD-1 mice (Charles River Lab)had average body weights of 39, 28 and 28 gm, respectively.

Materials: Test article:

Compound 1324 active moiety 47%

Vehicle: 0.9% Saline

Solution Prep: A 120 mg/ml of active Compound 1324 (active moiety corrected for) was made in saline. All concentrations from 5 mg/ml to 80 mg/ml were dilutions of the 120 mg/ml solution with saline. The highest concentration used in the intravenous administration was 20 mg/ml.

Protocol

Mice were randomly assigned to one of ten groups (4 mice per group, except the highest dose group which only had one mouse). Mice were administered intravenously 10 ml/kg of either 0 (saline), 5, 6, 7, 8, 14, 16, 18, or 20 mg/ml solution for doses of 0, 50, 60, 70, 80, 140, 160, 180, 200 mg/ml. One mouse received 14.1 ml/kg of a 20 mg/ml solution for a dose of 282 mg/kg. Mice were monitored for survival for at least four days post-administration.

Results

See the Survival Table, Table VII.

All mice that were intravenously administered Compound 1324 at doses up to and including 180 mg/kg survived. Three of four mice that received 200 mg/kg survived. One mouse that received 200 mg/kg and one mouse that received 282 mg/kg died.

TABLE VII

MTD = maximum tolerated dose (non-lethal)
LD50 = dose that was lethal to 50% of the animals
MTD i.v. = 1180 mg/kg
LD50 i.v. = between 200 and 282 mg/kg
For comparison, Compound 843 (the parent compound of Compound 1324) has a significantly lower MTD of 20.0 mg/kg. The chemical modification of Compound 843 yields Compound 1324 and produces a 9-fold increase in safety (see FIG. 1).

| Route | Dose (mg/kg) | No. of mice | Number of Survivors on Day | | | | | | |
|---|---|---|---|---|---|---|---|---|---|
| | | | 0[a] | 1 | 2 | 3 | 4 | 5 | 6 | 7 |
| IV | 0 | 4 | 4 | 4 | 4 | 4 | 4 | 4 | SE | SE |
| | 50 | 4 | 4 | 4 | 4 | 4 | 4 | 4 | SE | SE |
| | 60 | 4 | 4 | 4 | 4 | 4 | 4 | 4 | SE | SE |
| | 70 | 4 | 4 | 4 | 4 | 4 | 4 | 4 | SE | SE |
| | 80 | 4 | 4 | 4 | 4 | 4 | 4 | 4 | SE | SE |
| | 140 | 4 | 4 | 4 | 4 | 4 | 4 | 4 | ND | 4 |
| | 160 | 4 | 4 | 4 | 4 | 4 | 4 | 4 | ND | 4 |
| | 180 | 4 | 4 | 4 | 4 | 4 | 4 | 4 | ND | 4 |
| | 200 | 4 | ND | ND | 3 | 3 | 3 | SE | SE | SE |
| | 282 | 1 | ND | ND | 0 | 0 | 0 | SE | SE | SE |

ND = survival count not done
SE = study ended (terminated)
[a]Survivor count on Day 0 (the day they were dosed) was 2 or 6.5 hrs post-administration.

EXAMPLE 9

Alternate Method for the Preparation of Sodium Methane Sulfonate Derivatives of Cationic Peptides This method was used to prepare the sodium methane sulfonate derivatives of SEQ ID NOS: 154–156. The peptide salt (hydrochloride salt, acetate salt or trifluoroacetate salt) was taken into water and treated with an excess of 30% neutral formaldehyde solution(up to 12.5 equivalents for each amino group in the peptide) and an excess of 1M sodium bicarbonate solution(up to 6.25 equivalents for each amino group in the peptide). The precipitated peptide adduct of formaldehyde was separated either by centrifugation or by filtration, washed with water and dried. The formaldehyde adduct was suspended in water and an excess of sodium metabisulfite was added(up to 1.9 equivalents for each amino group in the peptide) to form the methane sulfomate derivative. The clear solution was filtered through a 0.2 $\mu$m filter and lyophilyzed.

Elemental analysis, mass spectra and antimicrobial activities were determined on these derivatives.

EXAMPLE 10

In Vitro Anti-Tumor Activity of Peptide Methane Sulfonate Derivatives Compared to Underivatized Peptides Cell Lines Human lung carcinoma cells, A-549 (ATCC), and human breast carcinoma cells, MDA-435 (from Sandoz), were grown in Ham's F12K medium (GIBCO-BRL) supplemented with 10t fetal bovine serum. Human chronic myelogenous leukemia cells, K-562 (ATCC), were maintained in RPMI 1640 medium (GIBCO-BRL) supplemented with 10% fetal bovine serum. Human melanoma cell line, WM 1617 (from the Wistar Institute), was maintained in 2% Tumor media.

Cytotoxicity Assay

Cytotoxicity assays were performed on the cell lines described above using CytoLite (Packard Instrument Company) following the manufacture's instruction. Briefly, $2\times10^4$ cells/well were seeded into black, 96-well ViewPlates (Packard Instrument Company) in 100 µl/well growth medium. Ser. dilutions of Magainin peptides were then added into the cells and the plates incubated for 24 hours in a humidified 5% $CO_2$ atmosphere at 37° C. Following incubation, 25 µl/well of CytoLite activator solution was added followed by 125 µl/well of amplifier solution. Luminescence was measured on TopCount Microplate Scintillation and Luminescence counter (Packard Instrument Company) using a 1 second count time in SPC (single photon counting) mode at 25 ° C. All assays were performed in triplicate. The peptides tested in this assay were MSI-78 (SEQ ID NO: 154 —$NH_2$), MSI-1858(SEQ ID NO: 154 —$NH_2$ Methane Sulfonate), MSI-344(SEQ ID NO: 154 —OH) and MSI-1857(SEQ ID NO: 154 —OH Methane Sulfonate). The results of these assays are shown in FIGS. 2–9 with the corresponding $IC_{50}$ values in Table VIII. In all cases the activity of the methane sulfonated peptide was as good or better than the parent peptide as indicated by both the survival curves and the $IC_{50}$ values.

Thymidine Uptake Assay $2\times10^4$ cells/well are seeded into 96-well tissue culture plates in 100 µl/well growth medium and allowed to attach overnight in a humidified 5% $CO_2$ atmosphere at 37° C. Ser. dilutions of Magainin peptides are then added into the cells and the plates are incubated for 18 hours. Following incubation, 0.2 µCi/well of [$^3$H]-thymidine are added to the plates and further incubated for 6 hours at 37° C. The cells are harvested, and the [$^3$H]-thymidine incorporation is determined by liquid scintillation counting. All assays are performed in triplicate.

TABLE VIII

Micro molar $IC_{50}$ Values for Peptides and the Corresponding Peptide Methane Sulfonates

|  | MSI-78 | MSI-78MS | MSI-344 | MSI-344MS |
|---|---|---|---|---|
| Melanoma | 3 | 4 | 5 | 3 |
| Lung Cancer | 3 | 4 | 10 | 6 |
| Breast Cancer | 4 | 4 | 8 | 4 |
| Leukemia | 9 | 7 | 20 | 7.5 |

MS = Methane Sulfonate

EXAMPLE 11

Study of the Maximal Tolerated Dose (MTD) for Single Administration (Intravenously or Intraperitoneally) of MSI- 344(SEQ ID NO: 154 —OH) and MSI-1857(SEQ ID NO: 154 —OH methane sulfonate) in Mice Summary Determinations of a maximal tolerated dose (MTD) of a single intravenous (i.v.) administration or intraperitoneal (i.p.) administration of MSI-344 or MSI-1857 in 100 CD-1®BR mice were done. The MTD of a single intravenous (i.v.) administration was 10 mg/kg for MSI-344 and 60 mg/kg for MSI-1857. The MTD of a single intraperitoneal (i.p.) administration was less than 20 mg/kg for MSI-344 and between 50 and 100 mg/kg for MSI-1857. The estimated LD50s (the dose that produces lethality in 50% of the animals injected) for intravenous administration were 12.5 and 73 mg/kg for MSI-344 and MSI-1857, respectively. The LD50s i.p. were 23.5 and 120 mg/kg for MSI-344 and MSI-1857, respectively. These data suggest that methane sulfonation of MSI-344 increases the safety of the compound administered in vivo approximately 5-fold when compared to MSI-344.

Objective

To determine estimates of MTDs and LD50s of MSI-344 and MSI-1857 administered intravenously or intraperitoneally as a single bolus in mice.

Materials and Methods

Animals 100 male CD-1®BR mice (Charles River Lab) arrived in two group and exhibited a body weight range of 20–26.3 gms at study initiation.

Solution Prep

A 5 mg/mL solution of MSI-344 was made in saline (0.9% sodium chloride injection USP, Abbott, North Chicago, Ill.) corrected for peptide content. Solutions of MSI-344 at concentrations of 4, 3, 2, 1.5, 1, and 0.5 mg/mL were made by diluting the 5 mg/mL solution using saline as diluent. (Errors were made in solution preparation of the 4, 3, and 2 mg/mL solutions and results from groups with animals doses with these solutions, i.e. groups 12, 13, and 14, were eliminated from study analysis). A 20 mg/mL solution of MSI-1857 was made in saline. Solutions of MSI-1857 at concentrations of 15, 10, 8, 6, and 5 mg/mL were made by diluting the 20 mg/mL solution using saline as diluent.

Another 5 mg/mL solution of MSI-344 was made in saline corrected for peptide content. Solutions of 4, 3 and 2 mg/mL were made by diluting the 5 mg/mL solution using saline as diluent. A 15 mg/mL solution of MSI-1857 in saline was made corrected for peptide content. A 10 mg/mL solution was made by diluting the 15 mg/mL solution with saline.

Protocol

Mice (four mice per dose group) were intravenously or intraperitoneally administered a single bolus of MSI-344 or MSI-1857 using an injection volume of 10 mL/kg of the appropriate solution concentration. If the first two mice in a group died immediately (within 10 secs) after administration of a dose then no other mice injected with this dose of this compound (for ethical reasons). Survival was monitored daily for at least eight days post-administration. Study designs are presented in Tables IX and X. Toxicity Study # 262 was a supplement to Toxicity Study #261.

TABLE IX

Study Design for Toxicity Study #261

| Group | Test Article | Dose (mg/kg) | Route of Administration | Number of Animals Injected |
|---|---|---|---|---|
| 1 | Saline | 0 | IV | 4 |
| 2 | MSI-344 | 20 |  | 2[a] |
| 3 |  | 15 |  | 2[a] |
| 4 |  | 10 |  | 4 |
| 5 |  | 5 |  | 4 |
| 6 | MSI-1857 | 100 |  | 4 |
| 7 |  | 80 |  | 4 |
| 8 |  | 60 |  | 4 |
| 9 |  | 50 |  | 4 |
| 10 | Saline | 0 | IP | 4 |
| 11 | MSI-344 | 50 |  | 4 |
| 12 |  | TBD[b] |  | 4 |
| 13 |  | TBD[b] |  | 4 |
| 14 |  | TBD[b] |  | 4 |
| 15 | MSI-1857 | 200 |  | 4 |

TABLE IX-continued

Study Design for Toxicity Study #261

| Group | Test Article | Dose (mg/kg) | Route of Administration | Number of Animals Injected |
|---|---|---|---|---|
| 16 | | 150 | | 4 |
| 17 | | 100 | | 4 |
| 18 | | 50 | | 4 |

[a]Only two of four mice were injected because of resulting immediate death; for ethical reasons the remaining two mice in this group were not injected.
[b]TBD = to be determined; there were errors made in solution preparation of these groups so concentration and dose were unknown; results from these groups were eliminated from analysis of this study.

TABLE X

Study Design for Toxicity Study #262

| Group | Test Article | Dose (mg/kg) | Route of Administration | Number of Animals Injected |
|---|---|---|---|---|
| 1 | Saline | 0 | IP | 4 |
| 2 | MSI-344 | 50 | | 4 |
| 3 | | 40 | | 4 |
| 4 | | 30 | | 4 |
| 5 | | 20 | | 4 |
| 6 | MSI-1857 | 150 | | 4 |
| 7 | | 100 | | 4 |

Results

Figure 10:
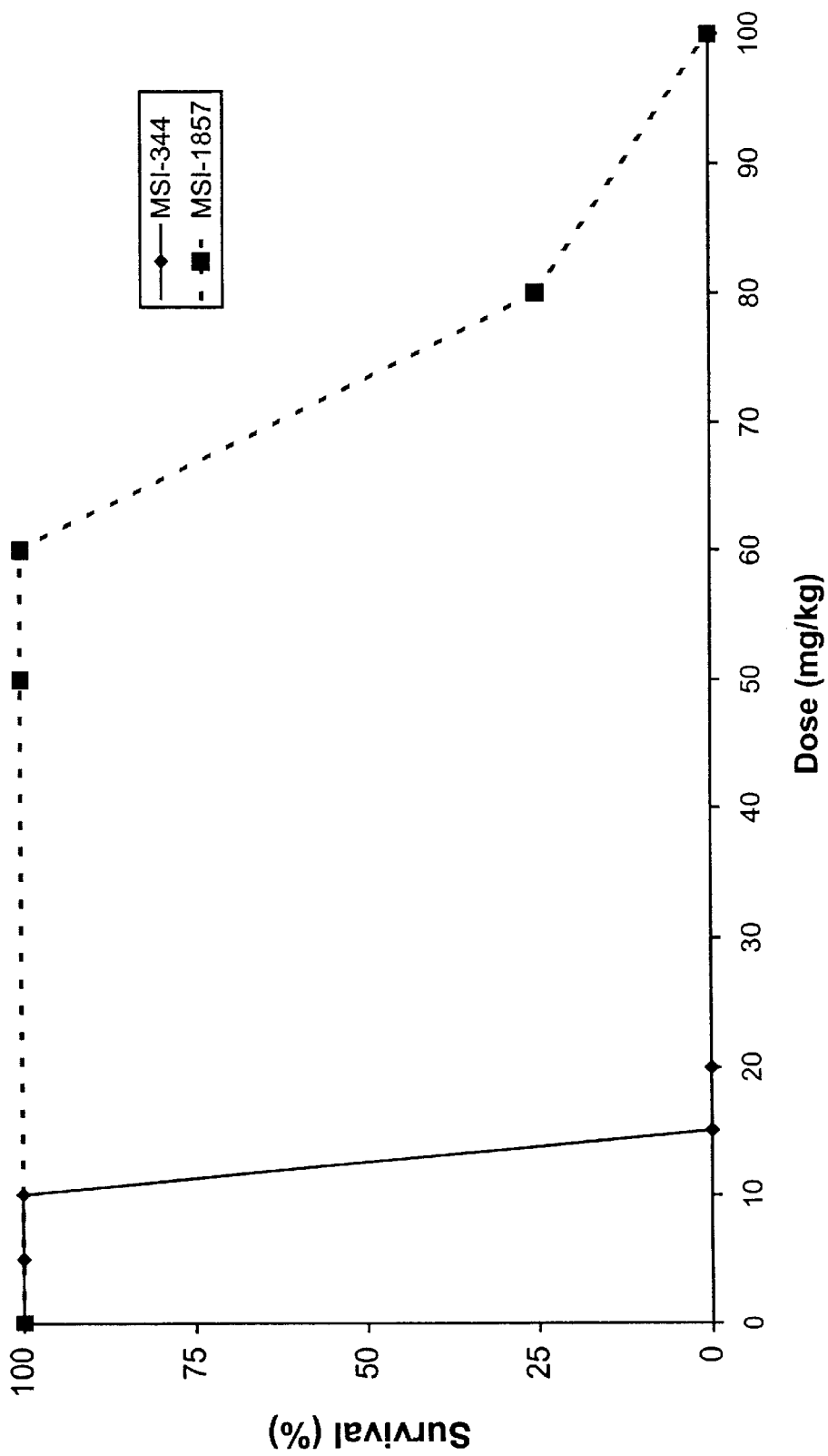
FIG. 10 is a survival curve for CD-1 mice administered a single iv dose of MSI-344(SEQ ID NO: 154 —OH) or MSI-1857(SEQ ID NO: 154 —OH methane sulfonate).
Figure 11:
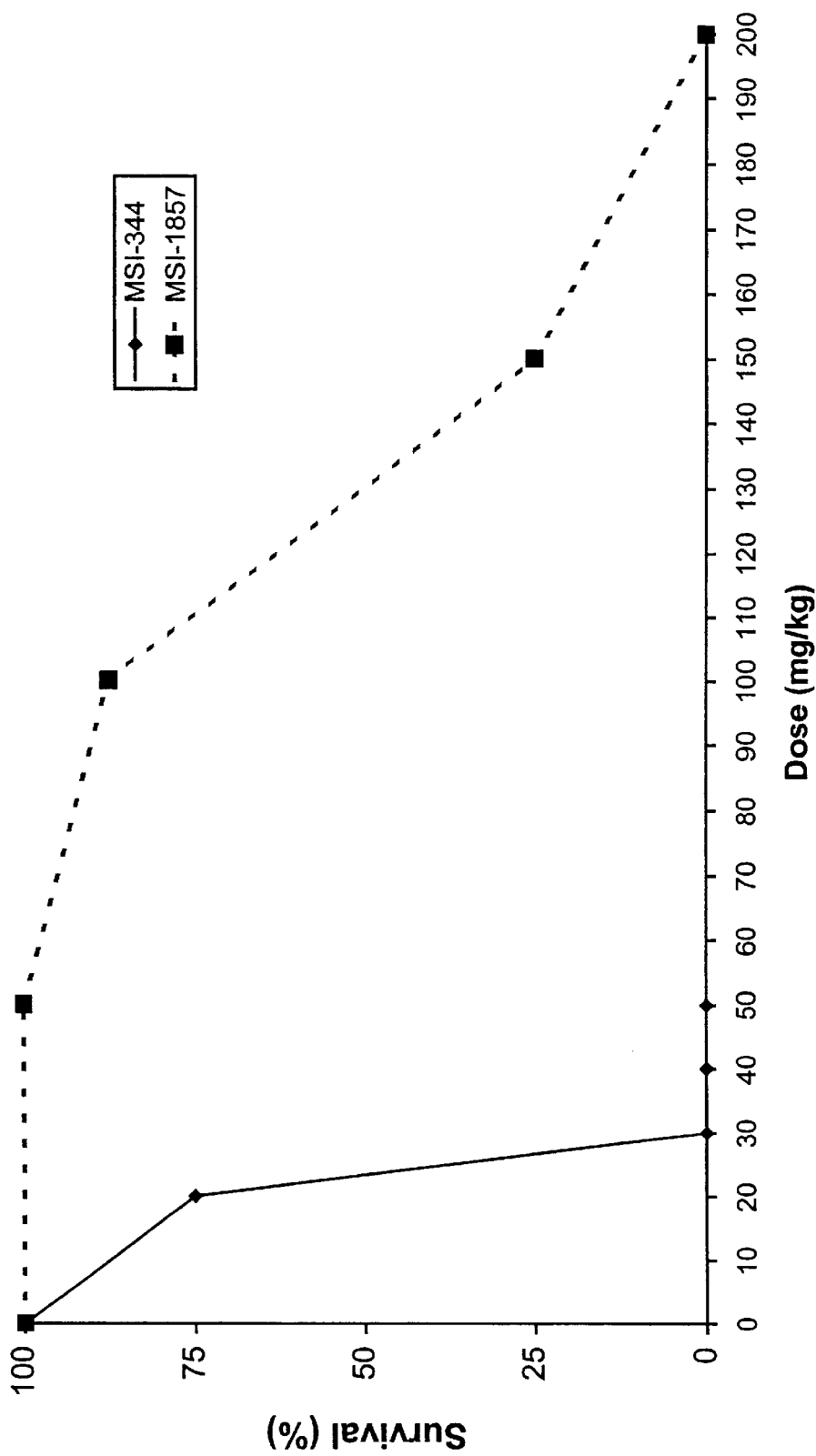
FIG. 11 is a survival curve for CD-1 mice administered a single ip dose of MSI-344(SEQ ID NO: 154 —OH) or MSI-1857(SEQ ID NO: 154 —OH methane sulfonate).

See Table XI for survival results. All animals intravenously dosed with 10 mg/kg or less of MSI-344 survived while all animals dosed with 60 mg/kg of MSI-1857 survived. All animals intraperitoneally dosed with 50 mg/kg of MSI-1857 survived. Dose response curves (FIG. 10) indicated that the LD50s i.v. for MSI-344 and MSI-1857 were approximately 12.5 and 73 mg/kg, respectively. Dose response curves (FIG. 11) indicated that the LD50s i.p. for MSI-344 and MSI-1857 were approximately 23.5 and 120 mg/kg, respectively.

TABLE XI

Survival Count

Tox Study #261

| | | | | No. of Survivors | | | | | | | | | |
|---|---|---|---|---|---|---|---|---|---|---|---|---|---|
| Group | Test Article | Dose (mg/kg) | Route | Day 0[a] | Day 1 | Day 2 | Day 3 | Day 4 | Day 5 | Day 6 | Day 7 | Day 8 | |
| 1 | NaCl | 0 | IV | 4 | 4 | 4 | 4 | 4 | 4 | 4 | 4 | 4 | |
| 2 | MSI-344 | 20 | IV | 2[b] | 0 | 0 | 0 | 0 | 0 | 0 | 0 | 0 | |
| 3 | MSI-344 | 15 | IV | 2[b] | 0 | 0 | 0 | 0 | 0 | 0 | 0 | 0 | |
| 4 | MSI-344 | 10 | IV | 4 | 4 | 4 | 4 | 4 | 4 | 4 | 4 | 4 | |
| 5 | MSI-344 | 5 | IV | 4 | 4 | 4 | 4 | 4 | 4 | 4 | 4 | 4 | |
| 6 | MSI-1857 | 100 | IV | 4 | 0 | 0 | 0 | 0 | 0 | 0 | 0 | 0 | |
| 7 | MSI-1857 | 80 | IV | 4 | 1 | 1 | 1 | 1 | 1 | 1 | 1 | 1 | |
| 8 | MSI-1857 | 60 | IV | 4 | 4 | 4 | 4 | 4 | 4 | 4 | 4 | 4 | |
| 9 | MSI-1857 | 50 | IV | 4 | 4 | 4 | 4 | 4 | 4 | 4 | 4 | 4 | |
| 10 | NaCl | 0 | IP | 4 | 4 | 4 | 4 | 4 | 4 | 4 | 4 | 4 | |
| 11 | MSI-344 | 50 | IP | 4 | 0 | 0 | 0 | 0 | 0 | 0 | 0 | 0 | |
| 12 | MSI-344 | TBD[c] | IP | 4 | 2 | 1 | 1 | 1 | 1 | 1 | 1 | 1 | |
| 13 | MSI-344 | TBD[c] | IP | 4 | 0 | 0 | 0 | 0 | 0 | 0 | 0 | 0 | |
| 14 | MSI-344 | TBD[c] | IP | 4 | 2 | 1 | 1 | 1 | 1 | 1 | 1 | 1 | |
| 15 | MSI-1857 | 200 | IP | 4 | 0 | 0 | 0 | 0 | 0 | 0 | 0 | 0 | |
| 16 | MSI-1857 | 150 | IP | 4 | 1 | 1 | 1 | 1 | 1 | 1 | 1 | 1 | |
| 17 | MSI-1857 | 100 | IP | 4 | 4 | 3 | 3 | 3 | 3 | 3 | 3 | 3 | |
| 18 | MSI-1857 | 50 | IP | 4 | 4 | 4 | 4 | 4 | 4 | 4 | 4 | 4 | |

Tox Study 262

| | | | | No. of Survivors | | | | | | | | | |
|---|---|---|---|---|---|---|---|---|---|---|---|---|---|
| Grp | Test Article | Dose (mg/kg) | Route | Day 0 | Day 1 | Day 2 | Day 3 | Day 4 | Day 5 | Day 6 | Day 7 | Day 8 | Day 11 |
| 1 | Saline | 0 | IP | 4 | 4 | 4 | 4 | 4 | 4 | 4 | 4 | 4 | 4 |
| 2 | MSI-344 | 50 | IP | 4 | 0 | 0 | 0 | 0 | 0 | 0 | 0 | 0 | 0 |
| 3 | MSI-344 | 40 | IP | 4 | 0 | 0 | 0 | 0 | 0 | 0 | 0 | 0 | 0 |
| 4 | MSI-344 | 30 | IP | 4 | 0 | 0 | 0 | 0 | 0 | 0 | 0 | 0 | 0 |
| 5 | MSI-344 | 20 | IP | 4 | 3 | 3 | 3 | 3 | 3 | 3 | 3 | 3 | 3 |
| 6 | MSI-1857 | 150 | IP | 4 | 1 | 1 | 1 | 1 | 1 | 1 | 1 | 1 | 1 |
| 7 | MSI-1857 | 100 | IP | 4 | 4 | 4 | 4 | 4 | 4 | 4 | 4 | 4 | 4 |

[a]Day 0 designates pre-study timepoint (i.e. the number of animals injected)
[b]No. of mice in these groups limited to two because they died immediately after injection and for ethical reasons no more mice were injected with this dose.
TBD[c] An error was made in solution preparation of groups 12, 13, and 14, so results were uninterpertable eliminated from study analysis.
TBD = to be determined, referring to concentrations and dose Conclusions The maximal tolerated doses (MTDs) for intravenous administration of MSI-344 and MSI-1857 (the methane sulfonated MSI-344) were 10 and 60 mg/kg, respectively, in mice. The MTDs for intraperitoneal administration of MSI-344 and MSI-1857 were <20 and 50 mg/kg, respectively.

The approximate dose that caused lethality in 50% of dosed animals (LD50) for intravenous administration of MSI-344 and MSI-1857 in mice were 12.5 and 73 mg/kg, respectively. The LD50s for intraperitoneal administration of MSI-344 and MSI-1857 were approximately 23.5 and 120 mg/kg, respectively.

These results suggest that methane sulfonation of MSI-344 caused a significant improvement in the safety profile (approximately 5-fold increase) compared to MSI-344.

EXAMPLE 12

Study of the Maximal Tolerated Dose (MTD) of Repeat-Dose Intraperitoneal Administration of MSI-344(SEQ ID NO: 154 —OH) and MSI-1857(SEQ ID NO: 154 —OH methane sulfonate)in Mice Summary Determinations of a maximal tolerated dose (MTD) of repeat-dose intraperitoneal (i.p.) administration of MSI-344 or MSI-1857 in 60 SCID mice were done. Mice were injected with various doses of MSI-344 or MSI-1857 twice or thrice per week. Survival and body weight were monitored. On a twice per week dosing schedule, the MTDs of MSI-344 and MSI-1857 were 12 and 134 mg/kg/week, respectively. This demonstrated that MSI-1857 had an 11-fold increase in safety index compared to MSI-344. On a thrice per week dosing schedule, no deaths occurred in any groups, with high dose groups of MSI-344 and MSI-1857 receiving 90 mg/kg/week and 18 mg/kg/week, respectively. A transient body weight loss was seen after initial dosing in most MSI-344 and MSI-1857 groups. No body weight loss greater than 6% occurred in any group on the thrice per week dosing schedule. The results indicate that methane sulfonation of MSI-344 enhances the safety profile compared to MSI-344 in chronic dosing regimens.

Objective

To determine estimates of MTDs of MSI-344 and MSI-1857 when administered intraperitoneally on repeat-dose regimens in SCID mice. The selection of SCID mice was based on the future plans of using this strain as host for xenograft human tumor efficacy models, and a pre-requisite for determining MTD for chronic administration that may be used during the efficacy model.

Material and Methods

Animals

Two groups of sixty SCID male mice (Fox Chase C.B-17/IcrTac-scidfDF, Taconic Labs) exhibited a body weight range of 19.6–25.8 gms at study initiation. SCID mice are immunocompromised and therefore they were housed and handled in sterile environments. They had access to sterile water and sterilized chow ad lib.

Solution Prep

A 1 mg/mL solution of MSI-344 was made in saline (0.9% sodium chloride injection USP, Abbott, North Chicago, Ill.) corrected for peptide content. Solutions of MSI-344 at concentrations of 0.6, 0.3, and 0.1 mg/mL were made by diluting the 1 mg/mL solution using saline as diluent. A 10 mg/mL solution of MSI-1857 was made in saline.

Solutions of MSI-1857 at concentrations of 6.7, 3.3, 3, 2, and 1 mg/mL were made by diluting the 10 mg/mL solution using saline as diluent.

A 4.5 mg/mL solution of sodium metabisulfite (Aldrich Co.) in saline was prepared.

Solutions were made fresh on a weekly basis.

Protocol

Mice (four mice per dose group) were intraperitoneally administered MSI-344 or MSI-1857 using an injection volume of 10 mL/kg of the appropriate solution concentration on a twice per week (Groups 1 through 7) or thrice per week (Groups 8 through 15) dosing schedule every week for 20 weeks. Survival was monitored daily and body weights were recorded three times per week An interim analysis was performed at 3 weeks and the results of this interim analysis is presented in the present report.

Study design is presented in Table XII.

TABLE XII

Study Design for Toxicity Study #261

| Group | Test Article | Dose (mg/kg/inj, IP) | Dosing Regimen | Number of Animals Injected |
|---|---|---|---|---|
| 1 | Saline | 0 | twice per week | 4 |
| 2 | MSI-1857 | 33 | | 4 |
| 3 | | 67 | | 4 |
| 4 | | 100 | | 4 |
| 5 | MSI-344 | 3 | | 4 |
| 6 | | 6 | | 4 |
| 7 | | 10 | | 4 |
| 8 | Saline | 0 | thrice per week | 4 |
| 9 | MSI-1857 | 10 | | 4 |
| 10 | | 20 | | 4 |
| 11 | | 30 | | 4 |
| 12 | MSI-344 | 1 | | 4 |
| 13 | | 3 | | 4 |
| 14 | | 6 | | 4 |
| 15 | Sodium Metabisulfite | 45 | | 4 |

Results

Figure 12:
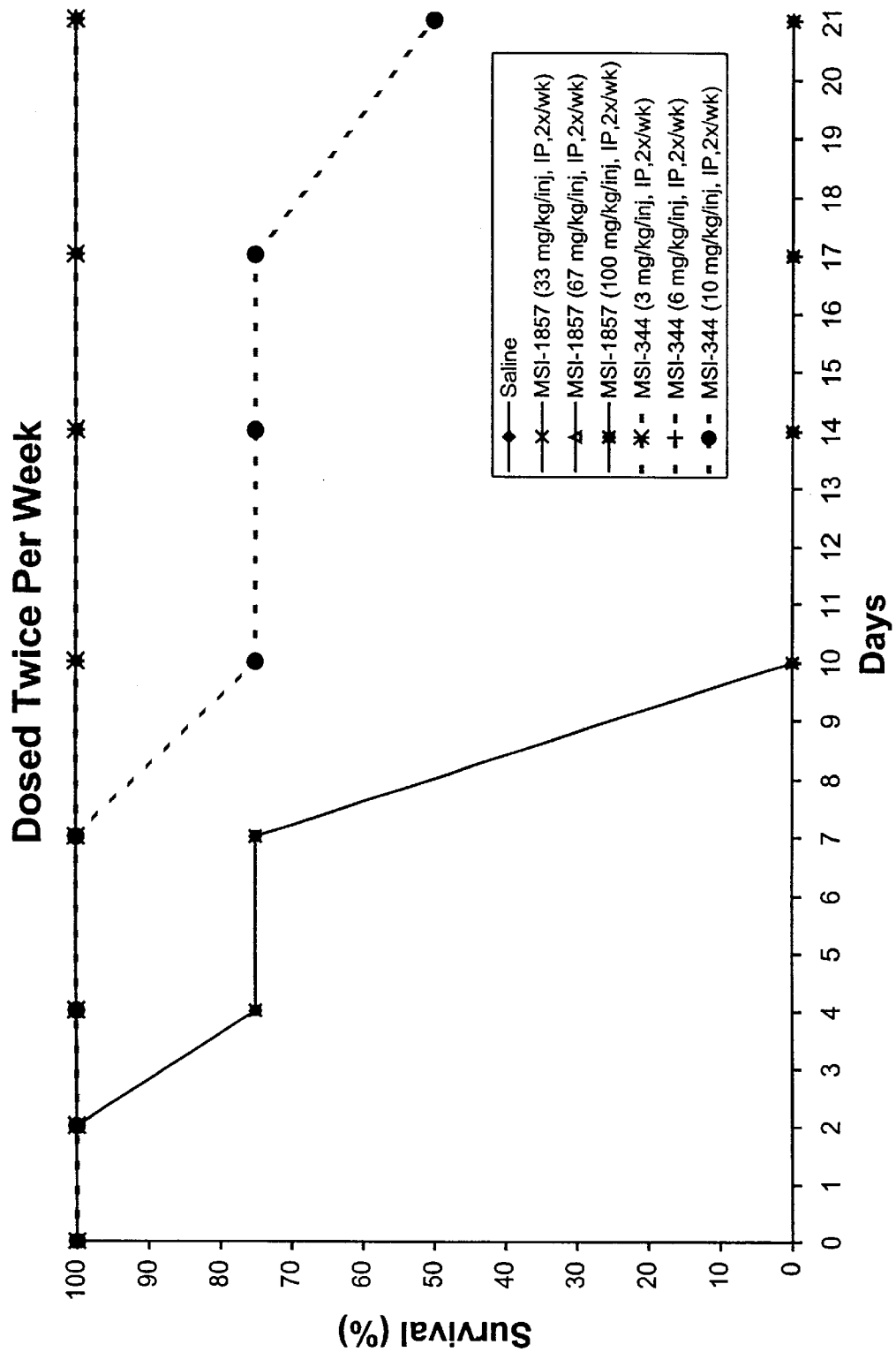
FIG. 12 is a survival curve for SCID mice dosed twice a week with either MSI-344(SEQ ID NO: 154 —OH) or MSI-1857(SEQ ID NO: 154 —OH methane sulfonate).

See FIG. 12 for survival results for the twice per week dosing schedule. All animals in all groups dosed thrice per week survived. The maximal tolerated dose of MSI-1857 was 134 mg/kg/week (i.e. two injections per week times 67 mg/kg/injection) on a twice per week dosing schedule. On the same schedule, the MTD of MSI-344 was 12 mg/kg/week.

The MTDs of MSI-1857 and MSI-344 on a thrice-per-week dosing schedule were ≧90 and 18 mg/kg/week, respectively.

Figure 13:
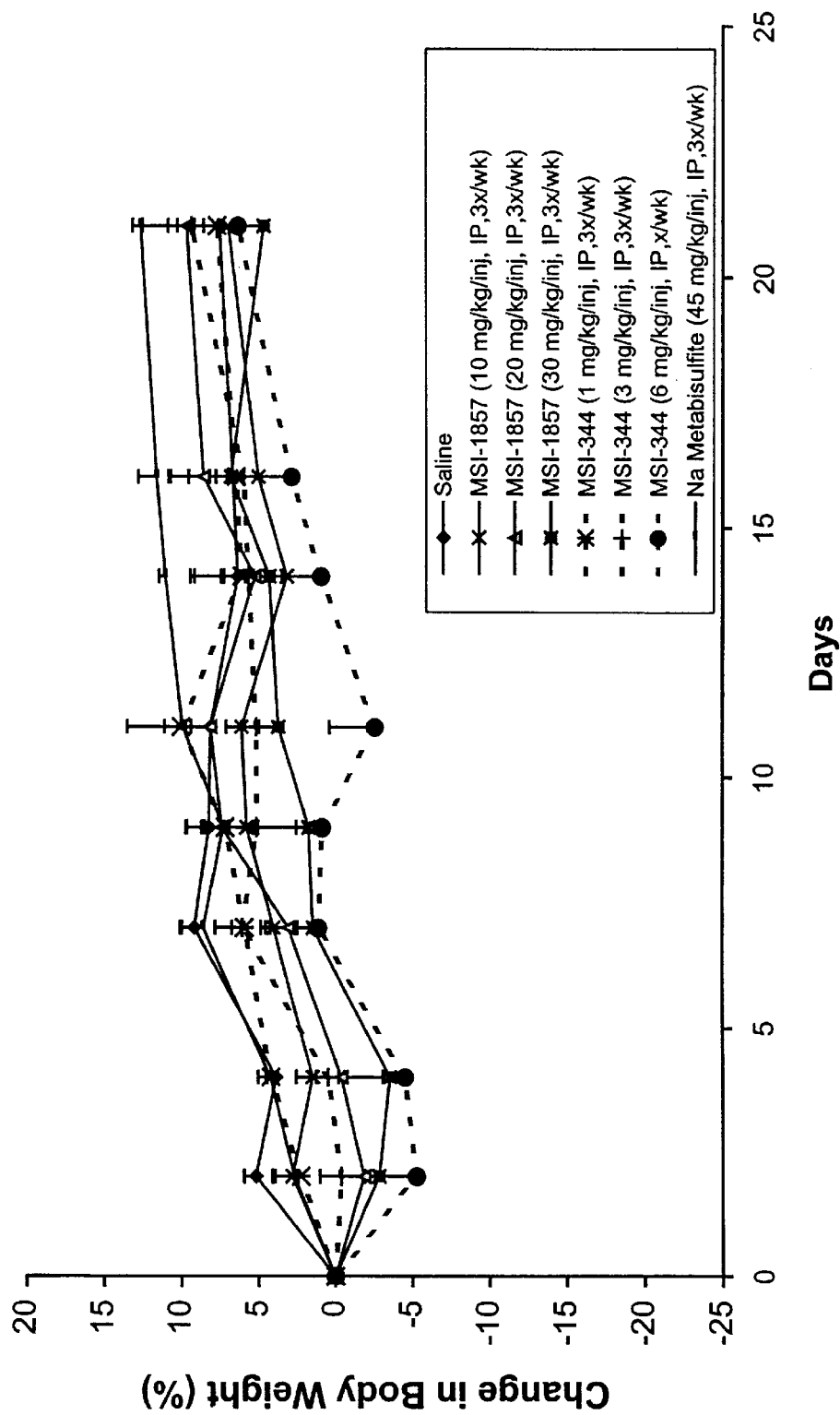
FIG. 13 is a body weight curve for SCID mice dosed three times a week with either MSI-344(SEQ ID NO: 154 —OH) or MSI-1857(SEQ ID NO: 154 —OH methane sulfonate).

The mean body weights are presented in FIGS. 13 and 14. On a twice per week dosing schedule, there were transient decreases in body weights in all groups compared to saline following the initial administrations but the medium- and low-dose groups recovered. On a thrice-per-week dosing schedule, there were transient decreases in body weights in the medium- and high-dose groups but weight gain recovered after the first week of treatment. In both dosing regimens, there was a dose-dependent effect on body weight.

Sodium metabisulfite was dosed at 135 mg/kg/week on three injection per week schedule. This dose is equidose to the quantity of sodium metabisulfite that was used to prepare the MSI-1857 in the MSI-1857 group dosed at 90 mg/kg/week. There was no lethality in this group nor was there any effect of sodium metabisulfite on body weight.

Conclusions

On a twice per week intraperitoneal dosing schedule every week for three weeks, the maximal tolerated dose (MTD) of MSI-1857 (134 mg/kg/week) was 11-fold greater than MSI-344 (12 mg/kg/week) in SCID mice.

On a thrice per week intraperitoneal dosing schedule, the MTD of MSI-1857 was greater than or equal to 90 mg/kg/week and the MTD of MSI-344 was greater than or equal to 18 mg/kg/week.

Initial dosings of MSI-344 or MSI-1857 caused a dose-dependent transient body weight loss in all surviving groups except the low dose group on the thrice-per-week dosing schedule. On the thrice-per-week dosing schedule, the greatest weight loss in any group was less than 6% of initial body weight.

Sodium metabisulfite was administered at a dose that was equivalent to the amount of metabisulfite contained in the MSI-1857 group dosed at 90 mg/kg/week (the dose had been corrected for peptide content). Any toxicity or changes observed in the MSI-1857 group could have been due to the peptide dose or metabisulfite dose, if there was any free, unbound metabisulfite in the solution. The lack of any effect of the metabisulfite on lethality or body weight would suggest that the transient weight loss seen in the MSI-1857 group was not due to free metabisulfite. In addition, even complete release of bound metabisulfite from the high dose group would not cause any deleterious effects on survival or body weight.

The overall results from this study suggest that methane sulfonation of MSI-344 caused a significant improvement in the safety profile (11-fold increase) compared to MSI-344 during chronic dosing.

EXAMPLE 13

Pharmacokinetics Study of Single Dose MSI-1324 (OCT-SEQ ID NO: 143 —$NH_2$ methane sulfonate) Administration in Mice Summary A pharmacokinetics study of MSI-1324 in mice using a single dose administration was conducted. Thirty-two CD-1 male mice were injected with MSI-1324 sodium with a dose of 140 mg/kg (corrected for peptide content). Terminal blood samples were obtained from 2 to 4 mice at timepoints of 0 (prior to dosing), 5, 15, 30, 60 min, 2, 4, 6, 24, and 48 hours post-dose. Plasma concentrations were estimated by bioassay. Peak activity was seen at 5 min post-dose and was below detection limits of the assay by 60 min.

Objective

To determine the pharmacokinetics profile of MSI-1324 after intravenous administration in mice.

Materials and Methods

Animals 40 animals CD-1®BR mice (Charles River Lab) with a mean body weight of 25.6 gms at study initiation were used.

Solution Prep

A 14 mg/mL solution of MSI-1324 was made in saline (0.9% sodium chloride injectable USP, Baxter) corrected for peptide content.

Protocol

Thirty-six mice were intravenously administered a single bolus of MSI-1324 at a dose of 140 mg/kg corrected for peptide content using an injection volume of 10 mL/kg of the 14 mg/mL solution. Four mice were not injected and supplied pre-dosing blood samples. Terminal blood samples were obtained via cardiac puncture in halothane-anesthetized mice at timepoints of 0 (prior to dosing), 5, 15, 30, 60 min, 2, 4, 6, 24, and 48 hours post-dose. Two to four mice were terminally bled at each timepoint. The blood samples were centrifuged and plasma transferred into separate tubes for bioassay analysis. The bioassay used was antibacterial zone clearing (disk diffusion) on *Escherichia coli* lawns.

Results

FIG. 15 shows the standard curve of *E. coli* zone clearing of MSI-1324 used in the bioassay. FIG. 16 shows the plasma concentrations (estimated from the bioassay) in mice at various times after a dose of 140 mg/kg. Peak concentrations of approximately 600 ug/mL were observed at 5 min post-dose (the first sampling timepoint post-dose). Concentrations were below the limit of detection (approximately 150 ug/mL) of the bioassay at 60 min post-dose. The insert in the figure shows no detectable level at later time points.

Conclusions

MSI-1324 showed peak concentrations at 5 min after intravenous administration of 140 mg/kg in mice. Plasma levels were below detection at 60 min and later timepoints.

EXAMPLE 14

In vivo Human Tumor Xenograft Model

For the human lung tumor model, female nude mice weighing approximately 20 g are implanted s.c. by trocar with fragments of SK-MES human lung tumors harvested from s.c. growing tumors in nude mice hosts, while for the human breast tumor model, the mice are injected in the mammary fat pad (mfp) with 1EE6 MDA-MB-435 cells from culture. When tumors reach approximately 5 mm×5 mm (about ten to fourteen days after inoculation), the animals are pair-matched into treatment and control groups. Each group contains 10 tumored mice, each of which is ear-tagged and followed individually throughout the experiment. The administration of drugs or vehicle begins the day the animals are pair-matched (Day 1). The mice are dosed intraparationally either twice or three times a week.

Mice are weighed twice weekly, and tumor measurements are taken by calipers twice weekly, starting on Day 1. These tumor measurements are converted to mg tumor weight by a well-known formula, L5×W/2. The experiment is terminated when control tumors reach a size of 1 gram for the breast tumor model and a size of 2 grams for the lung tumor. Upon termination, all mice are weighed, sacrificed, and their tumors excised. Tumors are weighed, and the mean tumor weight per group is calculated. In this model, the mean treated tumor weight/mean control tumor weight×100 (T/C) is subtracted from 100% to give the tumor growth inhibition (TGI) for each group.

Some drugs cause tumor shrinkage in this human tumor xenograft model. With these agents, the final weight of a given tumor is subtracted from its own weight at the start of treatment on Day 1. This difference divided by the tumor weight is the % shrinkage. A mean % tumor shrinkage can be calculated from data from the mice in a group that experienced tumor regressions. If the tumor completely disappears in a mouse, this is considered a complete regression or complete tumor shrinkage. If desired, mice with partial or total tumor regressions can be kept alive past the termination date to see whether they live to become long term, tumor-free survivors.

Statistics are performed on the data using primarily the log rank p-value test.

The peptides or proteins of the present invention, whether administered alone or in combination with agents such as ions having pharmacological properties, antibiotics, or other biologically active peptides or proteins as hereinabove described, may be employed in a wide variety of pharmaceutical compositions in combination with a non-toxic pharmaceutical carrier or vehicle, such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptides or proteins and/or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The peptides or proteins may be administered to a host, in particular an animal, in an effective antibiotic and/or anti-tumor and/or anti-viral and/or anti-microbial and/or spermicidal and/or anti-fungal and/or anti-parasitic amount, or in an amount effective to stimulate wound healing in a host, or in an amount effective in treating sepsis or septic shock in a host. The peptides or proteins may be administered either alone or in combination with an ion having pharmacological properties, an antibiotic, or an ion channel forming peptide or protein as hereinabove described. When the peptide or protein is administered in combination with an ion having pharmacological properties, the activity of the peptide or protein is potentiated.

When the peptide or protein is administered in combination with an agent as hereinabove described, it is possible to administer the peptide and agent in separate forms. For example, the agent may be administered systemically and the peptide or protein may be administered topically.

When the peptide or protein is administered topically, it may be administered in combination with a water-soluble vehicle, the water-soluble vehicle being in the form of an ointment, cream, lotion, paste, or the like. Examples of water-soluble vehicles which may be employed include, but are not limited to, glycols, such as polyethylene glycol, hydroxycellulose, and KY Jelly. The water-soluble vehicle is preferably free of an oily substance.

The peptide or protein may also be employed alone, or in combination with an ion having pharmacological properties, as hereinabove described, in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal diseases, to prevent or reduce plaque, gingivitis, and/or to prevent or treat or reduce dental caries. The peptide and ion having pharmacological properties may be used to inhibit, prevent, or destroy the growth of *Streptococcus mutans,* which is associated with dental caries and periodontal disease.

It is to be understood, however, that the scope of the present invention is not to be limited to the specific embodiments described above. The invention may be practiced other than as particularly described and still be within the scope of the accompanying claims.

We claim:

1. A method of reducing toxicity of an unsubstituted peptide or an N-terminal substituted peptide having the formula:

wherein X is a biologically active peptide or protein, the peptide being an ion channel-forming peptide or protein, and T is a lipophilic moiety or hydrogen, the method comprising:
   forming a methane sulfonate derivative or analogue of the peptide.

2. A method according to claim 1, wherein said forming step comprises:
   suspending a free base of the unsubstituted peptide or the N-terminal substituted peptide in water; and
   mixing the suspended peptide and at least about 0.5 equivalents of a bisulfite-formaldehyde complex for a period of about 10 minutes or more to produce the methane sulfonate derivative or analogue of the peptide.

3. A method according to claim 1, wherein an anti-microbial activity of the unsubstituted peptide or the N-terminal substituted peptide is not reduced or is not significantly reduced after the methane sulfonate derivative or analogue is formed as compared to an anti-microbial activity of the unsubstituted peptide or the N-terminal substituted peptide not including a methane sulfonate group.

4. A method according to claim 1, wherein an anti-tumor activity of the unsubstituted peptide or the N-terminal substituted peptide is not reduced or is not significantly reduced after the methane sulfonate derivative or analogue is formed as compared to the anti-tumor activity of the unsubstituted peptide or the N-terminal substituted peptide not including a methane sulfonate group.

5. A method of claim 3, wherein said methane sulfonate derivative or analogue is of a peptide selected from the group consisting of: Oct—$NH_2$, Oct—$NH_2$, —$NH_2$, —OH, and —$NH_2$.

6. A method of claim 4, wherein said methane sulfonate derivative or analogue is of a peptide selected from the group consisting of: Oct—$NH_2$, Oct—$NH_2$, —$NH_2$, —OH, and —$NH_2$.

* * * * *

UNITED STATES PATENT AND TRADEMARK OFFICE
CERTIFICATE OF CORRECTION

PATENT NO.   : 6,348,445 B1  Page 1 of 1
DATED        : February 19, 2002
INVENTOR(S)  : U. Prasad Kari et al.

It is certified that error appears in the above-identified patent and that said Letters Patent is hereby corrected as shown below:

<u>Column 120,</u>
Lines 30 and 31, should read -- Oct-[SEQ ID NO. 143]-$NH_2$, Oct-[SEQ ID NO. 27]-$NH_2$, [SEQ ID NO. 154]-$NH_2$, [SEQ ID NO. 154]-OH, and [SEQ ID NO. 155]-$NH_2$. -- and
Lines 35 and 36 should read -- Oct-[SEQ ID NO. 143]-$NH_2$, Oct-[SEQ ID NO. 27]-$NH_2$, [SEQ ID NO. 154]-$NH_2$, [SEQ ID NO. 154]-OH, and [SEQ ID NO. 155]-$NH_2$. --

Signed and Sealed this

Tenth Day of September, 2002

Attest:

JAMES E. ROGAN
*Attesting Officer*    *Director of the United States Patent and Trademark Office*